United States Patent
Lilly et al.

(10) Patent No.: US 11,896,807 B2
(45) Date of Patent: Feb. 13, 2024

(54) CONVERTIBLE PLUNGERS AND METHODS FOR ASSEMBLING THE SAME IN A MEDICAL BARREL

(71) Applicant: SIO2 MEDICAL PRODUCTS, INC., Auburn, AL (US)

(72) Inventors: Brian Russell Lilly, Auburn, AL (US); Kenneth Wade Kelly, Auburn, AL (US); Joseph W. Rogers, Lafayette Hill, PA (US); Jean-Pierre Giraud, Auburn, AL (US); Bruce Rabinne, Boissy-le-Chatel (FR); Herve Pichot, Chennevieres-sur-Marne (FR); Benjamin Hunt, Auburn, AL (US); Zachary Dean Freeman, Auburn, AL (US); Dalton Roe, Auburn, AL (US); Robert S. Abrams, Albany, NY (US)

(73) Assignee: SIO2 MATERIAL PRODUCTS, INC, Auburn, AL (US)

( * ) Notice: Subject to any disclaimer, the term of this patent is extended or adjusted under 35 U.S.C. 154(b) by 353 days.

(21) Appl. No.: 17/248,972

(22) Filed: Feb. 16, 2021

(65) Prior Publication Data
US 2021/0275752 A1 Sep. 9, 2021

Related U.S. Application Data

(63) Continuation of application No. 16/306,536, filed as application No. PCT/US2017/013337 on Jan. 13, 2017, now Pat. No. 10,918,800.
(Continued)

(51) Int. Cl.
*A61M 5/315* (2006.01)
*A61F 9/00* (2006.01)
*A61M 5/31* (2006.01)

(52) U.S. Cl.
CPC ....... *A61M 5/31513* (2013.01); *A61F 9/0008* (2013.01); *A61M 2005/3101* (2013.01); *A61M 2005/3121* (2013.01); *A61M 2207/00* (2013.01)

(58) Field of Classification Search
CPC .......... A61M 5/31513; A61M 5/31511; A61M 5/31515; A61M 2005/3101; A61M 2005/3121
See application file for complete search history.

(56) References Cited

U.S. PATENT DOCUMENTS

| 2,895,773 A | 7/1959 | McConnaughey |
| 3,669,111 A | 6/1972 | Dubner |

(Continued)

FOREIGN PATENT DOCUMENTS

| CA | 1324545 C | 11/1993 |
| DE | 202007005394 U1 | 9/2007 |

(Continued)

OTHER PUBLICATIONS

International Search Report issued in PCT/US2014/059531, dated Jun. 29, 2015.
(Continued)

*Primary Examiner* — Laura A Bouchelle
(74) *Attorney, Agent, or Firm* — David B. Gornish; Eckert Seamans Cherin & Mellott, LLC

(57) ABSTRACT

Disclosed are plunger assemblies including various convertible plungers and methods of making the same. Each plunger assembly is configured for disposition within a barrel of a medical container, e.g., a syringe, and displaced within the barrel from an engagement position to a release position. The engagement position is configured to provide a compression seal between a storage sealing section of the plunger and an inner wall of the syringe barrel. In the release
(Continued)

position, the compression seal is reduced or eliminated. Also disclosed are methods for making convertible plungers and assembling them into syringes, e.g., pre-filled syringes.

17 Claims, 38 Drawing Sheets

Related U.S. Application Data

(60) Provisional application No. 62/343,536, filed on May 31, 2016.

(56) References Cited

U.S. PATENT DOCUMENTS

| | | | |
|---|---|---|---|
| 4,064,879 | A | 12/1977 | Leibinsohn |
| 5,195,975 | A * | 3/1993 | Castagna ............ A61M 5/5066 604/218 |
| 5,314,416 | A | 5/1994 | Lewis et al. |
| 5,413,563 | A | 5/1995 | Basile et al. |
| 5,735,825 | A | 4/1998 | Stevens et al. |
| 5,951,527 | A | 9/1999 | Sudo |
| 6,129,712 | A | 10/2000 | Sudo et al. |
| 6,190,363 | B1 | 2/2001 | Gabbard et al. |
| D447,799 | S | 9/2001 | Jun |
| 6,749,590 | B2 | 6/2004 | Niedospial, Jr. |
| 7,547,297 | B2 | 6/2009 | Brinkhues |
| D612,493 | S | 3/2010 | Claessens et al. |
| 7,691,308 | B2 | 4/2010 | Brinkhues |
| 7,766,882 | B2 | 8/2010 | Sudo et al. |
| 7,927,315 | B2 | 4/2011 | Sudo et al. |
| 7,955,309 | B2 | 6/2011 | Cude |
| 7,985,188 | B2 | 7/2011 | Felts et al. |
| 8,167,850 | B2 | 5/2012 | Hoffmann et al. |
| 8,460,250 | B2 * | 6/2013 | Imai ................ A61M 5/31513 604/220 |
| 8,496,643 | B2 | 7/2013 | Chebator et al. |
| 8,574,201 | B2 | 11/2013 | Chattaraj et al. |
| 8,668,972 | B2 | 3/2014 | Lewis et al. |
| 8,722,178 | B2 | 5/2014 | Ashmead et al. |
| 8,960,685 | B2 | 2/2015 | Maeda et al. |
| 9,108,012 | B2 | 8/2015 | Pryce Lewis et al. |
| 9,192,725 | B2 | 11/2015 | Kawamura |
| D746,448 | S | 12/2015 | Wu et al. |
| D747,471 | S | 1/2016 | Gulliver et al. |
| D751,699 | S | 3/2016 | Mills |
| D771,247 | S | 11/2016 | Shinohara et al. |
| 9,511,192 | B2 | 12/2016 | Kawamura |
| 9,522,237 | B2 | 12/2016 | Alheidt et al. |
| D781,418 | S | 3/2017 | Winsor |
| 9,592,346 | B2 | 3/2017 | Quinn et al. |
| D784,529 | S | 4/2017 | Steele et al. |
| D787,052 | S | 5/2017 | Heinz et al. |
| 9,642,969 | B2 | 5/2017 | Ivosevic et al. |
| 9,649,444 | B2 | 5/2017 | Schiller et al. |
| D789,528 | S | 6/2017 | Wohlfahrt et al. |
| 9,717,857 | B2 | 8/2017 | Lanier |
| D797,928 | S | 9/2017 | Davis et al. |
| D797,929 | S | 9/2017 | Davis et al. |
| D799,032 | S | 10/2017 | Becker |
| 9,827,376 | B2 | 11/2017 | Titus et al. |
| 9,981,089 | B2 | 5/2018 | Ishida et al. |
| 10,159,796 | B2 | 12/2018 | Schiff et al. |
| 10,918,800 | B2 * | 2/2021 | Lilly .................... A61F 9/0008 |
| 2008/0300550 | A1 | 12/2008 | Schiller et al. |
| 2009/0097995 | A1 | 4/2009 | Ham et al. |
| 2009/0166978 | A1 | 7/2009 | Hoffmann et al. |
| 2010/0179487 | A1 | 7/2010 | Woehr |
| 2011/0196313 | A1 | 8/2011 | Mudd |
| 2011/0024611 | A1 | 9/2011 | Lum et al. |
| 2012/0253291 | A1 | 10/2012 | Ivosevi et al. |
| 2013/0041241 | A1 | 2/2013 | Felts et al. |
| 2013/0082057 | A1 | 4/2013 | Schiff et al. |
| 2013/0085452 | A1 | 4/2013 | Schiff et al. |
| 2013/0126559 | A1 | 5/2013 | Cowan et al. |
| 2013/0138050 | A1 | 5/2013 | Jugl et al. |
| 2013/0209766 | A1 | 8/2013 | Felts et al. |
| 2013/0291632 | A1 | 11/2013 | Felts et al. |
| 2014/0228774 | A1 | 8/2014 | Maeda et al. |
| 2014/0319778 | A1 | 10/2014 | Kawasaki et al. |
| 2014/0339776 | A1 | 11/2014 | Nakano et al. |
| 2014/0339777 | A1 | 11/2014 | Nakano et al. |
| 2015/0148751 | A1 | 5/2015 | Yotsutsuji |
| 2015/0231337 | A1 | 8/2015 | Hara et al. |
| 2015/0273155 | A1 | 10/2015 | Kaneko et al. |
| 2015/0367076 | A1 | 12/2015 | Matsutani et al. |
| 2016/0146346 | A1 | 5/2016 | Shimizu et al. |
| 2019/0009035 | A1 | 1/2019 | Lum et al. |

FOREIGN PATENT DOCUMENTS

| | | |
|---|---|---|
| EP | 1849490 A1 | 10/2007 |
| EP | 2565006 A2 | 3/2013 |
| EP | 2703025 A1 | 3/2014 |
| EP | 2796159 A1 | 10/2014 |
| EP | 2803378 A1 | 11/2014 |
| EP | 2902060 A1 | 8/2015 |
| EP | 2910265 A1 | 8/2015 |
| EP | 2926851 A1 | 10/2015 |
| EP | 2957310 A1 | 12/2015 |
| EP | 1703930 B1 | 2/2018 |
| GB | 578827 | 7/1946 |
| GB | 1168201 | 10/1969 |
| JP | 06327770 A | 11/1994 |
| JP | 08182760 A | 7/1996 |
| JP | 2001025506 A | 1/2001 |
| JP | 2008154644 A | 7/2008 |
| JP | 2010504776 A | 2/2010 |
| JP | 2015070914 A | 4/2015 |
| WO | 2007118907 A1 | 10/2007 |
| WO | 2011059823 A1 | 5/2011 |
| WO | 2012076494 A1 | 6/2012 |
| WO | 2013156524 A1 | 10/2013 |
| WO | 2014050550 A1 | 4/2014 |
| WO | 2014085348 A2 | 6/2014 |
| WO | 2014164928 A1 | 10/2014 |
| WO | 2015054282 A2 | 4/2015 |

OTHER PUBLICATIONS

Written Opinion issued in PCT/US2014/059531, dated Jun. 29, 2015.
International Search Report issued in PCT/US2015/024558, dated Dec. 22, 2015.
Written Opinion issued in PCT/US2015/024558, dated Dec. 22, 2015.
International Search Report issued in PCT/US2016/042167, dated Oct. 25, 2016.
Written Opinion issued in PCT/US2016/042167, dated Oct. 25, 2016.
International Search Report issued in PCT/US2017/013337, dated May 11, 2017.
Written Opinion issued in PCT/US2017/013337, dated May 11, 2017.

* cited by examiner

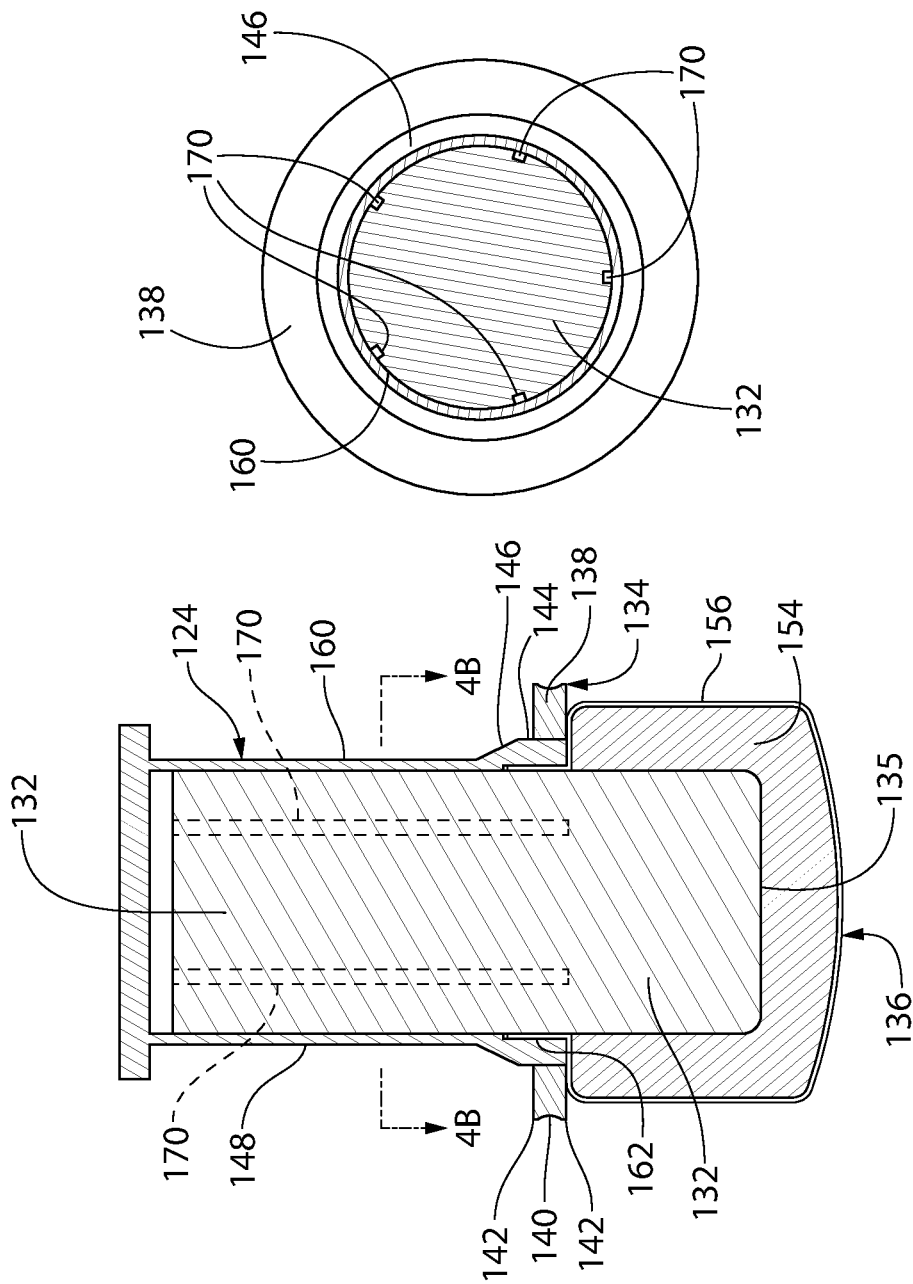

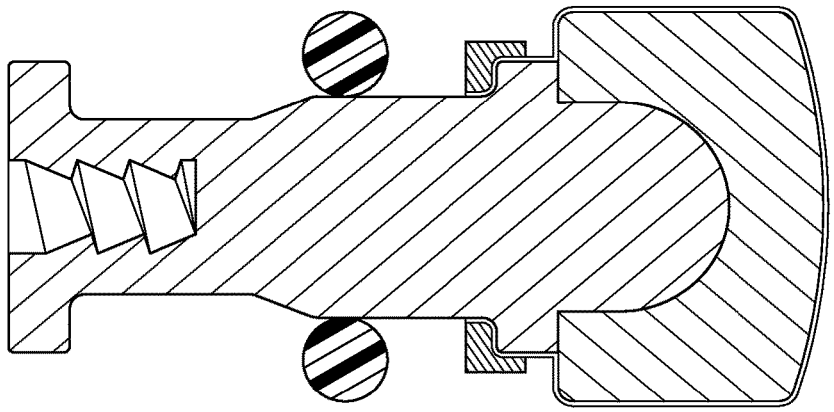
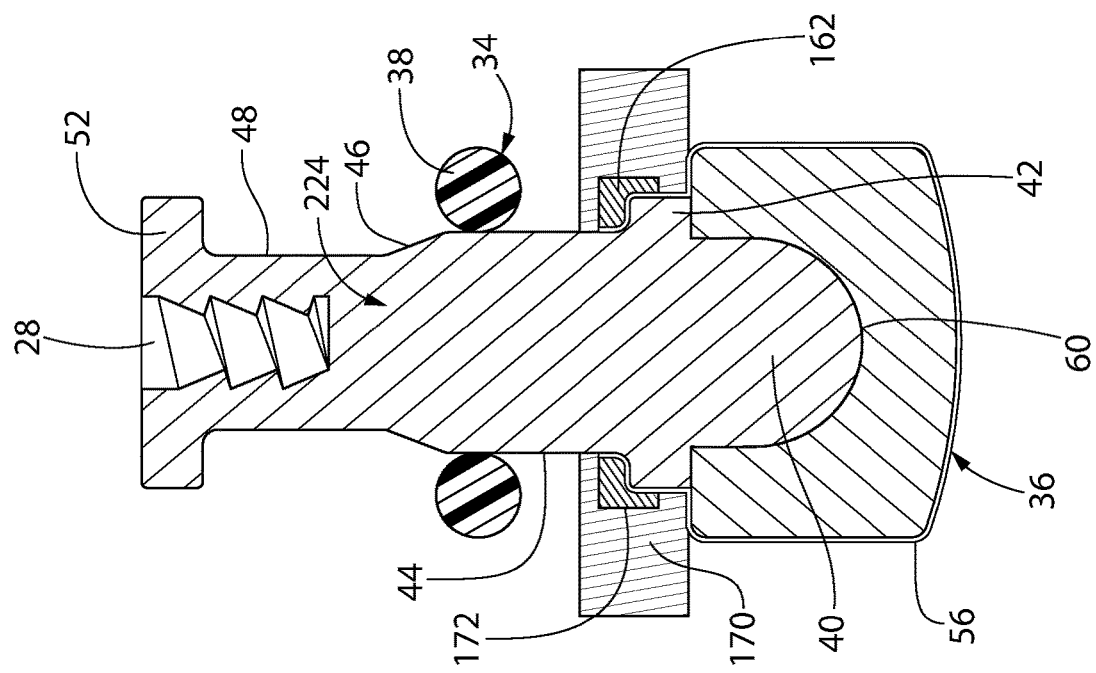
FIG. 5B
FIG. 5A

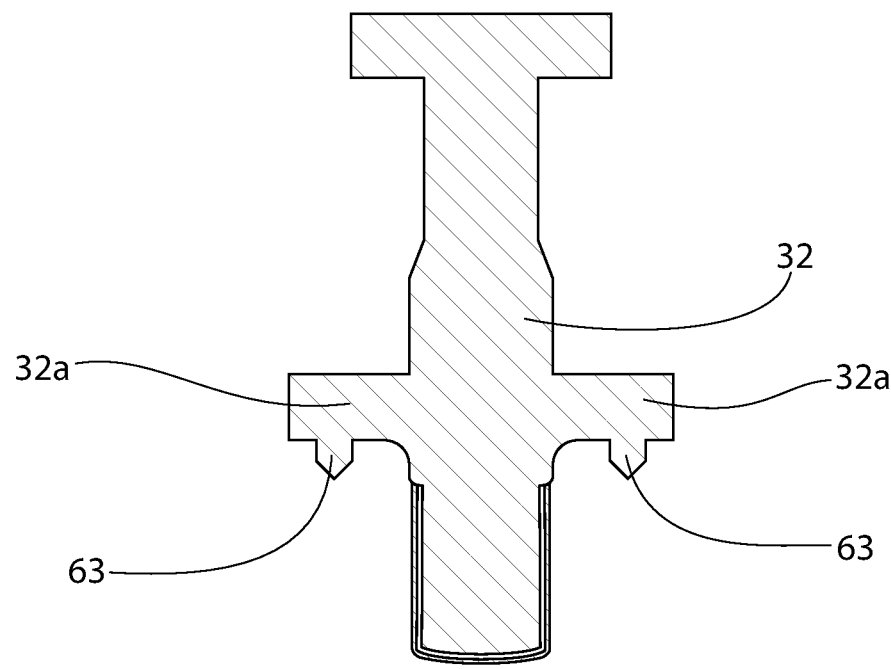
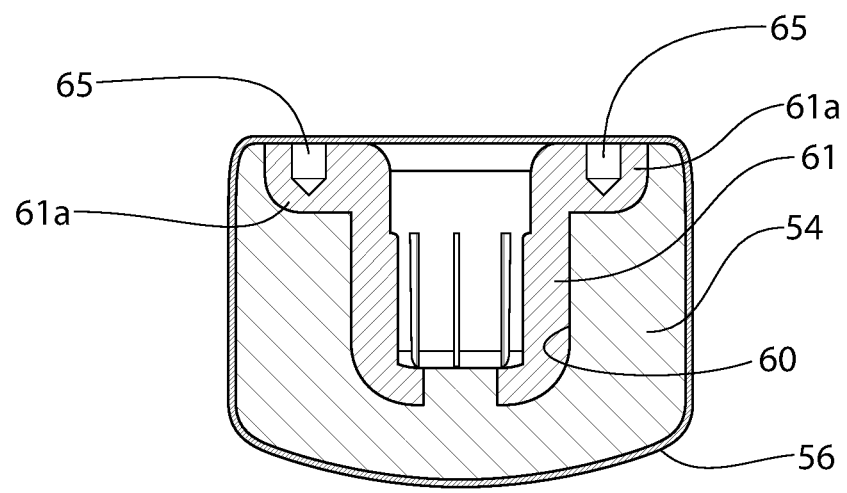
FIG. 9

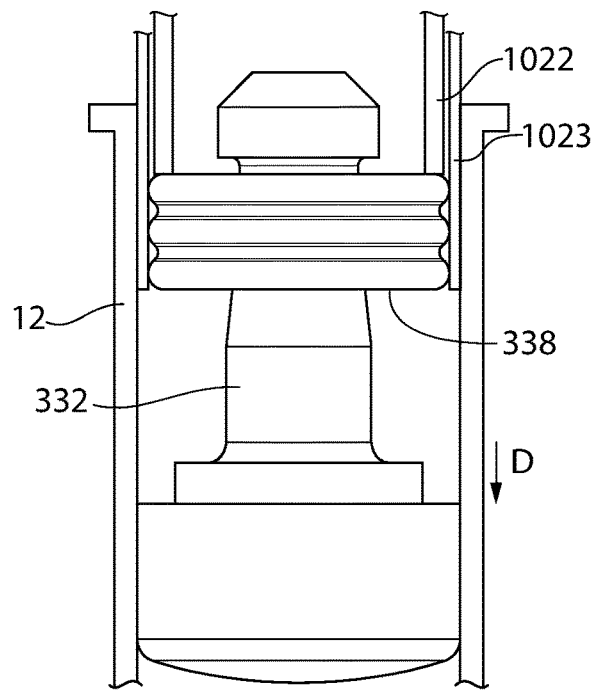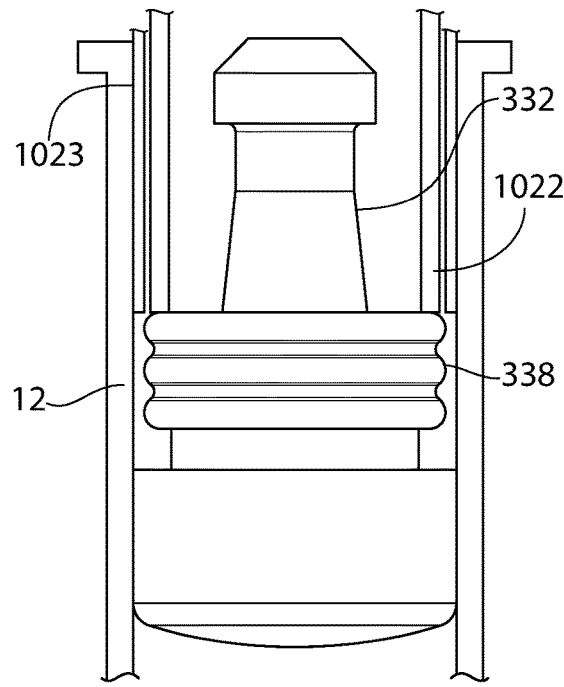
FIG. 14A    FIG. 14B
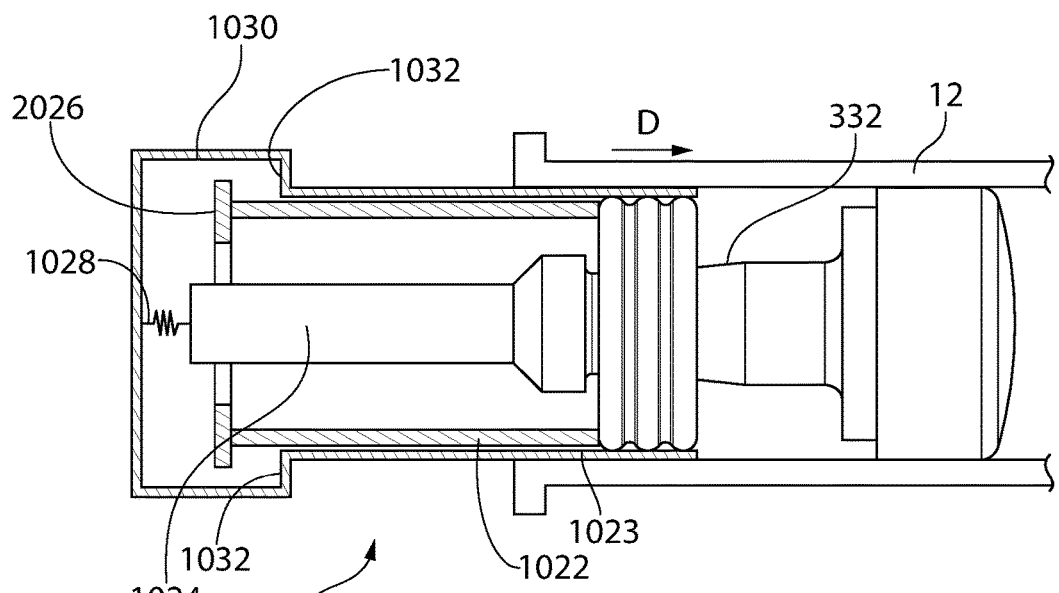
FIG. 14C

CONVERTIBLE PLUNGERS AND METHODS FOR ASSEMBLING THE SAME IN A MEDICAL BARREL

CROSS-REFERENCE TO RELATED APPLICATIONS

This application is a continuation application of U.S. application Ser. No. 16/306,536 filed Nov. 30, 2018, now U.S. Pat. No. 10,918,800 issued Feb. 16, 2021 which is a U.S. National Phase of International Application No. PCT/US2017/013337 filed Jan. 13, 2017, which claims priority to U.S. Provisional Patent Application No. 62/343,536 filed May 31, 2016 and International Application No. PCT/US2016/042167, filed Jul. 31, 2016 which are incorporated herein by reference in their entirety.

FIELD OF INVENTION

The invention relates generally to plungers and their use in drug delivery devices, such as (prefilled, filled before use or empty) syringes, cartridges or auto-injectors. More particularly, the invention relates to convertible plungers that provide and maintain container closure integrity and gas-tight seal in a storage mode (during the shelf life of, e.g., a prefilled syringe) and then are convertible to a dispensing mode. The dispensing mode facilitates relatively low and smooth/consistent plunger force when dispensing syringe contents.

BACKGROUND

The present disclosure predominantly describes use of convertible plungers according to the present invention in connection with prefilled syringes. However, a skilled artisan would readily appreciate that the invention is not limited to prefilled syringes, but may include other drug delivery devices, such as (prefilled, filled before use, or empty) syringes, cartridges and auto-injectors as well as prefilled syringes or other barrels used for diagnostics applications.

Prefilled parenteral containers, such as syringes or cartridges, are commonly prepared and sold so that the syringe does not need to be filled by the patient or caregiver before use. The syringe, and more specifically the barrel of the syringe, may be prefilled with a variety of different injection products, including, for example, saline solution, a dye for injection, or a pharmaceutically active preparation, among other items.

Prefilled parenteral containers are typically sealed with a rubber plunger, which provides closure integrity over the shelf life of the container's contents. To use the prefilled syringe, the packaging and cap are removed, optionally a hypodermic needle or another delivery conduit is attached to the distal end of the barrel, the delivery conduit or syringe is moved to a use position (such as by inserting it into a patient's tissue or into apparatus to be rinsed with the contents of the syringe), and the plunger is advanced in the barrel to inject contents of the barrel to the point of application.

Seals provided by rubber plungers in the barrel typically involve the rubber of the plunger being pressed against the barrel. Typically, the rubber plunger is larger in diameter than the internal diameter of the barrel. Thus, to displace the rubber plunger when the injection product is to be dispensed from the syringe requires overcoming this pressing force of the rubber plunger. Moreover, not only does this pressing force provided by the rubber seal typically need to be overcome when initially moving the plunger, but this force also needs to continue to be overcome as the rubber plunger is displaced along the barrel during the dispensing of the injection product. The need for relatively elevated forces to advance the plunger in the syringe may increase the user's difficulty in administering the injection product from the syringe. This is particularly problematic for auto injection systems where the syringe is placed into the auto injection device and the plunger is advanced by a fixed spring. Accordingly, primary considerations concerning the use of a plunger in a prefilled parenteral container include: (1) container closure integrity ("CCI", defined below) and gas-tightness; and (2) plunger force (defined below) required to dispense syringe contents.

In practice, maintaining CCI/gas-tightness and providing desirable plunger force tend to be competing considerations. In other words, absent other factors, the tighter the fit between the plunger and the interior surface of the container to maintain adequate CCI/gas-tightness, the greater the force necessary to advance the plunger in use. In the field of medical syringes, it is important to ensure that the plunger can move at a substantially constant speed and with a substantially constant and relatively low force when advanced in the barrel. In addition, the force necessary to initiate plunger movement and then continue advancement of the plunger should be low enough to enable comfortable administration by a user and prevent jolting or unnecessarily high pressing force that can cause patient discomfort.

Plunger force is essentially a function of the coefficients of friction of each of the contacting surfaces (i.e., the plunger surface and interior syringe wall surface) and the normal force exerted by the plunger against the interior wall of the syringe. The greater the respective coefficients of friction and the greater the normal force, the more force required to advance the plunger. Accordingly, efforts to improve plunger force should be directed to reducing friction and lowering normal force between contacting surfaces. However, such efforts are preferably tempered by the need to maintain adequate CCI and gas-tightness, as discussed above.

To reduce friction and thus improve plunger force, lubrication is traditionally applied to the barrel-contacting engagement surface of the plunger, the interior surface of the barrel, or both. Liquid or gel-like flowable lubricants, such as free silicone oil (e.g., polydimethylsiloxane or "PDMS"), may provide a desired level of lubrication between the plunger and the barrel to optimize plunger force. PDMS is, in fact, a standard flowable lubricant used in the industry. However, for preferred embodiments of the invention, use of flowable lubricant between the plunger and the barrel is not desired. One reason is that a flowable lubricant can mix and interact with the drug product in a syringe, potentially degrading the drug or otherwise affecting its efficacy and/or safety. Degradation is particularly an issue in the case of protein compositions and polypeptide compositions, which occupy a market with tremendous growth potential. Further, such lubricants may in some cases be problematic if they are injected into the patient along with the drug product. In addition, flowable lubricants, when used with prefilled syringes, may migrate away from the plunger over time, resulting in spots between the plunger and the interior surface of the container with little or no lubrication. This may cause a phenomenon known as "sticktion," an industry term for the adhesion between the plunger and the barrel that needs to be overcome to break out the plunger and allow it to begin moving. For these reasons, there is an industry need for an "oil free" solution, i.e., a plunger that is entirely or at least substantially free of flowable lubricant between the plunger and the barrel and wherein such flowable lubricant is absent from the drug product stream.

As an alternative (or in addition) to flowable lubricants, plungers may be made from materials having lubricious properties or include friction-reducing coatings or film laminates on their exterior surfaces. Examples of such plungers include, for example: the i-COATING by TERUMO, which is disclosed in Canadian Patent No. 1,324,545, incorporated by reference herein in its entirety; W. L. Gore extended ETFE film on a rubber plunger; and the CZ plunger by WEST. However, film coated plungers alone are considered to provide inadequate CCI or gas-barrier properties. For example, while fluoropolymer films on plungers provide excellent lubricious properties, they are known to provide poor gas barriers. Accordingly, a conventional fluoropolymer film laminated plunger alone may not be a viable solution for a prefilled syringe that houses product which is sensitive to certain gases.

Thus, there is a need for plungers that balance desirable plunger force in a parenteral container with maintaining adequate CCI and (as the case may be) gas-tight sealing to prevent drug leakage, protect the drug product and attain sufficient product shelf life. In addition, there is a need to provide adequate lubricity to achieve a desired plunger force while preventing adverse effects of flowable lubricant-generated particles and interaction with the drug product held by the container. There is a further need to optimize these factors while reducing manufacturing costs and complexity. The subject invention preferably addresses those needs, and others.

SUMMARY OF THE INVENTION

One aspect of this invention is a convertible plunger. The convertible plunger has an internal portion and a generally cylindrical exterior surface that surrounds at least part of the internal portion. The generally cylindrical exterior surface includes a compressible and resilient storage sealing section that is maintained in an expanded state by outward radial pressure provided by the internal portion. The internal portion is comparatively more rigid than the storage sealing section. The expanded state is reducible to a constricted state by an operation that is applied to the internal portion of the plunger to reduce or eliminate the outward radial pressure. The storage sealing section, in the constricted state, has a reduced maximum diameter or cross-sectional width than the storage sealing section in the expanded state and/or is less resistant to inward radial compression compared to the storage sealing section in the expanded state. The storage sealing section is configured to be set in the expanded state through application of a setting force onto the convertible plunger in a distal direction, optionally when the convertible plunger is disposed in a medical barrel. The operation is application of an actuation force onto the convertible plunger in the distal direction, optionally when the convertible plunger is disposed in a medical barrel.

Another aspect of this invention is a pre-filled syringe having a convertible plunger according to any embodiment disposed therein. The pre-filled syringe, according to an optional embodiment, includes a medical barrel having an inner wall and an injectable drug product, optionally a liquid composition, disposed in a product containing area of the medical barrel. The medical barrel has a distal dispensing end for dispensing the injectable drug product and an open proximal end configured for receipt of a convertible plunger.

Optionally in any embodiment of a syringe according to the invention, the convertible plunger provides a break loose force and glide force below 15 N, optionally below 10 N, optionally below 9 N, optionally below 8 N, optionally below 7 N, optionally below 6 N, optionally below 4 N, optionally between 2 N and 5.5 N, optionally between 2 N and 4 N, entirely without the presence of a flowable lubricant between the inner wall of the medical barrel and the convertible plunger's barrel-contacting surfaces.

Optionally in any embodiment of a convertible plunger according to the invention, a plunger head is provided at a distal end of the convertible plunger. The plunger head includes a liquid sealing section configured to provide a liquid tight seal and optionally a CCI seal against an inner wall of a medical barrel. The plunger head comprises a first component. The storage sealing section is mounted to and axially movable about a second component or integral with the second component. The first component and second component are separate components that are assembled to form the convertible plunger.

Optionally in any embodiment of a pre-filled syringe according to the invention, the injectable drug product, optionally a liquid composition, disposed in a product containing area of the medical barrel, includes a polypeptide composition or protein composition. In this optional embodiment, desirable plunger forces are achieved entirely without the presence of a flowable lubricant between the inner wall of the medical barrel and the convertible plunger's barrel-contacting surfaces. In addition, flowable lubricant-generated particles are absent from the drug product.

In an optional aspect, the invention is a method for assembling a convertible plunger into a medical barrel to form a syringe. Such a method may include providing a medical barrel, inserting a convertible plunger through an open proximal end of the barrel, disposing the plunger within the medical barrel proximal to the product containing area. The method includes applying a setting force onto the convertible plunger in a distal direction in order to set the storage sealing section in the expanded state, thereby placing the convertible plunger in the storage mode. A convertible plunger, as may be used in this method, may include an internal portion and a generally cylindrical exterior surface that surrounds at least part of the internal portion. The generally cylindrical exterior surface has a compressible and resilient storage sealing section that is maintained in an expanded state by outward radial pressure provided by the internal portion, thereby rendering the convertible plunger in storage mode. The internal portion is comparatively more rigid than the storage sealing section. The expanded state is reducible to a constricted state by an operation that is applied to the internal portion of the plunger to reduce or eliminate the outward radial pressure to transition the convertible plunger from the storage mode to a dispensing mode. The storage sealing section in the constricted state has a reduced maximum diameter or cross-sectional width than the storage sealing section in the expanded state and/or is less resistant to inward radial compression compared to the storage sealing section in the expanded state. Optionally, according to this method, the convertible plunger in the storage mode is configured to transition to the dispensing mode upon providing an actuation force onto the convertible plunger in a distal direction. Optionally, according to this method, the syringe is pre-filled in a manufacturing filling process with a drug product in the product containing area. Optionally, according to this method, flowable lubricant is absent from the product containing area.

Optionally, according to any embodiment of a syringe according to the invention, the barrel is made from an injection moldable thermoplastic resin, optionally COP or COC.

Optionally, according to any embodiment of a syringe according to the invention, the barrel has an organo-siloxane coating or layer on the interior wall of the barrel, optionally wherein the organosiloxane coating or layer is a pH protective coating, optionally as a top layer of a tri-layer coating set.

Optionally, according to any embodiment of a pre-filled syringe according to the invention, the storage sealing section in the expanded state forms a liquid-tight, CCI and gas-tight interface with the interior wall of the barrel, optionally wherein the gas-tight interface is substantially impermeable to oxygen, nitrogen, water vapor and/or ethylene oxide.

Optionally, according to any embodiment of a pre-filled syringe according to the invention, the storage sealing section in the expanded state forms a CCI and gas-tight seal over a product shelf-life of 6 months, one year, optionally 18 months, optionally 24 months, optionally three years.

Optionally, according to any embodiment of a pre-filled syringe according to the invention, the plunger provides a differential between break loose force and glide force of optionally below 20%, optionally below 15%, optionally below 12%, optionally below 10%, optionally below 8%, optionally between 2.5% and 6% entirely without the presence of a flowable lubricant between the barrel and the plunger's barrel-contacting surfaces.

Optionally, according to any embodiment, the convertible plunger is secured to a plunger rod, forming a plunger assembly, wherein the plunger rod is configured to be pressed in a distal direction to actuate the plunger and dispense drug product.

Optionally, according to any embodiment of a pre-filled syringe according to the invention, the drug product is an injectable liquid selected from the group consisting of: a small molecule pharmaceutical drug product, a biologic, a vaccine, a peptide-based drug, a protein-based drug, sterile water or saline solution for injection and a diagnostic medium.

Optionally, according to any embodiment of a pre-filled syringe according to the invention, the drug product is selected from group consisting of: diagnostic agents (e.g., dyes or contrast agents), vaccines, injections for research purposes (e.g., placebos), chemotherapeutic agents, contrast agents, immunogens, antigens, interferons, polyclonal antibody preparations, monoclonal antibodies, anesthetics, interfering RNAs, gene vectors, insulins, carriers, excipients, diluents and combinations of two or more of the foregoing.

Optionally, according to any embodiment of a pre-filled syringe according to the invention, a drug product disposed in the syringe is selected from the group of biopharmaceutical products set forth in BIOPHARMA: Biopharmaceutical Products in the U.S. and European Markets—Recent U.S. Approvals, Jul. 13, 2016, pp. 1-20, http://www.biopharma.com/approvals.html, which is incorporated by reference herein in its entirety for all purposes. It is contemplated that at least some of these biopharmaceutical products are susceptible to one or more negative effects from interaction with particles generated from a flowable lubricant. Such negative effects may include: denaturing of proteins in the composition, agglomeration of proteins in the composition, degradation of proteins in the composition, triggering an undesired immune response in a patient who is administered the drug product and degrading efficacy of the drug product. In an optional embodiment of the invention, flowable-lubricant generated particles are absent from the biopharmaceutical drug product such that the drug product is not subject to the one or more of the aforementioned negative effects from flowable-lubricant generated particles.

Optionally, according to any embodiment of a syringe according to the invention, the medical barrel is made from glass.

Optionally, according to any embodiment of a syringe according to the invention, the convertible plunger includes a liquid sealing section that is located distal to the storage sealing section. The liquid sealing section includes a film coating having a lower coefficient of friction than a substrate to which the film coating is applied. The film coating is optionally a fluoropolymer film. The liquid sealing section preferably provides a liquid tight seal against the inner wall of the barrel.

Optionally, according to any embodiment of a plunger or pre-filled syringe according to the invention, the storage sealing section includes at least two annular ribs separated by an annular valley therebetween.

Optionally, any embodiment of a pre-filled syringe according to the invention may be a component of an auto injector.

Optionally, any embodiment of a syringe according to the invention is a 0.5 mL syringe. Optionally, any embodiment of a syringe according to the invention includes a barrel having an inner diameter of from 2.5 mm to 4.6 mm. Applicants have successfully reduced to practice a functional convertible plunger in a 0.5 mL syringe. It is a notable achievement that a convertible plunger, with small separate cooperating components, is workable in such small syringe dimensions.

Optionally, for any embodiment of a syringe according to the invention, the storage sealing section is on an outer storage ring disposed about the convertible plunger. The convertible plunger is configured to axially translate distally relative to the storage ring when transitioning from storage mode to dispensing mode.

Optionally, for any embodiment of a pre-filled syringe according to the invention, the injectable drug includes a polypeptide composition or protein composition that is susceptible to one or more negative effects from interaction with particles generated from a flowable lubricant. Such negative effects may include: denaturing of proteins in the composition, agglomeration of proteins in the composition, degradation of proteins in the composition, triggering an undesired immune response in a patient who is administered the drug product and degrading efficacy of the drug product.

In one aspect, the invention is optionally directed to a method for using any syringe embodiment disclosed herein for ophthalmic applications. The syringe for such applications contains 5-50 microliters, optionally 10-30 microliters, optionally 10-20 microliters of ophthalmic drug in the product-containing space. The barrel has an inner diameter of from 2.5 mm to 4.6 mm. The method includes inserting a needle into a patient's eye tissue wherein the needle provides fluid communication from the product-containing area through the dispensing end of the barrel and actuating the convertible plunger to transition from storage mode to dispensing mode. The "inserting" step may precede the "actuating" step or vice versa. Further, the method includes injecting the ophthalmic drug into the patient's eye tissue.

In another optional embodiment, the invention is a convertible plunger for disposition within a barrel of a medical container. The barrel is configured for receipt of an injectable product therein and having a central axis and an interior wall surrounding the axis. The plunger is configured to be moved within the barrel along the axis from a storage mode to a dispensing mode. The plunger includes a ring carrier having a compressible and resilient storage ring disposed thereon. The ring is configured to displace axially, optionally by sliding, along the ring carrier from an engagement position to a release position. In the engagement position, the storage ring is disposed about a storage platform of the ring carrier. In the release position, the storage ring is disposed about a dispensing platform having a narrower maximum cross-sectional width or diameter than the storage platform. The storage platform is optionally comparatively more rigid than the storage ring. The storage ring includes a storage sealing section configured to apply outward radial pressure on the interior wall when the storage sealing section is in the engagement position. The storage sealing section is configured in the release position to provide reduced or no outward radial pressure on the interior wall. The plunger further includes a plunger head mounted at a distal end of the plunger, the plunger head having a liquid sealing section configured to contact and provide a seal against the interior wall. The plunger head is a separate component assembled with the ring carrier, directly or indirectly, to form the convertible plunger. Indirect assembly could include intervening component(s) between the plunger head and ring carrier, e.g., the connector body, discussed below.

In another optional embodiment, the invention is a convertible plunger. The plunger includes first and second subassemblies or articles secured to each other. The first subassembly or article includes an optionally polymeric and optionally generally cylindrical connector body having a distal end and a proximal end. The first subassembly further includes a plunger head, which is a separate component that is assembled to the distal end of the connector body. The plunger head has a liquid sealing section configured to contact and provide a seal against an interior wall of a medical barrel when disposed therein. The second subassembly or article includes an elongate ring carrier, which is optionally polymeric, having a distal end and a proximal end. The distal end of the ring carrier is secured to the proximal end of first subassembly. The proximal end of the ring carrier is configured to be secured to a plunger rod. The ring carrier comprises, from its proximal end, an annular dispensing platform and an annular storage platform distal to the dispensing platform. The annular storage platform has a larger maximum diameter or cross-sectional width than the dispensing platform. The second subassembly further includes a compressible and resilient storage ring, which is optionally elastomeric, disposed about the ring carrier and configured to displace axially thereon, optionally to slide axially thereon. The storage platform is optionally comparatively more rigid than the storage ring. Optionally, the proximal end of the connector body includes a recess or axial channel, the ring carrier further including an annular insertion platform distal to the annular storage platform. The annular insertion platform has a smaller maximum diameter or cross-sectional width than the storage platform. The insertion platform is disposed in the recess or axial channel so as to fixedly secure the first subassembly to the second subassembly.

Optionally, according to any embodiment of a convertible plunger according to the invention, there is a fluoropolymer film wrapped about the liquid sealing section.

Optionally, according to any embodiment of a convertible plunger according to the invention, the storage ring includes at least two annular ribs separated by an annular valley therebetween. Optionally, the storage ring includes exactly three annular ribs with exactly two annular valleys respectively separating the ribs.

Optionally, according to any embodiment of a convertible plunger according to the invention, the storage ring in an uncompressed state includes a rib on an inside surface of the storage ring and an opposing rib on the outer surface of the storage sealing section. The opposing ribs have peaks that are preferably aligned along the same radial plane.

Optionally, according to any embodiment of a convertible plunger according to the invention, the storage ring includes an outer surface facing generally radially outward away from the ring carrier. When the storage ring is in an uncompressed state, the outer surface comprises a proximal end, a distal end and a radial plane of symmetry between the proximal and distal ends, optionally equidistant from the proximal and distal ends, wherein the outer surface is symmetrical on either side of the radial plane of symmetry.

Optionally, according to any embodiment, the convertible plunger may be disposed in a pre-filled syringe. When the storage ring is disposed about the storage platform, the storage sealing section is maintained in an expanded state by outward radial pressure provided by the storage platform to create compression between the storage sealing section and the inner wall of the barrel. This renders the convertible plunger in storage mode. The expanded state is reducible to a constricted state upon transitioning the storage ring to being disposed about the dispensing platform whereupon the compression between the storage sealing section and the inner wall of the barrel is reduced or eliminated, thereby rendering the convertible plunger in dispensing mode. Optionally, the entire storage ring is disposed about the storage platform when the plunger is in storage mode. Optionally, the entire storage ring is disposed about the dispensing platform when the plunger is in dispensing mode. Optionally, the storage sealing section is configured to be set in the expanded state through application of a setting force onto the convertible plunger in a distal direction. Optionally, the convertible plunger in storage mode is configured to transition to dispensing mode upon providing an actuation force onto the convertible plunger in a distal direction.

In an optional embodiment, the invention is an assembly including a plunger head that has a compressible and resilient material, optionally an elastomer or thermoplastic elastomer. The plunger head is configured for providing a seal, optionally a liquid tight seal when disposed in a medical barrel. The plunger includes a distal product-facing surface, a proximal end and a sidewall therebetween configured for contacting an inner wall of a medical barrel to form the seal when disposed in the medical barrel. The assembly further includes a rigid component or rigid subassembly, optionally a ring carrier, a central core and/or a connector body, fixedly secured at a distal end of the rigid component or rigid subassembly, to the proximal end of the plunger head. A fluoropolymer film piece is wrapped about the plunger head, entirely covering the product-facing surface and sidewall. The fluoropolymer film piece has an edge about its perimeter, wherein the edge is not exposed on the assembly. For example, the edge may be sandwiched between the plunger head and the rigid component or rigid subassembly.

In an optional embodiment, the invention is a method for making a fluoropolymer film coated liquid sealing section for a plunger, optionally as a component of a convertible plunger, according to various process steps disclosed herein. Optionally, the plunger head comprises an elastomer disposed over a polymer support. The plunger head is optionally made through two-shot injection molding. Optionally, the elastomer of the plunger head comprises a polyolefin based thermoplastic elastomer and the polymer support comprises a polyolefin, optionally polypropylene, cyclic olefin polymer or cyclic olefin copolymer.

In an optional embodiment, the invention is a method for making an assembly. The method includes providing a plunger head comprising a compressible and resilient material, optionally an elastomer, disposed over a comparatively more rigid polymer support. The plunger head includes a distal product-facing surface, a proximal end and a sidewall therebetween configured for contacting an inner wall of a medical barrel to form a seal, optionally a liquid tight seal, when disposed in a medical barrel. Optionally, a fluoropolymer film is wrapped about the plunger head, entirely covering the product-facing surface and sidewall. The method further includes providing a polymeric and optionally generally cylindrical connector body having a distal end and a proximal end, the proximal end of the plunger head being assembled to the distal end of the connector body and optionally secured thereto by joining, optionally by welding (e.g., ultrasonic welding), the rigid support of the plunger head to the distal end of the connector body. Respective materials of the rigid support and connector body are configured to be compatible with each other for ultrasonic welding. The method further includes providing an elongate polymeric ring carrier having a distal end and a proximal end. The distal end of the ring carrier is assembled to the proximal end of the connector body. The ring carrier comprises a material having lower gas permeability, optionally lower oxygen permeability, nitrogen permeability, water vapor permeability and/or ethylene oxide permeability, than the connector body. Optionally, as part of the method, an elastomeric storage ring is disposed about the ring carrier. The ring carrier is configured to displace axially relative to the storage ring. However, broadly, this embodiment is not limited to convertible plungers and the storage ring may be omitted in appropriate cases, e.g., for non-prefilled syringe applications.

Optionally, in any embodiment, the storage ring is an elastomer.

Optionally, in any embodiment, the storage ring does not make direct material contact with injectable product in the product containing area.

Optionally, in one embodiment, the invention is a method for assembling a convertible plunger into a pre-filled syringe. The method includes providing a syringe barrel having a central axis and an interior wall surrounding the axis, the barrel including a dispensing end, an open top and a product containing area therebetween. The product containing area is pre-filled to a desired amount with an injectable drug product, optionally a liquid composition. A first subassembly or article is provided and includes a rigid and generally cylindrical connector body having a distal end and a proximal end. The proximal end has a recess or axial channel. The first subassembly further includes a plunger head, which is a separate component that is assembled to the distal end of the connector body. The plunger head has a liquid sealing section configured to contact and provide a seal against the interior wall of the barrel when disposed therein. A second subassembly or article is provided. The second subassembly has a rigid elongate ring carrier having a distal end and a proximal end. The distal end is configured to be secured to the first subassembly. The proximal end is configured to be secured to a plunger rod. The ring carrier includes, from its proximal end, an annular dispensing platform, and an annular storage platform distal to the dispensing platform. The annular storage platform has a larger maximum diameter or cross-sectional width than the dispensing platform. There is an annular insertion platform distal to the annular storage platform, the annular insertion platform having a smaller maximum diameter or cross-sectional width than the storage platform. The second subassembly further includes a compressible and resilient storage ring, which is optionally elastomeric, disposed about the ring carrier and configured to displace axially thereon, optionally to slide axially thereon. The first subassembly is loaded into the syringe barrel, with the plunger head located distally in the barrel with respect to the connector body, the loading step optionally being achieved through a vent tube, vacuum or vacuum assist loading method. The method further includes positioning the storage ring about the insertion platform and axially aligning the second subassembly with the recess or axial channel of the connector body, the distal end of the ring carrier facing the recess or axial channel. After positioning and aligning, the method includes moving the first subassembly toward the second subassembly and/or vice versa to dispose the second subassembly into the syringe barrel, whereupon the insertion platform is inserted into the recess or axial channel while the storage ring contacts the proximal end of the connector body. As the insertion platform is further inserted into the storage ring, the storage ring is pushed off the insertion platform and is disposed about the storage platform, creating a compression seal between the storage ring and the interior wall of the barrel and fixedly securing the first subassembly to the second subassembly. In this way, convertible plunger may optionally be assembled. Optionally by this method, a pressure zone is not created between the storage ring and the first subassembly or the plunger head. Optionally, the convertible plunger in storage mode is configured to transition to a dispensing mode upon providing an actuation force onto the convertible plunger in a distal direction.

In an optional embodiment, the invention is a convertible plunger assembly configured to be disposed within a syringe barrel and advanced in a dispensing direction to dispense the contents of the syringe barrel. The plunger assembly includes a plunger having an axial cavity and at least two axially spaced generally annular ribs. Each rib has an inner diameter and an outer diameter, joined by an intermediate sleeve portion of reduced outer diameter. The plunger assembly further includes a sliding shaft that is received in the axial cavity and displaceable along its axis. The sliding shaft includes at least one annular cylindrical ring and at least one reduced diameter portion axially displaced from the ring.

In an optional embodiment, a convertible plunger for disposition within a barrel of a medical container is provided. The barrel is configured for receipt of an injectable product therein and has a central axis and an interior wall surrounding the axis. The plunger is configured to be moved within the barrel along the axis from a storage mode to a dispensing mode. The plunger includes a ring carrier having a compressible and resilient storage ring disposed on the ring carrier. The storage ring is configured for axial displacement along the ring carrier, optionally by sliding. The ring carrier includes an annular storage platform that is optionally comparatively more rigid than the storage ring. The storage ring is in an expanded state corresponding to an engagement position when the storage ring is disposed about the storage platform. In the engagement position, a storage sealing section of the storage ring is configured to apply outward radial pressure on the interior wall of the barrel. The ring carrier further includes an annular dispensing platform having a narrower cross-sectional width or diameter than that of the storage platform. The storage ring is in a constricted state corresponding to a release position when the storage ring is disposed about the dispensing platform. In the release position, the storage sealing section is configured to provide less radial pressure on the interior wall than when in the engagement position or to provide no outward radial pressure on the interior wall. The ring carrier further includes an annular insertion platform having a smaller maximum diameter or cross-sectional width than that of the storage platform. The storage ring is in a load position when disposed about the insertion platform so as to facilitate insertion of the ring carrier and storage ring into the barrel. In load position, the storage sealing section is configured to provide less radial pressure on the interior wall than when in the engagement position or to provide no outward radial pressure on the interior wall. The storage ring is configured to move along the ring carrier between the load position, the engagement position and the release position. The plunger further includes a plunger head mounted at a distal end of the plunger, the plunger head having a liquid sealing section configured to contact and provide a seal against the interior wall. The plunger head is a separate component assembled with the ring carrier to form the convertible plunger.

Optionally, the liquid sealing section has a film or a cap covering a product-facing surface and sidewall of the liquid sealing section, the film or cap optionally comprising a fluoropolymer.

Optionally, the storage sealing section includes a plurality of annular ribs separated by an annular valley between ribs. Optionally, the storage ring includes a storage sealing section having three outer annular ribs separated by annular valleys and a single inner rib or lobe on an inner diameter of the ring.

Optionally, the ring carrier includes a transition region connecting the storage platform to the dispensing platform. The dispensing platform and transition region together provide a uniform annular inner radius about the ring carrier. The uniform annular inner radius includes complementary mating geometry with the single inner rib so as to securely retain the storage ring about the dispensing platform when the storage ring is in the release position.

Optionally, the liquid sealing section comprises a thermoset rubber, e.g., butyl rubber.

Optionally, the convertible plunger includes a connector body, which is preferably a rigid and generally cylindrical member. The connector body has a distal end and a proximal end, the distal end of the connector body being secured to the plunger head, the proximal end of the connector body being secured to a distal end of the ring carrier.

Optionally, the liquid sealing section of the plunger has a film wrapped around a product-facing surface and sidewall of the liquid sealing section. The film optionally includes a fluoropolymer. The film continues along an underside of the plunger head and is sandwiched between the plunger head and the connector body.

Optionally, the insertion platform is distal to the storage platform and the storage platform is distal to the dispensing platform.

In an optional aspect, a method for assembling a convertible plunger into a pre-filled syringe is provided. The method includes providing a syringe barrel having a central axis and an interior wall surrounding the axis. The barrel has a dispensing end, an open top and a product containing area therebetween, the product containing area being pre-filled to a desired amount with an injectable product, optionally a liquid composition. The method includes providing first and second articles configured for assembly to each other, wherein the first article has at least a plunger head and the second article has a ring carrier having a compressible and resilient storage ring disposed on it. The storage ring is configured for axial displacement along the ring carrier, optionally by sliding. The ring carrier is provided substantially as disclosed in the preceding ring carrier embodiment, with an annular storage platform, an annular dispensing platform and an annular insertion platform. The plunger head is provided at a distal end of the plunger, the plunger head having a liquid sealing section configured to contact and provide a seal against the interior wall of the syringe barrel. The method includes loading the first article into the syringe barrel through the open top thereof, the loading step optionally being achieved through a vent tube, vacuum or vacuum assist loading method. The method includes positioning the storage ring about the insertion platform and axially aligning the second article with the first article. Next, and while the storage ring is in load position, the method includes disposing the second article into the open end of the syringe barrel at least to a depth in which the storage ring is disposed within the syringe barrel. Finally, the method includes assembling the first and second articles to form the convertible plunger and move the storage ring from load position to engagement position.

In an optional aspect of the aforementioned method, the first article further includes a connector body, which is preferably a rigid and generally cylindrical member, the connector body having a distal end and a proximal end, the distal end of the connector body being secured to the plunger head, the proximal end of the connector body being securable to the second article to form the convertible plunger. Optionally, the connector body has a distal end and a proximal end, the proximal end having a recess or axial channel. The insertion platform is provided at a distal end of the ring carrier. Assembly of the connector body and ring carrier is effectuated by inserting the insertion platform into the recess or axial channel while the storage ring contacts the proximal end of the connector body, whereupon the storage ring is pushed off the insertion platform and is disposed about the storage platform. This places the storage ring into the engagement position and fixedly secures the first article to the second article, thereby assembling the convertible plunger.

Optionally, when the storage ring is in the load position, the storage ring does not contact the barrel wall.

Optionally according to the aforementioned method, the storage ring is positioned flush against the proximal end of the first article when the ring transitions from load position to engagement position.

Additional methods for making plunger assemblies and inserting them into prefilled syringes are disclosed.

BRIEF DESCRIPTION OF THE DRAWINGS

The invention will be described in conjunction with the following drawings in which like reference numerals designate like elements and wherein:

FIG. 4A is an enlarged axial sectional view of another exemplary embodiment of a convertible plunger constructed in accordance with this invention, and which convertible plunger can be used in any application that the convertible plunger shown in FIG. 1 can be used.

FIG. 4B is a sectional view taken along line 4B-4B of FIG. 4A.

FIG. 5A is an enlarged axial sectional view of still another exemplary embodiment of a convertible plunger constructed in accordance with this invention shown in the process of assembling the plunger.

FIG. 5B is an enlarged axial sectional view, similar to FIG. 5A, but showing the plunger after it has been assembled, whereupon it can be used in any application that the convertible plunger shown in FIG. 1 can be used.

FIG. 9 is an exploded axial section view of an exemplary plunger constructed in accordance with this invention, illustrating yet another optional configuration for applying film thereto.

FIG. 14A is a partial schematic illustration of an alternative embodiment of a plunger insertion apparatus, according to an aspect of the invention, for inserting the plunger of FIG. 10 into a medical barrel, wherein the storage ring is in a pre-storage sealing mode.

FIG. 14B is the same partial schematic illustration as FIG. 14A, except that the storage ring is set in storage sealing mode.

FIG. 14C is a more complete schematic illustration of FIG. 14A, showing additional components of the plunger insertion apparatus.

DETAILED DESCRIPTION OF THE PREFERRED EMBODIMENTS

Figure 1:
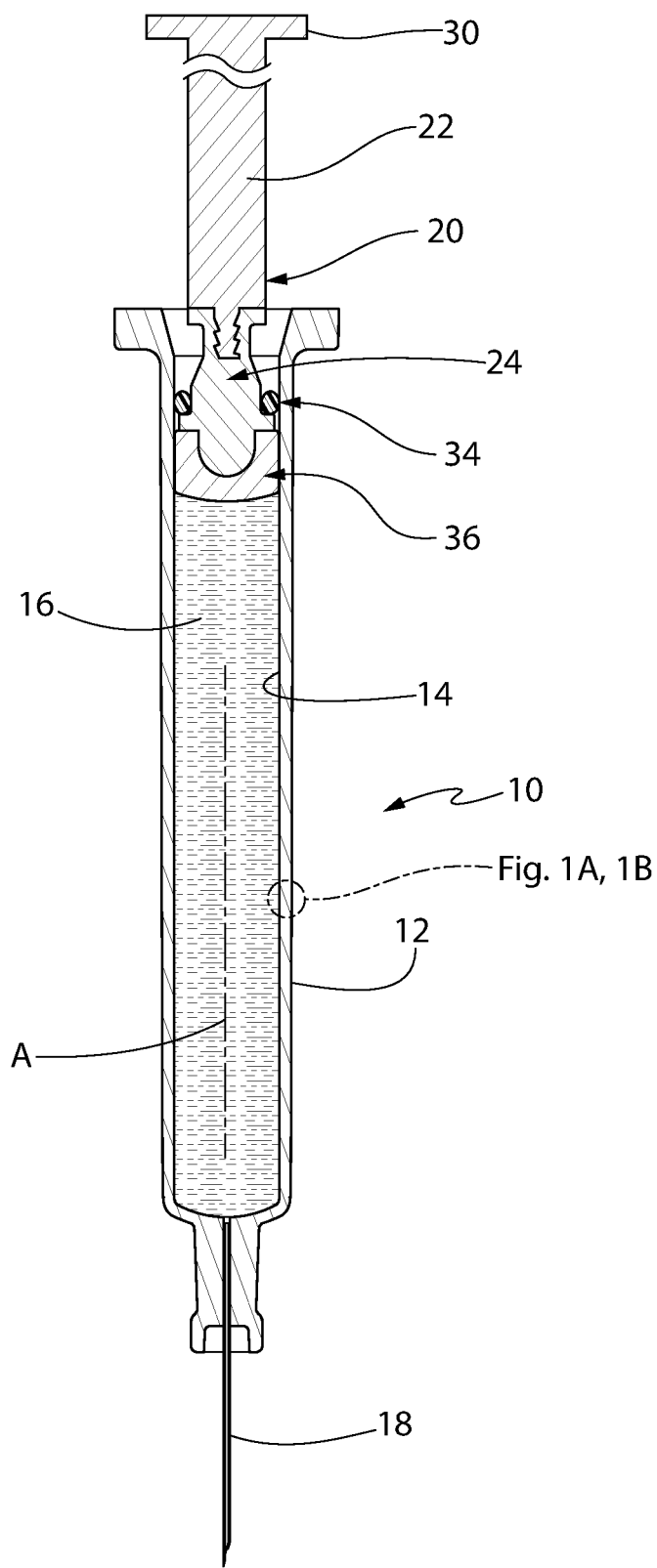
FIG. 1 is an axial sectional view of one exemplary syringe constructed in accordance with this invention.

The present invention will now be described more fully with reference to the accompanying drawings, in which several embodiments are shown. This invention may, however, be embodied in many different forms and should not be construed as limited to the embodiments set forth here. Rather, these embodiments are examples of the invention, which has the full scope indicated by the language of the claims. Like numbers refer to like elements throughout.

Definitions

For purposes of the present invention, an "organosilicon precursor" is a compound having at least one of the linkages:

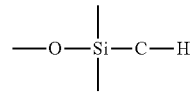

or

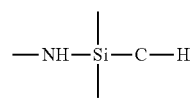

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a plasma enhanced chemical vapor deposition (PECVD) apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

Values of w, x, y, and z are applicable to the empirical composition $Si_wO_xC_yH_z$ throughout this specification. The values of w, x, y, and z used throughout this specification should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$. Also, although $SiO_xC_yH_z$ is described as equivalent to $SiO_xC_y$, it is not necessary to show the presence of hydrogen in any proportion to show the presence of $SiO_xC_y$.

The term "barrel" refers to a medical barrel, as may be used, e.g., as part of a medical device for containing and dispensing liquid product, such as a syringe.

The terms "plunger" or "plunger assembly" when used with reference to any embodiment of the present invention (as opposed to with reference to conventional plungers in the art) refers to a convertible plunger according to the present invention.

"Frictional resistance" can be static frictional resistance and/or kinetic frictional resistance.

The "plunger sliding force" (synonym to "glide force," "maintenance force", or $F_m$, also used in this description) in the context of the present invention is the force required to maintain movement of a plunger tip in a syringe barrel, for example during aspiration or dispense. It can advantageously be determined using the ISO 7886-1:1993 test known in the art. A synonym for "plunger sliding force" often used in the art is "plunger force" or "pushing force".

The "plunger breakout force" (synonym to "breakout force", "break loose force", "initiation force", $F_i$, also used in this description) in the context of the present invention is the force required to initiate movement of the plunger tip in a syringe, for example in a prefilled syringe.

Both "plunger sliding force" and "plunger breakout force" and methods for their measurement are described in more detail in subsequent parts of this description. These two forces can be expressed in N, lbs or kg and all three units are used herein. These units correlate as follows: 1N=0.102 kg=0.2248 lbs (pounds).

"Slidably" means that the plunger tip, closure, storage ring, convertible plunger or other removable part is permitted to slide axially, e.g. in a medical barrel.

"Container closure integrity" or "CCI" refers to the ability of a container closure system, e.g., a plunger disposed in a prefilled syringe barrel, to provide protection and maintain efficacy and sterility during the shelf life of a sterile product contained in the container.

The term "outward radial pressure," as used with respect to a plunger according to the invention or elements thereof, refers to pressure applied or exerted in a direction outward from (or away from) the plunger's central axis.

The term "syringe" is broadly defined to include cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents. Optionally, "syringe" may include prefilled syringes. A "syringe" as used herein may also apply to vaccine dispensing syringes comprising a product space containing a vaccine. A "syringe" as used herein may also have applications in diagnostics, e.g., a sampling device comprising a medical barrel prefilled with a diagnostic agent (e.g., contrast dye) or the like. Broadly, a "syringe" as used herein is shorthand for any medical barrel, which when assembled with one or more other components (e.g. a plunger), functions as a container/dispenser of flowable product.

One or two openings, like the openings of a sample tube or vial (one opening) or a syringe barrel (two openings) are preferred. If the vessel has two or more openings, they can be of same or different size.

Though the invention is not necessarily limited to syringes of a particular volume, syringes are contemplated in which the lumen has a void volume of, for example, from 0.5 to 50 mL, optionally from 1 to 10 mL, optionally from 0.5 to 5 mL, optionally from 1 to 3 mL.

"PECVD" refers to plasma enhanced chemical vapor deposition.

A "lubricant" is a material or substance introduced to reduce friction between surfaces in mutual contact. A "flowable lubricant" is a lubricant that is deposited on a surface as a fluid (liquid or vapor). This definition encompasses such lubricants that are not treated or modified upon or after deposition, e.g., PDMS or silicone oil, in liquid form, applied to a surface. This definition also encompasses a liquid or vapor applied lubricant that is condensed, crosslinked, plasma-treated, reacted, heated, irradiated, or otherwise treated or modified upon deposition or subsequent to deposition. A common characteristic of flowable lubricants is that they tend to generate particles, e.g., in the form of droplets or micelles.

References to "pharmaceutical agent," "pharmaceutically active," "pharmaceutical," "drug," "medicament," "active agent," "active drug," "drug product" and the like, refer in a general sense to substances useful in the medical and scientific arts as suitable for delivery via a syringe, including, for example, drugs, biologics, diagnostic agents (e.g., dyes or contrast agents) or other substances used for therapeutic, diagnostic, or preventative (e.g., vaccines), or research purposes. Example pharmaceutical agents or drug products include biologics, vaccines, chemotherapeutic agents, contrast agents, small molecules, immunogens, antigens, interferons, polyclonal antibody preparations, monoclonal antibodies, anesthetics, interfering RNAs, gene vectors, insulins, or combinations of any of these. "Inactive" substances refer to carriers, excipients, diluents, and the like, which are well-known in the art, although such substances may have beneficial function in the mixed injectable, such as, for example, adjuvants, isotonic or buffering agents. These active or inactive substances may also include substances having immediate, delayed or sustained release characteristics. It is contemplated that "drug products" may broadly include active and inactive substances configured for storage and injection by a syringe.

Syringe Barrel Materials

Optionally, syringes according to any embodiment of the present invention may be made from one or more injection moldable thermoplastic materials including, but not limited to: an olefin polymer; polypropylene (PP); polyethylene (PE); cyclic olefin copolymer (COC); cyclic olefin polymer (COP); polymethylpentene; polyester; polyethylene terephthalate; polyethylene naphthalate; polybutylene terephthalate (PBT); PVdC (polyvinylidene chloride); polyvinyl chloride (PVC); polycarbonate; polymethylmethacrylate; polylactic acid; polylactic acid; polystyrene; hydrogenated polystyrene; poly(cyclohexylethylene) (PCHE); nylon; polyurethane polyacrylonitrile; polyacrylonitrile (PAN); an ionomeric resin; Surlyn® ionomeric resin. For applications in which clear and glass-like polymers are desired (e.g., for syringes and vials), a cyclic olefin polymer (COP), cyclic olefin copolymer (COC) or polycarbonate may be preferred. Such materials may be manufactured, e.g., by injection molding or injection stretch blow molding, to very tight and precise tolerances (generally much tighter than achievable with glass). Alternatively, syringes according to embodiments of the present invention may be made from glass.

Syringe and Convertible Plunger Embodiments

In FIG. 1, one exemplary embodiment of a syringe 10 including a plunger assembly 20 constructed in accordance with one aspect of this invention is shown. As a brief aside, the terms "distal" and "proximal" are used throughout this specification. The terms "distal" and "proximal" refer generally to a spatial or positional relationship relative to a given reference point, wherein "proximal" is a location at or comparatively closer to that reference point and "distal" is a location further from that reference point. As applied herein to syringe barrels, for example, the relevant reference point is the back end of the barrel (for example, the flange at the top of the barrel 12 as shown in FIG. 1), near where the plunger rod 22 and the convertible plunger 24 are joined. The distal end is at the bottom or dispensing end of the barrel 12, where the needle 18 is mounted. "Proximal" and "distal" may also be used to refer to the direction of application of force. For example, the pushing force to dispense syringe contents would be applied in a "distal direction" or "distally," i.e., a force pushing the plunger head 30 down in FIG. 1 to advance the liquid sealing section 36 down toward the dispensing end or distal end of the syringe.

The syringe 10 is of generally conventional construction and includes a hollow barrel 12 having a central longitudinal axis A. The barrel has an inner surface 14 and is configured to hold an injectable liquid 16 therein. A needle 18 is located at the distal end of the barrel and is in fluid communication therewith. The plunger assembly 20 is disposed so that a distal portion of it is located in the proximally located portion of the barrel, like shown in FIG. 1, whereupon the syringe 10 is ready for use. To that end, when the plunger assembly 20 is actuated, e.g., pushed in the distal direction, it forces the injectable liquid within the barrel out through the needle 18.

The plunger assembly 20 basically comprises a plunger rod 22 and a convertible plunger 24. The convertible plunger 24 constitutes a subassembly of components which are configured to provide sufficient compressive force against the inner surface of the sidewall of a prefilled syringe or cartridge barrel to effectively seal and preserve the shelf-life of the contents of the barrel during storage. When a convertible plunger, such as that of the subject invention, provides container closure integrity (CCI) and gas-tight sealing (e.g., providing a barrier to oxygen, moisture and/or optionally additional gases), adequate to effectively seal and preserve the shelf-life of the contents of the barrel during storage, the convertible plunger (or at least a portion of its exterior surface) may alternatively be characterized as being in an "expanded state" or "storage mode." The expanded state or storage mode may be a product of, for example, an expanded outer diameter or profile of at least a portion of the syringe barrel-contacting surface of the plunger and/or the normal force that the plunger exerts on the inner wall of the syringe barrel in which it is disposed. The convertible plunger (or at least a portion of its exterior surface) is reducible to what may alternatively be characterized as a "constricted state" or a "dispensing mode," wherein the compressive force against the sidewall of the barrel is reduced or eliminated in part, allowing a user to more easily advance the plunger in the barrel and thus dispense the contents of the syringe or cartridge. The constricted state or dispensing mode may be a product of, for example, a reduced outer diameter or cross-sectional width (relative to that of the expanded state) of at least a portion of the syringe barrel-contacting surface of the plunger and/or reduced normal force against the inner wall of the syringe barrel exerted by the plunger and/or reduced resistance to inward radial compression.

As used herein, the term "convertible plunger" broadly includes a plunger, configured for use in a medical barrel, wherein the plunger is convertible from a storage mode to a dispensing mode, as generally described above. This specification focuses primarily (albeit not exclusively) on convertible plunger embodiments having a liquid sealing section that translates axially in a medical barrel, independently of a separate storage sealing section component, when the plunger transitions from storage mode to dispensing mode (for short, "independent storage sealing section plunger"). An alternative type of convertible plunger, which is the subject of applications assigned to the same assignee as the present Application, is optionally described as having an insert positioned within a cavity of the plunger sleeve to provide outward radial pressure of an adjacent storage sealing section against a medical barrel wall (to provide a storage mode). The insert, which is preferably more rigid than the plunger sleeve, is then movable to a different cavity (e.g., a cavity that is distal to the storage cavity) within the plunger sleeve to release such radial compression and thus transition the plunger to a dispensing mode. Such "insert and sleeve" plungers are described in PCT Publication No. WO 2015/054282, which is incorporated by reference herein in its entirety. While insert and sleeve plungers are not the primary focus of the present application, some embodiments are described herein particularly to illustrate methods and apparatus, according to aspects of the invention, for assembling such plungers into medical barrels. It should be understood, moreover, that the invention, in one aspect, may cover at least both independent storage sealing section and insert and sleeve types of convertible plungers.

Features common to both the independent storage sealing section type of plunger and insert and sleeve type of plunger are as follows. Generally speaking, they both comprise an internal portion and a generally cylindrical exterior surface that surrounds at least part of the internal portion. The generally cylindrical exterior surface includes a compressible and resilient storage sealing section (optionally an elastomer) that is maintained in an expanded state by outward radial pressure provided by the internal portion. The internal portion is comparatively more rigid than the storage sealing section. The expanded state is reducible to a constricted state by an operation that is applied to the internal portion of the plunger to reduce or eliminate the outward radial pressure. The storage sealing section, in the constricted state, has a reduced maximum diameter or cross-sectional width than the storage sealing section in the expanded state and/or is less resistant to inward radial compression compared to the storage sealing section in the expanded state. With the insert and sleeve type plunger, the internal portion comprises the insert and storage sealing section is the portion of the sleeve surrounding and adjacent to the insert. With the independent storage sealing section plunger type, the internal portion is the ring carrier and the storage sealing section is on the storage ring. In both cases, the plungers are preferably actuated by applying a force to the plungers in a distal direction. Such actuation force may apply the aforementioned operation to the internal portion of the plunger. In the case of the insert and sleeve type plunger, the operation may displace the insert from a proximal cavity to a distal cavity in the sleeve. In the case of the independent storage sealing section plunger type, the operation includes axial displacement of the ring carrier relative to the storage ring when transitioning from storage mode to dispensing mode.

Accordingly, in one aspect, as shown in FIGS. 1 and 2A-3B, the invention is a convertible plunger 24 comprising a central core 32 having a longitudinal axis which is coaxial with the central axis A of the barrel 12, a storage sealing section 34 and a liquid sealing section 36. The central core 32 is preferably rigid, optionally made from a polymer material. The storage sealing section 34 and the liquid sealing section 36 each have a respective generally cylindrical exterior surface. As used herein, a "generally cylindrical" exterior surface may include minor interruptions or variations in geometry (e.g., due to ribs, valleys, etc.) to the otherwise cylindrical shape of the external surface of a given component, e.g., the liquid sealing section. As will be described in detail later, the generally cylindrical exterior surface of the storage sealing section includes one or more annular ribs or outwardly projecting surfaces for engagement with the inner wall of the syringe barrel when the storage sealing section is in its expanded state. The expanded state is reducible to a constricted state by the relative movement of the storage sealing section along the longitudinal axis A with respect to the liquid sealing section or vice versa. As used herein, "expanded state" and "constricted state" may refer to comparative dimensional measurements (e.g., expanded state being wider than constricted state) and/or comparative resistance to inward compression of the plunger (the "expanded state" being more resistant to inward compression and the "constricted state" being less resistant to inward compression) and/or comparative outward radial pressure exerted by at least a portion of the plunger's exterior surface (the plunger's exterior surface in the "expanded state" exerting more outward radial pressure and in the "constricted state" exerting less outward radial pressure).

The convertible plunger 24, preferably at a proximal end of the central core 32, is mounted on a distal end of the plunger rod 22. The plunger rod 22 is an elongated member having a central longitudinal axis extending coaxially with the central axis A of the barrel of the syringe. The distal end of the plunger rod is optionally in the form of a threaded projection 26 (FIG. 2A) extending distally from the distal end of the rod 22 and centered on the axis A. The threaded projection 26 is configured to be threadedly received within a mating threaded bore or hole 28 in the proximal end of the convertible plunger 24 to mount the convertible plunger on the distal end of the plunger rod 22. Alternatively, the plunger 24 may be mounted to the distal end of the plunger rod 22 through other means, such as by snap fit or press fit. The proximal end of the plunger rod 22 is in the form of an enlarged flanged head 30 (FIG. 1), which is configured to be pressed by a user to eject the liquid 18 from the syringe.

The convertible plunger 24 is configured for operating in two modes. One mode is a sealing mode, like shown in FIGS. 1 and 2A, in which the storage sealing section 34 of the plunger is in its "engagement" position wherein it is compressed between a first portion of the central core of the plunger and the internal wall of the syringe's barrel to form a gas-tight, liquid-tight and CCI level interface therebetween. The other mode is a gliding mode in which the storage sealing section is shifted to a different portion on the central core, e.g., a "release" position, when the plunger assembly is slid in the barrel so that the storage sealing section is no longer in engagement (or is in reduced engagement) with the internal wall of the barrel. However, in the gliding mode the liquid sealing section of the plunger will be in sliding engagement with the internal wall of the barrel to form a liquid-tight interface therebetween. Moreover, owing to the inherent lubricity of liquid sealing section, no liquid or other flowable lubricants (e.g., silicone oil) are necessary to be used between the plunger and the barrel to facilitate sliding of the plunger in the barrel. This feature constitutes a considerable advantage over the prior art, since the use of a flowable lubricant between the plunger and the barrel to facilitate sliding of the plunger may have the effect of contaminating the injectable liquid if the lubricant disassociates from the syringe or plunger into that liquid. The liquid sealing section itself, in addition to providing a liquid tight seal, preferably also provides a CCI-level seal, to comply with prevailing industry concerns and to provide CCI redundancy with the storage sealing section.

Figure 2A:
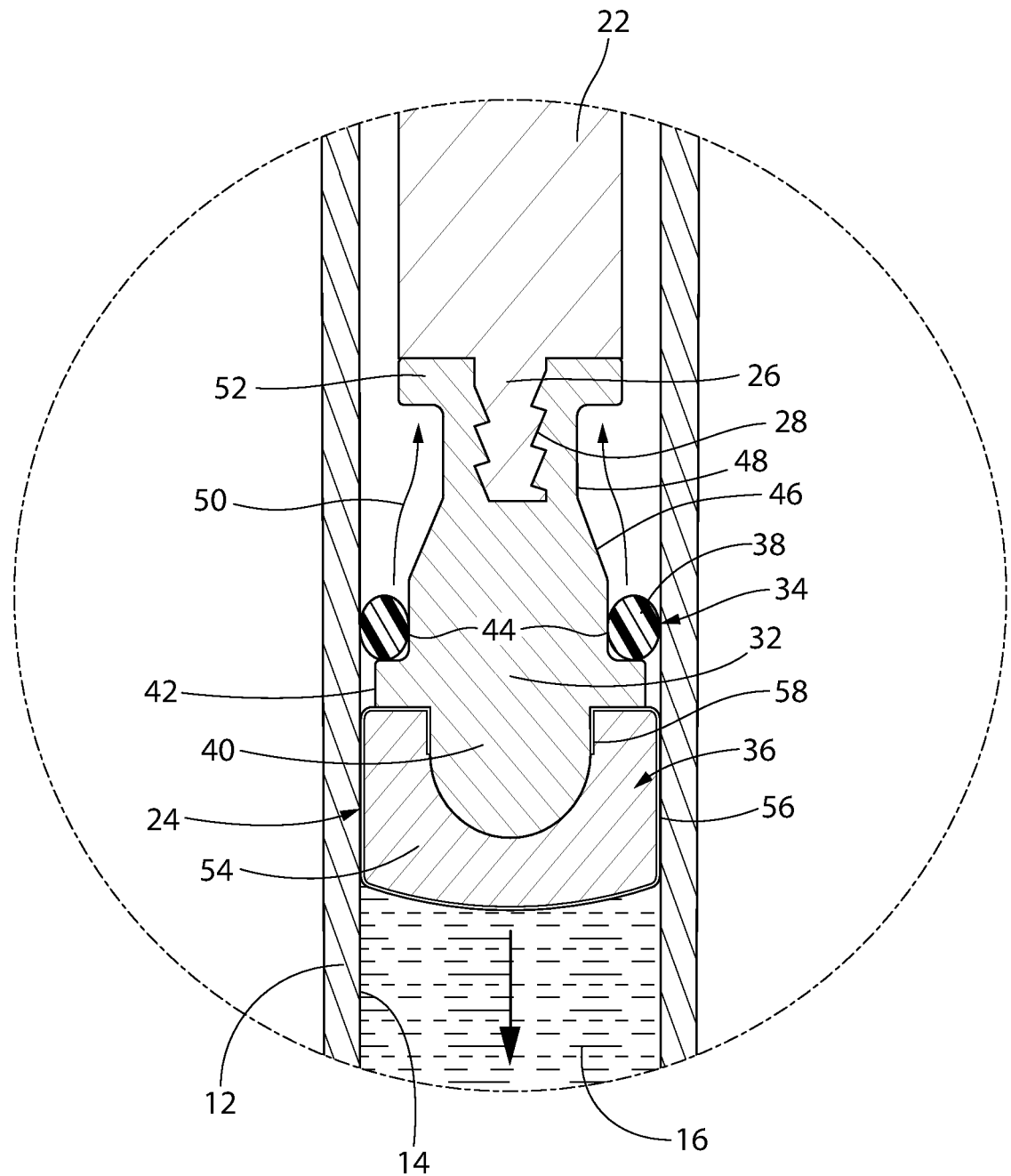
FIG. 2A is an enlarged axial sectional view of a portion of a convertible plunger forming a portion of the syringe shown in FIG. 1, with the plunger being shown in its engagement position in the syringe, wherein its storage sealing section forms a liquid-tight and gas-tight interface with the interior wall of the syringe and its liquid sealing section forms a liquid-tight interface and preferably a CCI seal with the interior wall of the syringe.
Figure 2B:
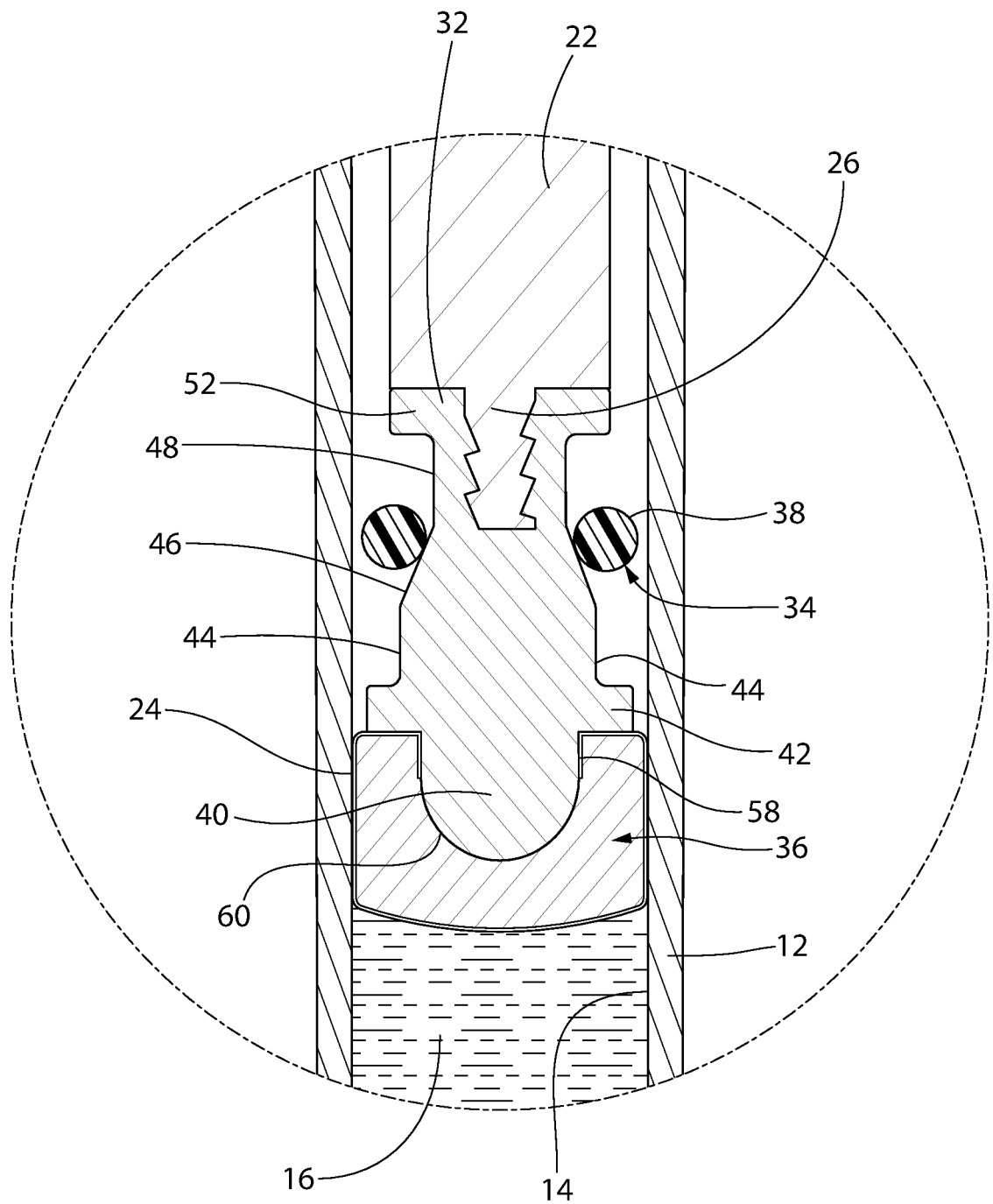
FIG. 2B is an enlarged sectional view, similar to FIG. 2A, but showing the convertible plunger as it is moved from its engagement position to a release position wherein its storage sealing section no longer forms a liquid-tight and gas-tight interface with the interior wall of the syringe but its liquid sealing section still forms a liquid-tight interface and preferably CCI seal with the interior wall of the syringe.
Figure 2C:
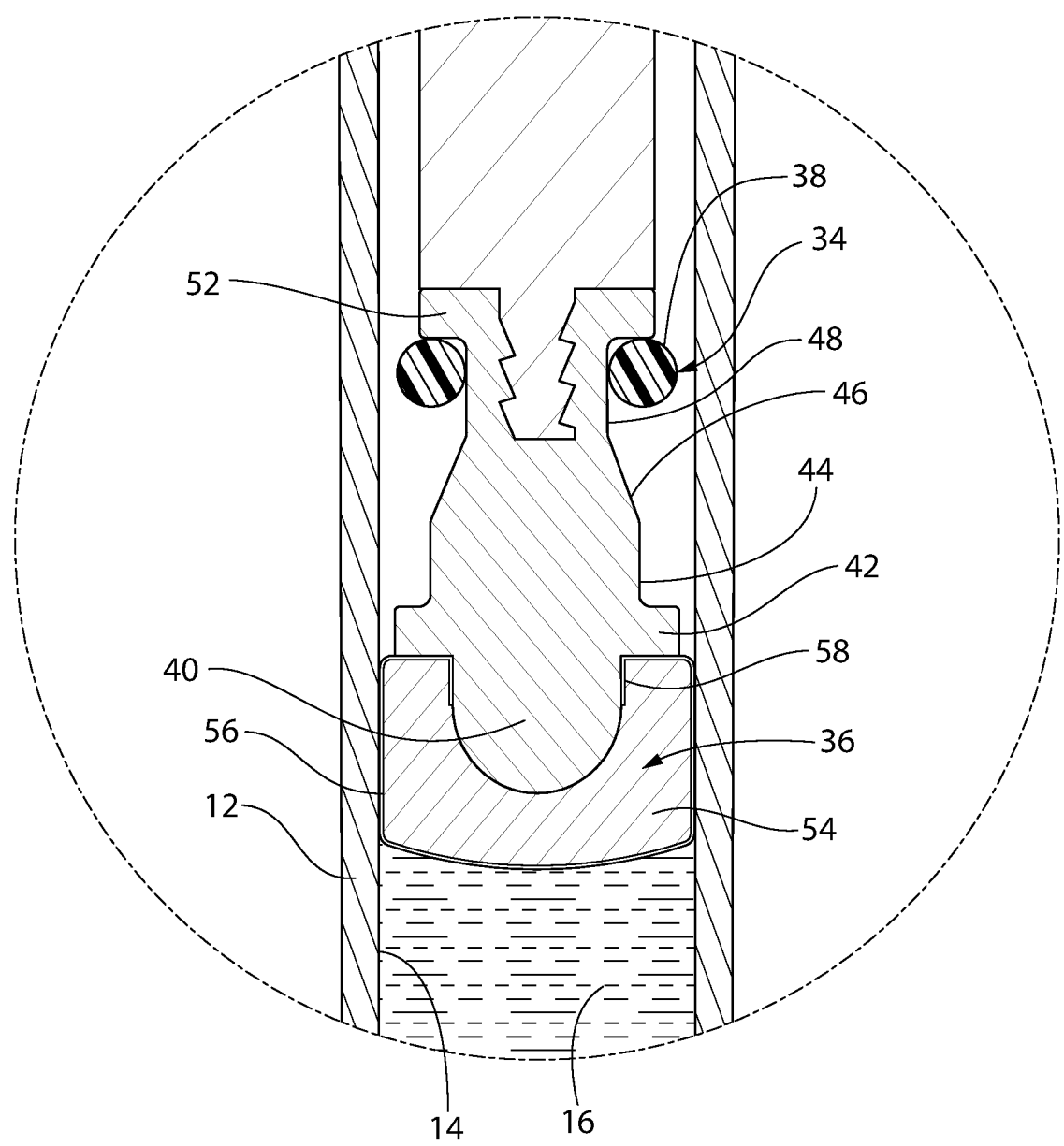
FIG. 2C is an enlarged sectional view similar to FIGS. 2A and 2B but showing the convertible plunger in its most fully released position.

As best seen in FIGS. 2A-2C, the liquid sealing section 36 is mounted on the distal end of the plunger's central core 32, while the storage sealing section 34 is located proximally of the liquid sealing section. The storage sealing section 34 is in the form of at least one ring mounted around a portion of the central core and configured so that when the plunger assembly is in the engagement position like shown in FIGS. 1 and 2A, the at least one ring of the storage sealing section 34 forms the heretofore mentioned liquid-tight and gas-tight interface with the interior wall 14 of the syringe's barrel 12. Thus, when the plunger assembly is in that position the storage sealing section provides CCI and a gas-tight seal for the syringe. In the exemplary embodiment shown in FIG. 1 the storage sealing section is in the form of a single "O-ring" 38 of circular cross-section. Other single rings of various cross-sectional shapes may be provided to form the storage sealing section. In fact, multiple rings of various cross-sectional shapes may be provided to form the storage sealing section. For example, optionally, the O-ring has more than one rib or lobe; e.g., 2 ribbed or 3 ribbed O-rings are contemplated. Some of those alternative embodiments for the storage sealing section are discussed below.

The central core 32 of the convertible plunger 24 is an elongated rigid member, optionally having a cylindrically shaped mounting projection 40 at the distal end thereof. The projection 40 can be of any suitable shape. In the exemplary embodiment shown it is semi-spherical. The projection 40 serves as the means for mounting the liquid sealing section 36 on the distal end of the central core 32. A flange 42 projects radially outward from the central core immediately proximally of the projection 40. An annular storage platform 44 is provided on the central core 32 immediately proximally of the flange 42. The storage platform 44 is configured to receive and hold the at least one ring 38 thereon in a "holding" position when the plunger assembly 24 is in the storage mode, i.e., the state shown in FIG. 1.

The ring 38 is formed of a resilient material or one or more resilient materials, including, but not limited to, a thermoset rubber (e.g., butyl rubber), a thermoplastic elastomer (TPE), liquid silicone rubber and fluoro-liquid silicone rubber. The diameter of the central core 32 at the location of the storage platform 44 is greater than the normal internal diameter of the ring 38. Thus, when the ring 38 is disposed around the storage platform 44 it is stretched from its normal outer diameter (i.e., its "constricted" state) to its "expanded" state. In that expanded state the outermost portion of the periphery of the ring will be in intimate engagement with the inner surface 14 of the barrel, thereby forming the heretofore mentioned gas-tight, CCI-tight and liquid-tight interface therebetween. As should be appreciated by those skilled in the art, when the ring 38 is in such engagement with the inner surface of the barrel "sticktion," can result. Thus, the convertible plunger of this invention is constructed to enable the central core 32 to move with respect to the ring 38 (which initially adheres to the barrel through sticktion) to enable the plunger assembly 24 to be moved to the release position wherein it operates in the heretofore mentioned gliding mode. When in that mode, the ring 38 will be in a constricted state, wherein the outside diameter of the ring is optionally less than the inner diameter of the interior surface 14 of the barrel's wall 12 so that the ring does not engage that interior surface and hence will not interfere with the sliding movement of the plunger assembly into the barrel.

In order to enable the O-ring 38 to move from its engagement position (wherein it will be retained about the storage platform 44) to the release position (wherein it is transitioned from the storage platform 44), the central core 32 includes a conically tapering section 46 located immediately adjacent the storage platform 44. The proximal end of the conically tapering section 46 terminates in a cylindrical section 48, the external diameter of which is less than the external diameter of the storage platform 44. Thus, when the plunger assembly 20 is pressed to cause it to move in the distal direction (i.e., applying an operation to the internal portion of the plunger comprising application of an actuation force on the plunger in the distal direction) shown by the arrow in FIG. 2A within the barrel 12, the frictional engagement between the O-ring and the inner wall of the barrel will tend to hold the O-ring at that longitudinal position in the barrel, while the central core 32 moves distally. In other words, the O-ring 38 preferentially adheres to the inner surface 14 of the barrel over the outer surface of the central core 32. Thus, there will be relative movement between the O-ring 38 and the central core 32 in the axial direction. That relative axial movement causes the O-ring 38 to move from its holding position about the storage platform 44, so the O-ring slides in the proximal direction with respect to the central core 32 in the direction of the arrows 50 in FIG. 2A, whereupon the radially outer-most surface of the O-ring will no longer be in engagement (or optionally will be in reduced engagement or apply reduced outward radial pressure) with inner surface 14 of the barrel. As such, the plunger assembly 20 can be slid smoothly down the barrel with minimal force. Continued pressing of the plunger assembly distally will ultimately bring the O-ring into engagement with the under-surface of a projecting flange 52 forming the proximal end of the central core 32, such as shown in FIG. 2C.

As mentioned above, when the plunger assembly 20 is in the glide mode, the liquid sealing section 36 will be in sliding engagement with the inner surface 14 of the barrel to result in a good liquid-tight interface therebetween. To that end, the liquid sealing section 36 basically comprises an elastomeric body or head 54 having an exterior surface portion having a lubricity that is greater than the lubricity of the interior wall 14. The first surface portion may be in the form of a film 56 which extends about the entire exterior surface of the head 54. The film may have an optional thickness in any embodiment of under approximately 100 micrometer (μm), optionally from 25-50 μm. A variety of different materials may be employed for the film, such as, for example, an inert fluoropolymer, including, fluorinated ethylene propylene (FEP), ethylene tetrafluoroethylene (ETFE), polytetrafluoroethylene (PTFE), ethylene perfluoroethylenepropylene (EFEP), ethylene chlorotrifluoroethylene (ECTFE), Polychlorotrifluoroethene (PCTFE), perfluoroalkoxy (PFA), among other coatings. Optionally, CPT fluoropolymer may be used. CPT is a modified perfluoroalkoxy (PFA) commercially available from Daikin America, Inc. and generally comprises the addition of PCTFE side chains to a PFA main chain during polymerization, thereby increasing gas and/or liquid barrier properties of standard PFA. Optionally, the exterior surface of the head 54 may be in the form of a rigid cap (not shown) formed of a perfluoropolyether oil, such as DEMNUM which is commercially available from Daikin America, Inc., which may be mixed with resin and extruded into a film, mold or cap. Additionally, according to certain embodiments, the material used for the film coating may not be an expanded fluoropolymer. Further, according to certain embodiments, additives may be added to the material for the film or cap, such as additives that may improve the adhesion of the film or cap to the underlying portion of the plunger making up the liquid sealing section and/or decrease the friction between that section and the sidewall of the barrel. Additionally, according to certain embodiments, an adhesion promoting coating or process may be employed, such as, for example, a corona treatment. For some applications, it may be desirable to coextrude different materials to form the film. For example, coextruded film combinations may include a cyclic olefin copolymer (COC) with Aclar, Polyethylene (PE) with Aclar and FEP with PE, among other combinations.

Optionally, after the film material has been inserted into the mold, the plunger material is injected into the mold. Thus, in the final product, the liquid sealing section of the plunger may comprise a plunger core, a polymer head disposed on the tip of the plunger core and a film covering the head. Alternatively, a high durometer, lubricious TPE material without any film disposed thereon may be used as the liquid sealing section.

Figure 3A:
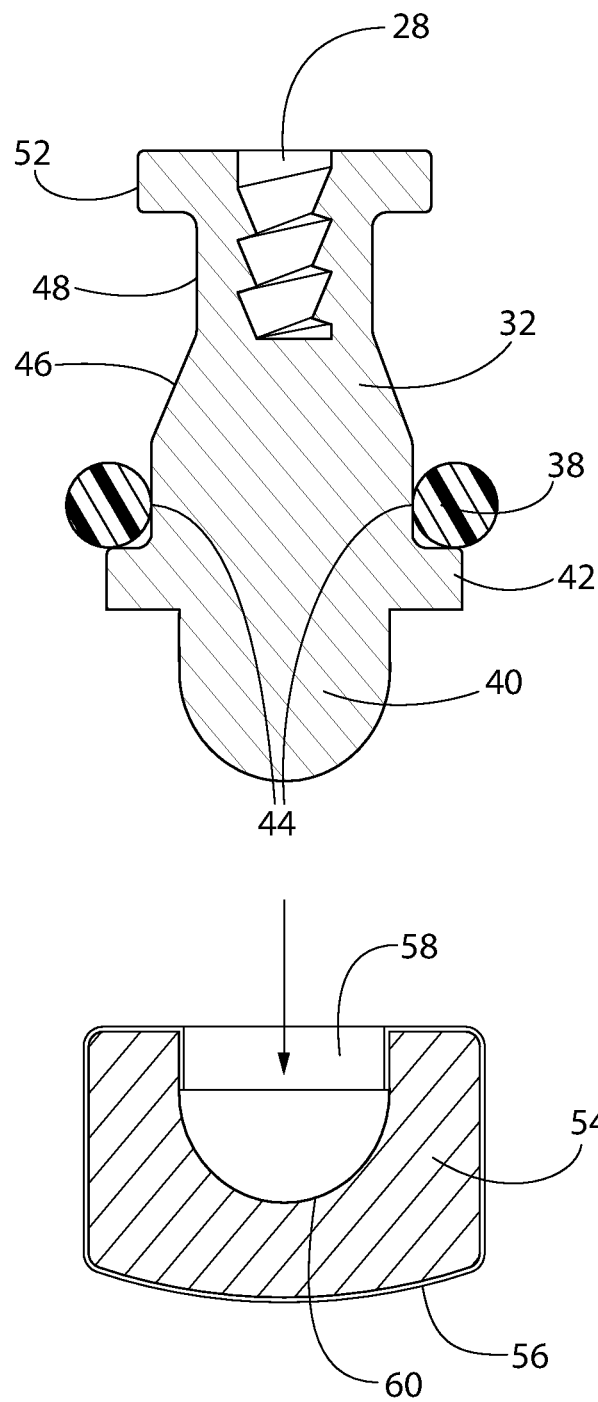
FIG. 3A is an enlarged, exploded, axial sectional view of the exemplary embodiment of the convertible plunger of FIG. 1 in the process of being assembled.
Figure 3B:
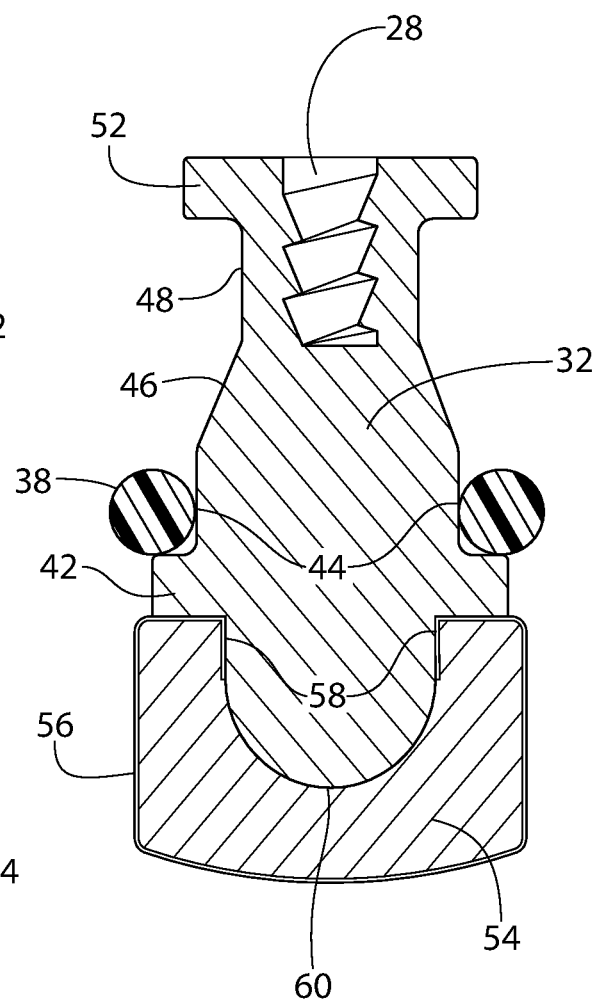
FIG. 3B is an enlarged axial sectional view of the exemplary embodiment of the convertible plunger of FIG. 3A but shown after it has been assembled.

In the case where a film 56 is used to provide the lubricious outer surface of the liquid sealing section, the film may be secured to the head 54 in various ways. For example, as shown in FIG. 3A a sheet of film 56 may be wrapped about the head 54, so that the portions 58 of the sheet of film contiguous with its edges are located within a recess 60 in the head 54, like shown in FIGS. 2A-2C and 3A. The recess 60 is of a mating shape to the shape of the projection 40. Thus, when the projection 40 is inserted into the recess to mount the head 54 on the distal end of the central core 32, the edge portions 58 of the film 56 will be trapped therein. The securement of the head 54 to the central core 32 can be achieved by means of a press fit, compression ribs, or any other suitable means for fixedly securing the head to the central core with the edge portions of the film trapped therebetween.

FIGS. 4A and 4B illustrate another convertible plunger 124 constructed in accordance with this invention. The plunger 124 basically comprises a cylindrical central core 132 having a distal end 135 to which a head 154 is fixedly secured. The head 154 is similar to the head 54 and serves to form a portion of the liquid sealing section 136 of this embodiment. A sheet of film 156, similar to the film 56 described above is wrapped about the head 154, with the portions of the film at its edges being trapped between the core 132 and a cylindrical sleeve 160. The sleeve 160 is an elongated rigid tubular member, the inside diameter of which is just slightly larger than the outside diameter of the central core 132. The inner surface of the sleeve at its distal end includes an annular inner recess 162. The outer surface of the sleeve at its distal end includes an annular storage platform 144. The inner recess 162 is configured to receive and trap the edge portions of the film 156. The storage platform 144 is similar in function to the storage platform 44, i.e., it is arranged to receive and hold the storage sealing section 134 of the convertible plunger 124 when the plunger 124 is in storage mode. That storage sealing section 134 comprises a ring 138 formed of a similar material as the O-ring 38, but the ring 138 has a generally rectangular cross-section with a slightly concave outer surface 140. The top and bottom edges of the outer surface 140 of the ring 138 are in the form of a pair of annular ribs 142, each of which forms an engagement surface to tightly engage the inner surface of the barrel when a plunger assembly composed of the convertible plunger 124 is located within the barrel 12 of the syringe in the engagement position. That engagement results in a good gas-tight and liquid-tight interface between the ring 138 and the inner surface of the barrel.

The ring 138, like the O-ring 38, is arranged to be moved from the engagement position to the release position, whereupon it no longer engages the inner surface of the barrel. To that end, the sleeve 160 includes a conically tapering section 146 located immediately proximately of the storage platform 144. The proximal end of the conically tapering section 146 terminates in a cylindrical section 148, the external diameter of which is less than the external diameter of the recess 144. Thus, when the plunger assembly including the convertible plunger 124 is pressed to cause it to move in the distal direction within the barrel 12 of the syringe, the O-ring 138 will move from the storage platform 144 and slide in the proximal direction with respect to the central core, whereupon the ribs 142 of the ring 138 will no longer be in engagement with (or at least will be in reduced engagement with) the inner surface 14 of the barrel. As such, the plunger assembly can be slid smoothly down the barrel with minimal force. The liquid sealing section of the convertible plunger 124 operates in the same manner as discussed with reference to the convertible plunger 24, and hence will not be reiterated in the interest of brevity.

In order to facilitate the assembly of the components making up the convertible plunger 124, the central core 132 includes a plurality of elongated venting grooves or channels 170 extending longitudinally therealong and being equidistantly spaced about the periphery of the central core. The grooves or channels 170 enable any air that would be trapped between the sleeve 160 and the central core 132 when the sleeve is mounted on the central core to exit or vent out the bottom of the sleeve. Alternatively, the venting slots or channels may be provided in the inner surface of the sleeve 160 rather than the outer surface of the central core 132. In fact, the venting slots may be provided in both the inner surface of the sleeve and the outer surface of the central core. In any case, by venting any air between the sleeve and the central core one is able to trap the edge portions of the film 156 between the sleeve and the central core within the inner annular recess 162 expeditiously and neatly.

Still another embodiment of a convertible plunger is shown in FIGS. 5A and 5B and will be discussed now. That convertible plunger is designated by the reference number 224 and is similar in construction to the plunger 24 described heretofore, except for the manner in which the edge portions of the film 56 are trapped with respect to the central core so as not to be exposed. In the interest of brevity those features of the convertible plunger 224 which are common to the convertible plunger 24 will be given the same reference numbers and the details of their construction and operation will not be reiterated. Thus, as can be seen, the convertible plunger 224 includes a central core 32 on which the storage sealing section 34 and the liquid sealing section 36 are mounted. The portions of the film 56 contiguous with the edges thereof are not, however, trapped between the projection 40 and the recess 60 in the head 54. Instead those edge portions are trapped between a retainer ring 162 and the flange 42. The retainer ring is formed by molding it about the edge portions of the sheet of film 56. To that end, a mold member 170 having an annular cavity 172 of generally L-shape in cross-section is disposed about the portion of the central core 32 at the location of the flange 42, with the edge portions of the sheet of film 56 located within the cavity 172. Then any suitable plastic material is injected into the cavity 172 to form the retaining ring 162. Once that has been accomplished the mold member 170 can be removed, leaving the edge portions of the film trapped under the retaining ring and hence not exposed.

Figure 7:
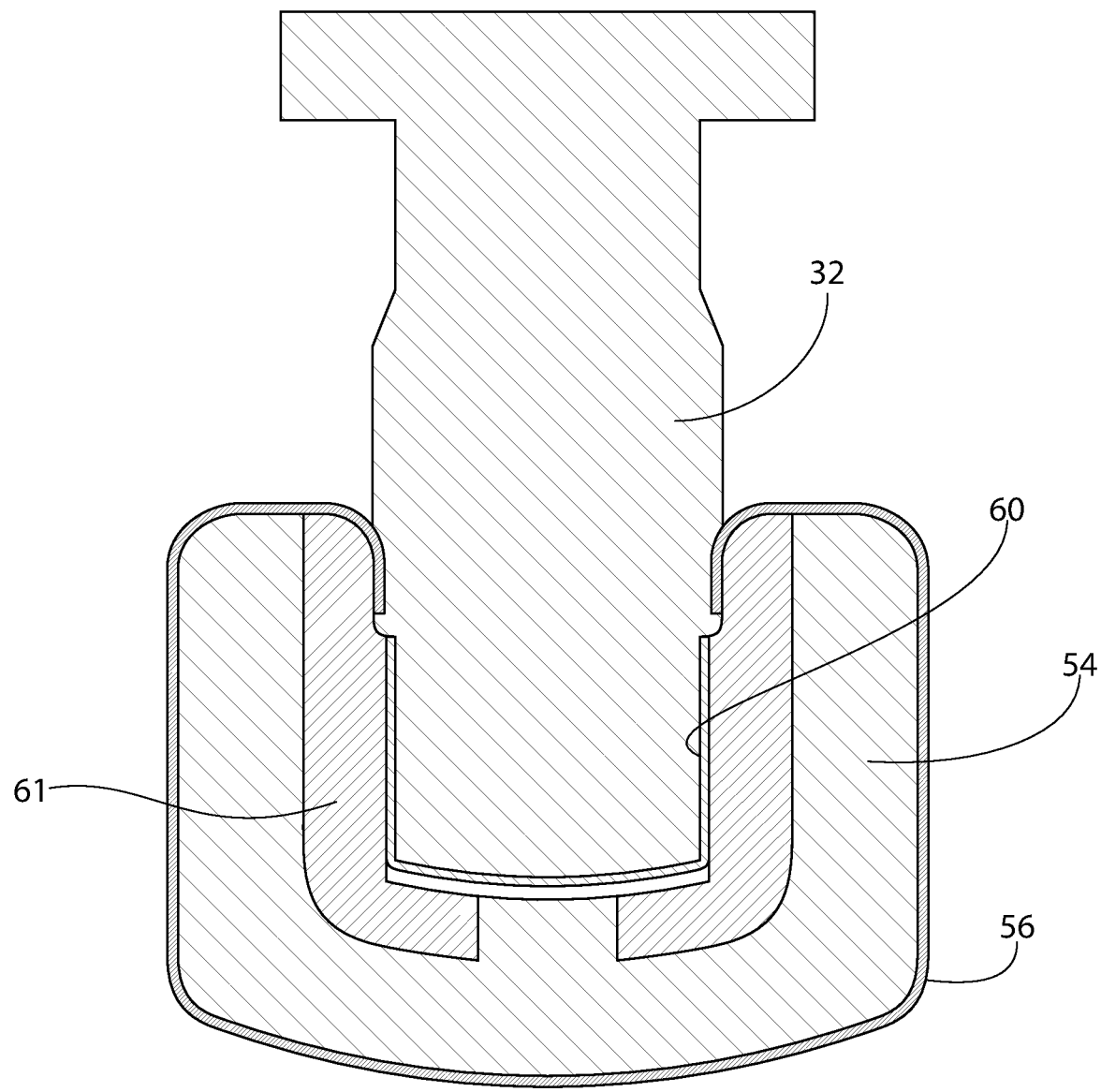
FIG. 7 is an axial sectional view of an exemplary plunger constructed in accordance with this invention, illustrating an optional configuration for applying film thereto.
Figure 8:
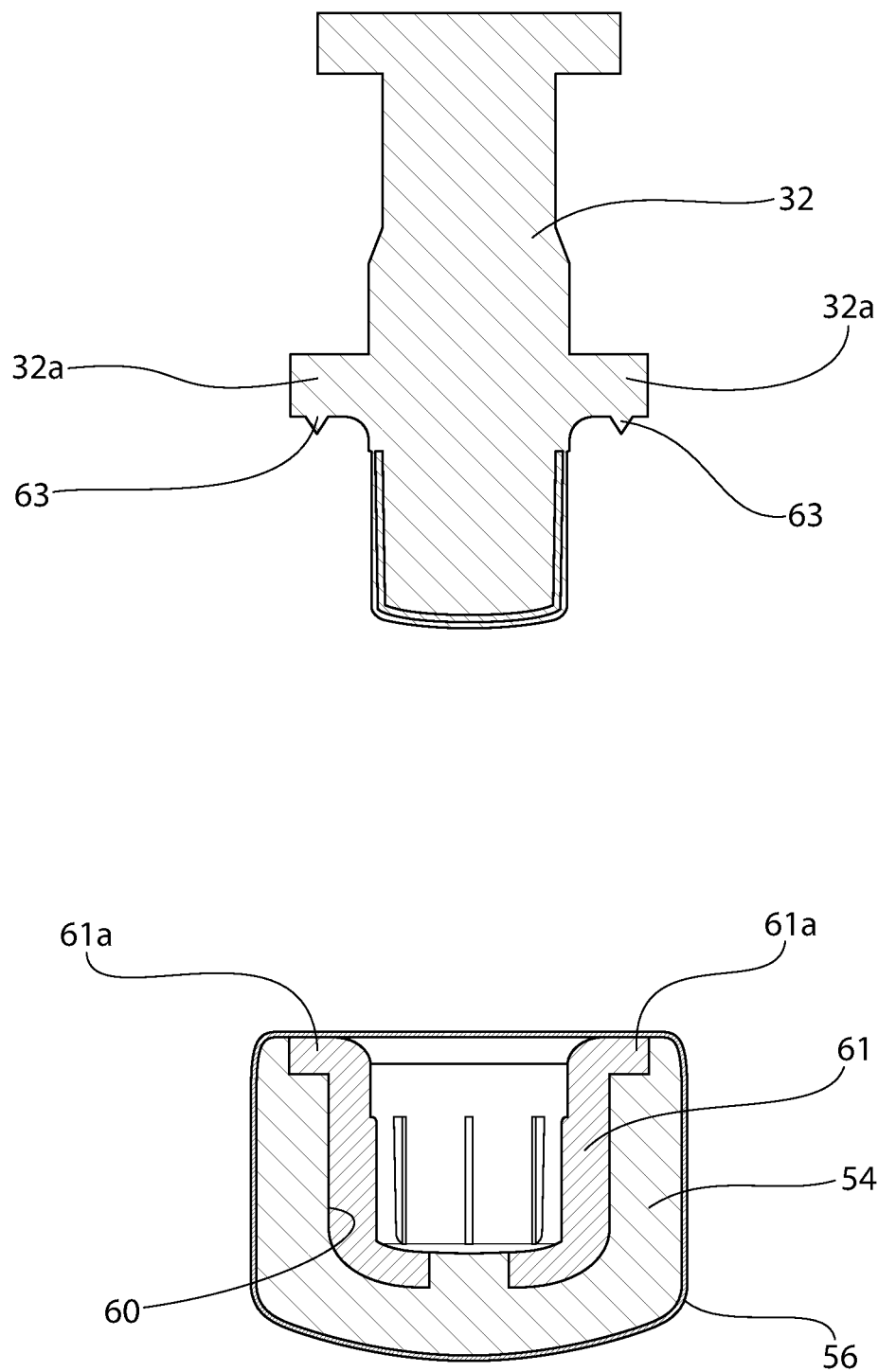
FIG. 8 is an exploded axial sectional view of an exemplary plunger constructed in accordance with this invention, illustrating another optional configuration for applying film thereto.

FIGS. 7-9 show three alternative configurations for applying film to plungers according to any embodiment of the invention. The film in these configurations would function the same as film applied in other configurations disclosed herein; so much of the disclosure elsewhere in the specification suffices for purposes of describing the embodiments of FIGS. 7-9 and will not be repeated, for the sake of brevity. Differences, however, are noted here. To minimize the chances of film wrinkling when wrapping the film 56 about the head 54, the film may be cut into a pattern enabling it to fold neatly into the recess 60 in the head 54. Optionally, a rigid polymer support 61 is disposed within the recess 60 to provide a mating surface with portions of the film 56. As shown in FIG. 7, portions of the film 56 bend into the rigid polymer support 61 and are sandwiched between the core 32 and the rigid polymer support 61. Optionally in any embodiment, the film mates with the rigid polymer support 61 via ultrasonic welding or an adhesive.

In the plunger embodiments shown in FIGS. 8 and 9, the rigid polymer support 61 has an annular rim 61*a* that extends outward towards the outer diameter of the head 54. The core 32 also includes a radially extending annular rim 32*a*. The rims 32*a* and 61*a* are configured to mate to one another. As shown in FIG. 8, the rim 32*a* on the core 32 includes a plurality of radially spaced micro needles 63, adapted to pierce the film 56 section covering the rim 61*a* and stake into the rim 61*a*. Thus, when assembled, the film 56 is sandwiched between the rims 32*a*, 61*a* and secured to the head 54. The configuration in FIG. 9 is similar to that of FIG. 8, except that the rim 32*a* on the core 32 includes a plurality of radially spaced protrusions 63 adapted to mate with a plurality of radially spaced receptacles 65 on the flange 61*a*, thereby securing the film 56 to the head 54. Ribs or grooves can be incorporated on the core or rigid polymer support to provide friction for holding the core and for venting, as described elsewhere in this specification regarding other embodiments. An optional advantage to including a rigid polymer support 61 is that it allows for the option of ultrasonic welding or staking the components.

Figure 10:
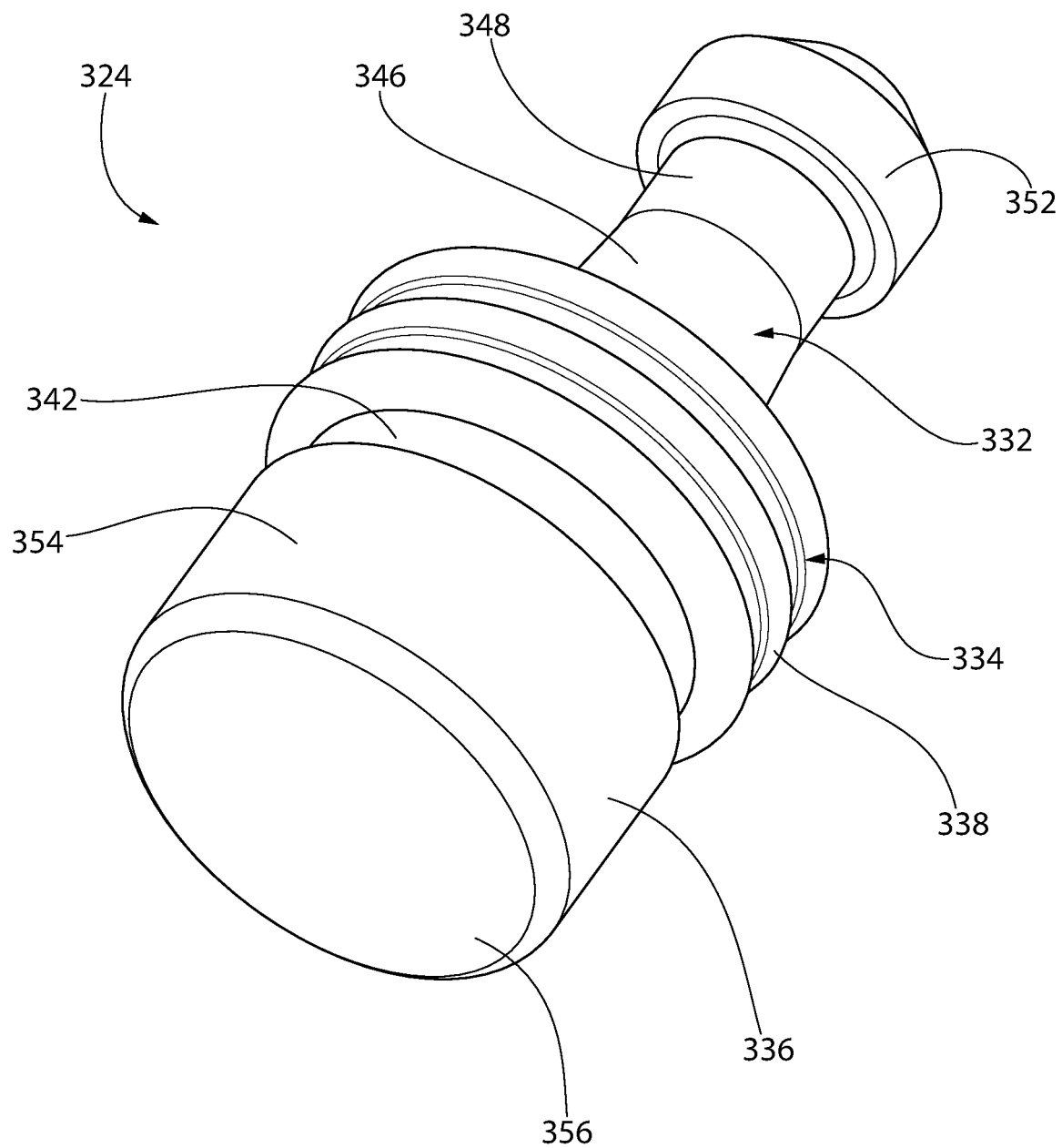
FIG. 10 is a perspective view of an exemplary convertible plunger constructed in accordance with this invention, illustrating a three-ribbed storage sealing section.
Figure 11:
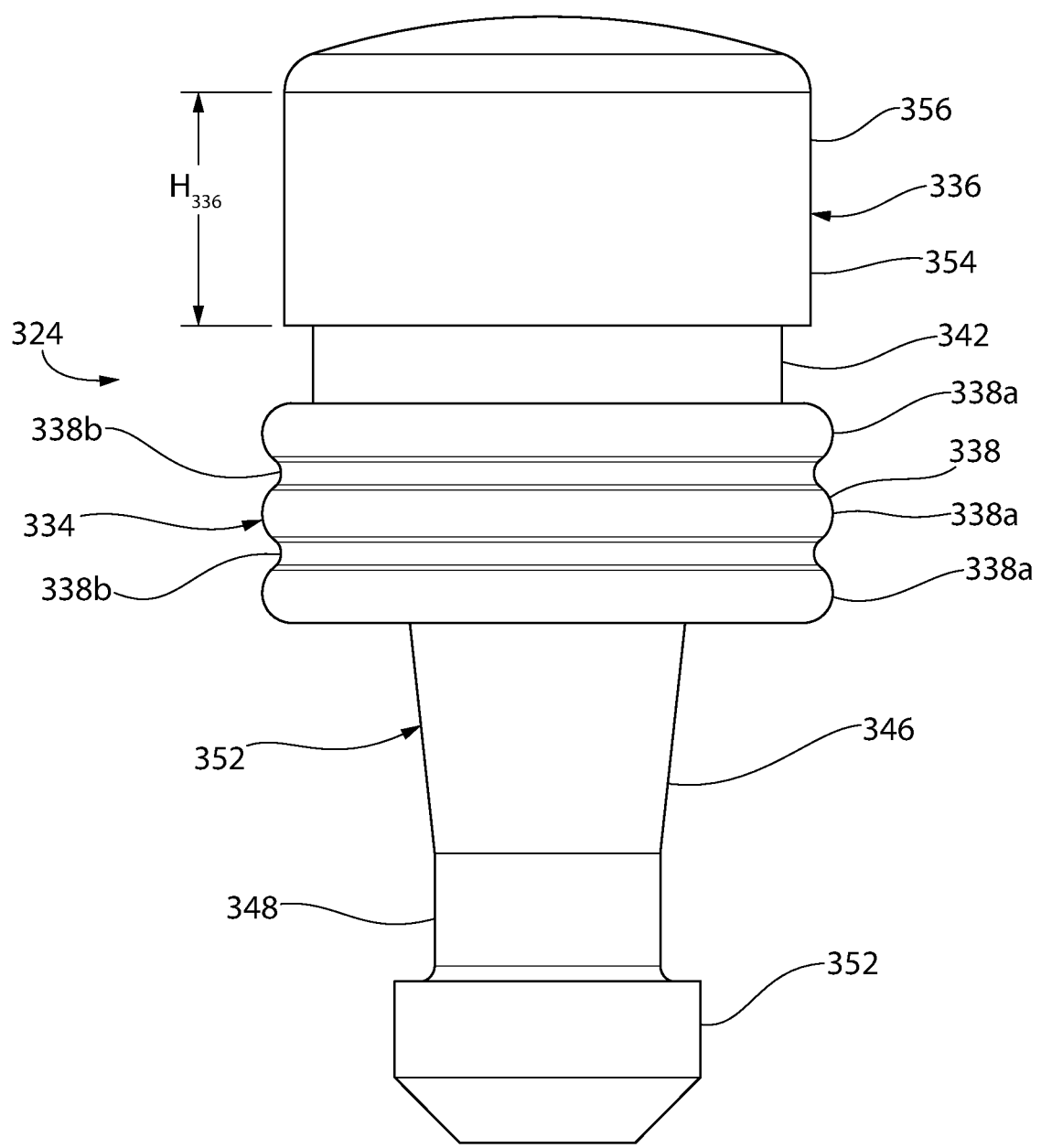
FIG. 11 is a side view of the convertible plunger of FIG. 10.
Figure 12:
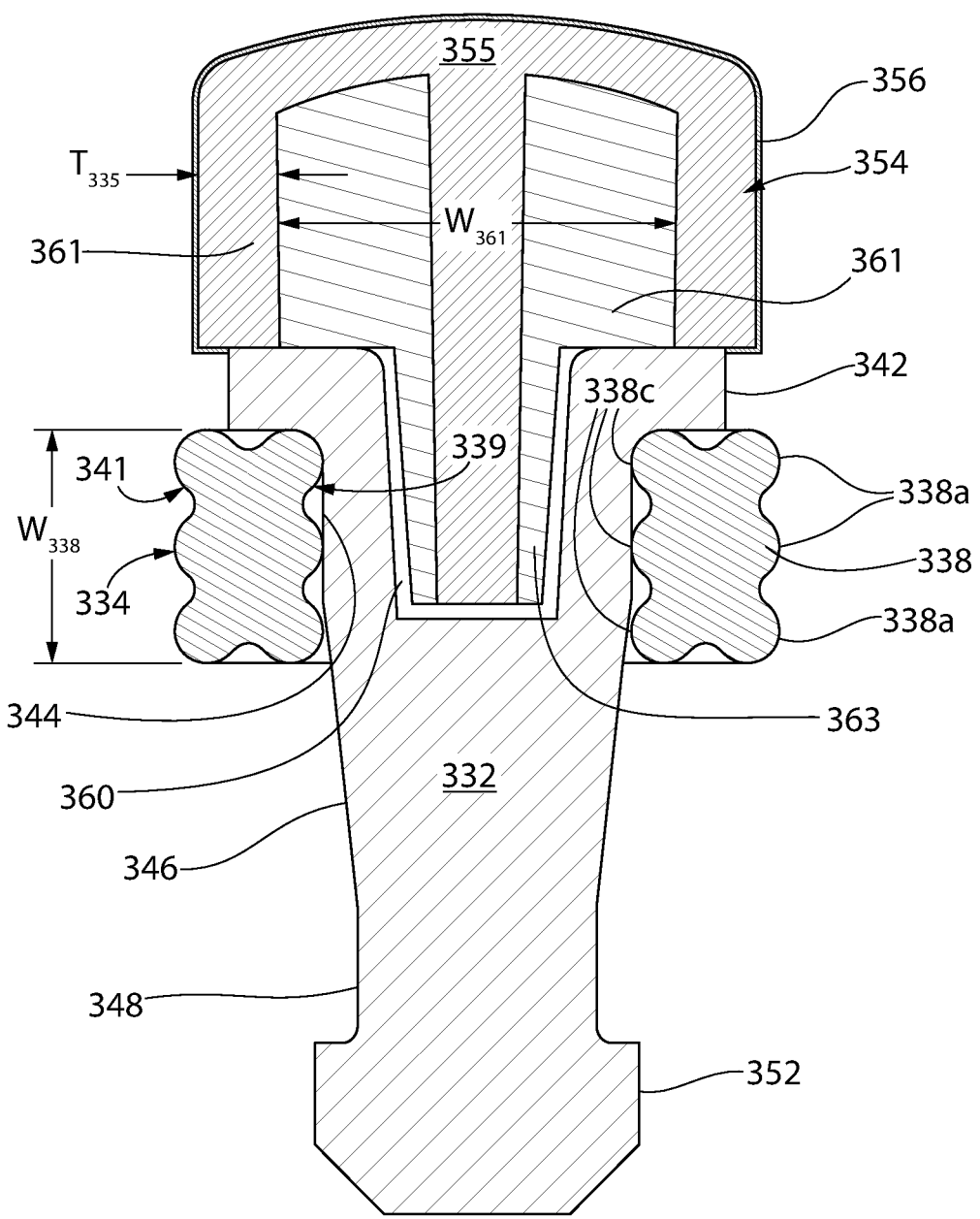
FIG. 12 is an axial sectional view of the convertible plunger of FIG. 10.

Referring now to FIGS. 10-12, there is shown an alternative embodiment of a convertible plunger 324 according to an aspect of the present invention. The convertible plunger 324 is, to some extent, structurally and functionally similar to the plunger 24 of FIGS. 1 and 2A-3B, although there are important differences. Like its counterpart in FIGS. 1 and 2A-3B, the convertible plunger 324 is configured for operating in sealing mode (wherein the storage sealing section in an engagement position) and gliding mode (wherein the storage sealing section is shifted to a release position), substantially as described above. Also, the convertible plunger 324, like the plunger 24 of FIGS. 1 and 2A-3B, is of the independent storage sealing section plunger type. Further, the plunger 324 may be secured to a plunger rod to form a plunger assembly, e.g., much like the embodiment of the assembly 20 shown in FIG. 1. For the sake of brevity, similar features as between the two embodiments (e.g., material of storage ring, the manner in which the plunger is secured to a plunger rod, the basic function of the plunger etc.) will not be discussed in great depth here. However, differences may be noted.

The convertible plunger 324 comprises a rigid central core 332, which would be coaxial with the central axis of a syringe barrel when assembled into a syringe (e.g., the syringe barrel 12 of FIG. 1). The central core 332 is preferably made from a rigid injection moldable thermoplastic polymer, more preferably from a polyolefin such as polypropylene (PP), cyclic olefin copolymer (COC) or cyclic olefin polymer (COP). The liquid sealing section 336 is mounted on the distal end of the plunger's central core 332, while the storage sealing section 334 is located proximally of the liquid sealing section 336. The storage sealing section 334 is provided in the form of a unitary storage ring 338 mounted on a portion of the central core 332. The central core 332 in this embodiment (and others disclosed herein) functions as a rigid ring carrier, which is preferably more rigid than the ring 338. The storage ring 338 comprises an inner surface 339 facing generally radially inward toward the central core 332 and an outer surface 341 facing generally radially outward away from the central core 332. Preferably, when the storage ring 338 is in an uncompressed state, the inner surface 339 is symmetrical about a plane of symmetry across the width $W_{338}$ (between proximal and distal ends) of the storage ring 338. Also, when the storage ring 338 is in an uncompressed state, the outer surface 341 is preferably symmetrical about a plane of symmetry across the width $W_{338}$ of the storage ring 338. This symmetrical configuration provides stability to the storage ring 338 when the convertible plunger 324 is in storage mode and when the plunger 324 transitions to dispensing mode. A non-symmetrical configuration could result in the ring tilting or wobbling axially, potentially compromising the ring's sealing function and its ability to facilitate the plunger's smooth transition from storage mode to dispensing mode. While serving essentially the same purpose as the O-ring 38 of convertible plunger 24, the storage ring 338 of convertible plunger 324 is not round in cross-section and thus is more appropriately referred to as a storage ring (indicating its basic function and structure), rather than specifically as an O-ring (referring to a storage ring having a generally round cross-sectional structure, such as shown in FIGS. 1 and 2A-3B). An O-ring is merely a type or shape of storage ring.

The outer surface 341 of the storage ring 338 in the illustrated embodiment (FIGS. 10-12) includes three hills or ribs 338*a*, wherein the middle rib is separated from neighboring ribs 338*a* by valleys 338*b* on either side of the middle rib. Multiple ribs 338*a* are configured to provide redundancy in storage sealing. An additional consideration is that change in pressure within a syringe (e.g., during transport at high altitudes) may cause an air bubble in the liquid contents of the syringe to compress or expand, causing a plunger to slightly move. Multiple ribs 338*a* on the storage ring 338 helps to reduce the risk that the plunger 324 will move into an unsterile area of the syringe. Optionally, the contours of the inner surface 339 are mirror images of the contours of the outer surface 341 of the storage ring. For example, the ribs 338a on the outer surface 341 are directly opposed by corresponding ribs 338c on the inner surface 339 located 180° from the ribs 338a.

Notably, the storage ring 338 is configured to provide, when in the engagement position, a gas-tight seal between both: (1) the storage ring 338 and the syringe barrel; and (2) between the inner surface of the storage ring 338 and the central core 332 (the same applies to the O-ring 38 and the syringe barrel 12 and central core 32 of FIGS. 1 and 2A-3B). The storage ring 338 is configured to optimize the sealing and releasing of the seal and minimize or preferably prevent unintended contact with the syringe barrel's inner surface as the plunger travels down the barrel during dispensing of syringe contents. The durometer of the rubber of the storage ring 338 may factor in to such optimization.

It is further preferred that the storage ring 338 preferentially adhere to the syringe barrel over the central core 332 or ring carrier. This is to ensure that the seal between the storage ring 338 and central core 332 releases first (while the storage ring 338 initially continues to adhere to the barrel), allowing the storage ring 338 to move to an unsealed position so that the convertible plunger 324 smoothly transitions to glide mode. Preferential adherence of the storage ring 338 to the syringe barrel also advantageously resists movement of the plunger 324 towards the proximal (and potentially unsterile) end of the syringe. Preferential adherence of the storage ring 328 to the syringe barrel may optionally be achieved, e.g., with a flowable lubricant coating on the central core 332. Such lubricants may include, e.g., PDMS in the form of free silicone oil, cross-linked silicone oil (e.g., through plasma cross-linking), or baked on silicone. Alternatively, the central core 332 may be coated with or embedded with fluorinated lubricants, e.g., Teflon, parylenes or any fluorinated polymer disclosed herein for use as a plunger film or cap material. Alternatively, the central core 332 may be provided with a lubricity coating applied by plasma enhanced chemical vapor deposition (PECVD), optionally using octamethylcyclotetrasiloxane (OMCTS) as a precursor. Such a coating may have the chemistries of a pH protective coating or a lubricity coating as described in U.S. Pat. No. 7,985,188, which is incorporated herein by reference in its entirety. Any of the aforementioned lubricating means may be provided between the storage ring and the ring carrier to facilitate sliding of the storage ring axially along the ring carrier while the ring preferentially adheres to the interior wall of the medical barrel. Notably, however, it is highly preferred that neither the medical barrel-contacting surfaces of the plunger 324 (storage sealing section 334 and liquid sealing section 336) nor the inner surface of the medical barrel are coated with flowable lubricant such as free silicone oil. In this preferred aspect of the invention, the convertible plunger 324 provides an "oil-free" solution for prefilled syringe applications, which is advantageous for reasons explained above.

The central core 332 is an elongated rigid member comprising, from the distal end thereof, a flange 342 which projects radially outward from the central core 332. Proximal to the flange 342 is an annular storage platform 344, which supports the storage ring 338 when the plunger 324 is in storage sealing mode. Proximal to the storage platform 344 is a conically tapering section or gradual transition region 346 which terminates in a cylindrical section or dispensing platform 348, the external diameter of which is less than that of the storage platform 344. The dispensing platform 348 terminates at a flange 352.

The convertible plunger 324 operates largely in the same way as its counterpart in FIGS. 1 and 2A-3B to transition from storage sealing mode to a dispensing mode. These details will be summarized here in the context of the plunger 324 of FIGS. 10-12. As shown in FIGS. 10-12, the storage ring 338 is disposed on the storage platform 344. In this position, the storage ring 338 is configured to provide sufficient compression against a medical barrel in which it is disposed, so as to provide a gas-tight and liquid-tight seal, thus providing CCI and protecting sterility of the barrel's contents over a desired shelf life. At the time of actuation/use, when plunger 324 begins to advance in a distal direction in a medical barrel, the central core 332 slides distally with respect to the storage ring 338, causing the ring 338 to transition to the conically tapering section or gradual transition region 346 and then ultimately end at the dispensing platform 348. The gradual transition region 346 is shown in a conical shape, but may be in other configurations, e.g., curved.

When disposed on the dispensing platform 348, the storage ring 338 provides either reduced compression or no compression whatsoever against the medical barrel, thus putting the plunger 324 in dispensing mode. The flange 352 catches the storage ring 338, preventing it from disassociating itself from the proximal end of the central core 332. This also blocks plunger movement in a proximal direction in the event the storage ring fails to release from the barrel, thus reducing the risk of the storage ring 338 contacting an unsterile area within the syringe barrel.

As mentioned above, the liquid sealing section 336 is disposed on the plunger 324 distal to the flange 342 and storage sealing section. The liquid sealing section 336 provides a liquid-tight seal with the barrel sidewall and preferably also provides CCI for barrel contents. The liquid sealing section 336 optionally comprises a head 354 having a film 356 wrapped thereon, as substantially described above with respect to other embodiments. As shown in FIG. 12, the head 354 comprises a resilient material such as an elastomer 355 that is disposed over a rigid support 361, preferably a polymer support. The rigid support 361 advantageously provides a rigid surface to secure or bond the liquid sealing section 336 to the central core 332. The rigid support 361 may include a stem 363 that is secured within a central mating recess 360 of the central core 332, e.g., by ultrasonic welding, an adhesive, a press-fit, a snap-fit or through threaded engagement. Particularly if ultrasonic welding is used, the rigid support 361 is preferably the same material as the central core 332 (e.g., a desired polyolefin). Optionally, the film 356 edge terminates within the central mating recess 360 of the central core 332 and is secured therein, rendering the film edge unexposed after assembly, thus strengthening the bond between the film 356 and the head 354.

Optionally, the head 354 may be made through two-shot injection molding, wherein a first shot injects the rigid support 361 within a mold and the second shot injects the elastomer 355 within the mold, or vice versa. Such a method advantageously avoids the need for assembling separate components to make the head 354. If a two-shot molding process is used, the materials must be compatible to enable the elastomer 355 and rigid polymer support 361 to bond together, thus forming a unitary structure. For example, if the elastomer 355 is a polyolefin based thermoplastic elastomer, the rigid support 361 is preferably a polyolefin, such as PP, COP or COC.

This plunger configuration provides several advantages. For example, the film 356 may be wrapped tightly over the head 354 without distorting the shape of the film or head, due to the rigid internal structure. Moreover, the rigid central core 332 facilitates automation, while still providing an elastomer 355 that is sufficiently resilient enough to provide adequate liquid sealing. In addition, this construction minimizes the amount of elastomeric material that may be subject to compression setting.

Optionally, the film may be wrapped about the plunger head according to the following process. The process comprises any combination of one or more of the following steps: (a) optionally loading film onto rollers; (b) optionally loading a plunger head in tooling; (c) optionally heating the film to a temperature for a length of time configured to render the film formable into a preform, wherein the controller is optionally set to heat the film to very high temperature (e.g., a controller set point of at least 1000° C., preferably above 1200° C., optionally about 1275° C.); (d) optionally applying a vacuum to pull film into preform tooling, wherein the preform is smaller than the plunger head; (e) optionally cutting out a film disk with the preform and transfer the disk to a forming station; (f) optionally clamping the cut disk with the preform rigidly at the perimeter, inverting the preform using a vacuum and push the plunger head up through the inverted preform stretching the preform to conform to the plunger head; (g) optionally pushing the plunger head and preform through an opening to gather the excess film behind the plunger head, holding film and plunger head on circumference with a first gripper and clamping the excess film behind the plunger head with a second gripper and rotating the first gripper at least 180°, optionally at least 270°, optionally up to about 720° rotation, wherein such rotation tightens the film about the plunger head; (h) optionally trimming the excess film away and rotating the plunger head to break the plunger free from the film; and (i) optionally finishing the film edge by using a heated tamping die to tamp cut the edge to back surface of the plunger head. This process is an alternative to traditional methods of laminating the film during a molding process.

Dimensions of the plunger may vary depending on specific needs, applications and syringe barrel diameters. Applicants have found that certain specific dimensions may be advantageous. The plunger head 354 needs to provide a liquid tight seal to prevent liquid contents of the syringe from leaking past the plunger head 54, a phenomenon Applicants refer to as "blowback." An embodiment with a sealing height $H_{336}$ of the liquid sealing section 336 of 3.0 mm and a diameter of 6.50 mm in a 6.48 mm syringe underwent testing, described in Example 2, below. That embodiment successfully blocked a 40 N load, without any leakage, wherein that load was applied distally, i.e., in a direction for dispensing liquid contents (although the needle was blocked to prevent the liquid from exiting the syringe). Also, Applicants have found that the wall thickness $T_{355}$ of the elastomer 355 of the plunger head 354 impacts glide force. For example a $T_{355}$ of 1.00 mm has a higher glide force than a $T_{355}$ of 1.45 mm. Also, Applicants have found a rigid support width $W_{361}$ of 3.7 mm to be beneficial for some applications.

Figure 12A:
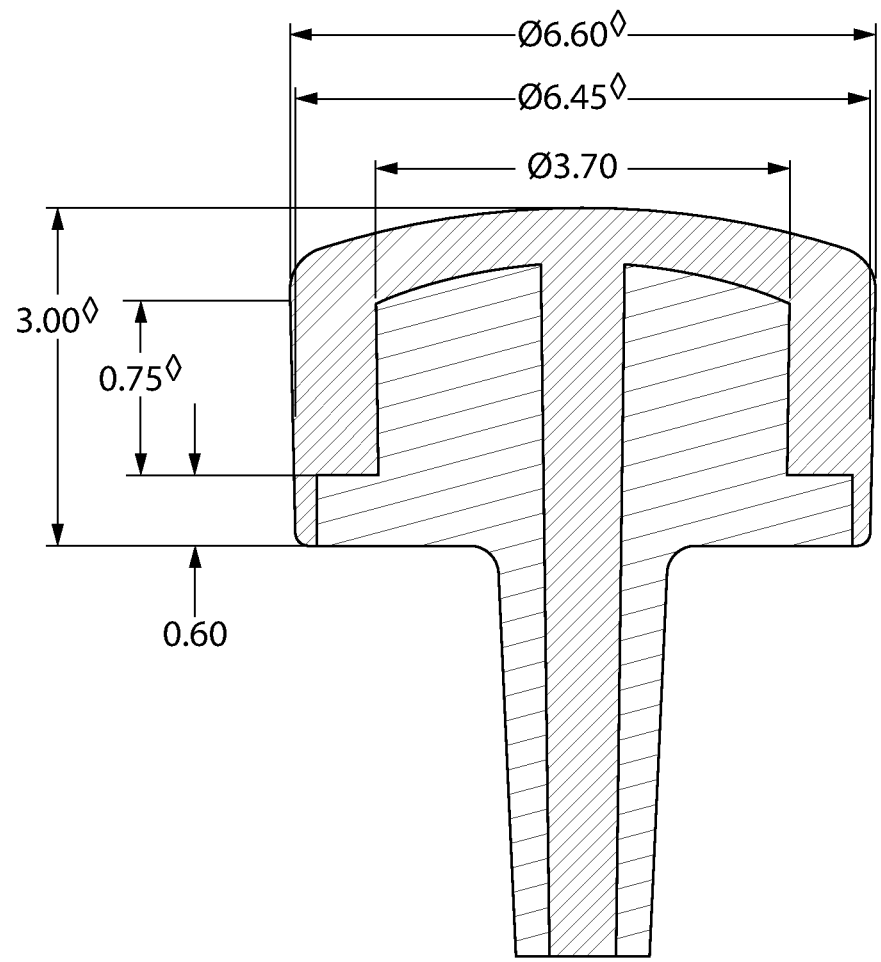
FIG. 12A is an axial sectional view of an alternative geometry and dimensions for a plunger head of a liquid sealing section according to an optional embodiment.

Optionally, an alternative geometry is shown in FIG. 12A, which aims to reduce the interference area between the liquid sealing section and syringe barrel. FIG. 12A illustrates a height of 0.75 mm at the maximum diameter.

Preferably, a liquid sealing section may be configured, according to an aspect of the invention, to provide a CCI level of sealing, although not gas (e.g., oxygen) sealing.

As discussed herein, the terms "central core" (e.g., 32 or 332) or "sleeve" (in the case of the sleeve 160 of the embodiment shown in FIGS. 4A and 4B), have a storage ring or O-ring disposed directly thereon. The central core, sleeve or any other element on which the ring or storage sealing section is disposed may be referred to herein generically as a "ring carrier." The ring carrier, in whichever form it takes, should be rigid. A rigid ring carrier provides necessary support and dimensional tolerances for the storage ring to reach desired and precise levels of compression when the plunger is in storage mode and to release smoothly (with little to no perception to the user) when the plunger transitions to dispensing mode. It should be borne in mind that the storage ring and the plunger in general will typically be tiny. Since the plunger components need to operate smoothly in what is typically a small-diameter syringe barrel, tight dimensional tolerances are needed. A rigid ring carrier does not compress when the storage ring disposed thereon compresses. In this way, the storage ring is the only variable that must be accounted for in designing a ring that is configured to provide an adequate seal on the one hand when the plunger is in storage mode and a smooth transition and plunger force on the other when the plunger is transitioned to dispensing mode. This configuration is much preferred to a compressible ring carrier, since that would add a level of complexity and difficulty (i.e., another variable) to achieving adequate seal and desirable plunger force.

Optionally, in any embodiment, the liquid sealing section is a separate component and made of a different composition, from the ring carrier. For example, the ring carrier may be made from a polyolefin while the liquid sealing section may be a fluoropolymer-covered injection molded TPE over a rigid polymeric skeleton. In such a case, the liquid sealing section is more flexible (and resilient) compared to the rigid ring carrier. In any embodiment of plungers according to the invention, the liquid sealing section may be more flexible and resilient than the rigid ring carrier.

The inventors have learned that the manner in which the storage ring is inserted into a syringe barrel is consequential. For example, it has been discovered that sliding the storage ring (e.g., using a shaft/sleeve) onto the storage platform once the plunger head has been inserted into the syringe barrel may cause torsional and circumferential distortion of the storage ring and/or create an unwanted "pressure zone" between the storage ring and the liquid sealing section. Such a pressure zone, which traps pressurized air between the two sealing sections, may have the tendency to push the storage ring back over time and can result in unwanted pressure against the liquid contents of a prefilled syringe.

To address these problems, the inventors have developed the alternative embodiment of a convertible plunger 724 shown in FIGS. 21-23C. The plunger 724 is, to some extent, structurally and functionally similar to the plunger 324 of FIGS. 10-12, although there are important differences to the construction and assembly of the plunger 724. Like its counterpart in FIGS. 10-12, the convertible plunger 724 is configured for operating in a sealing mode (wherein the storage sealing section in an engagement position) and gliding mode (wherein the storage sealing section is shifted to a release position), substantially as described above. Also, the convertible plunger 724 is of the independent storage sealing section plunger type. For the sake of brevity, similar features as between the two embodiments (e.g., material and configuration of the storage ring, the manner in which the plunger is secured to a plunger rod, the basic function of the plunger, etc.) will not be discussed in great depth here. However, differences may be noted. The convertible plunger comprises a ring carrier in the form of a rigid central core 732, which would be coaxial with the central axis of a syringe barrel when assembled into a syringe (e.g., the syringe barrel 12 of FIG. 1). The storage sealing section 734, in the form of a storage ring 738, is mounted on a portion of the central core 732. The central core 732 is an elongated rigid member comprising, from the proximal end thereof, a flange 752 (which may be secured to a plunger rod, e.g., via a threaded engagement or snap fit) which is adjacent to an annular dispensing platform 748. Distal to the dispensing platform 748 is an annular steep transition region 746 which leads to the annular storage platform 744. It has been found that the more steep or abrupt the transition region, the more smoothly the plunger transitions from storage mode to dispensing mode. The outer diameter of the central core 732 narrows distally to the storage platform 744 to form two resilient prongs 772 of an annular insertion platform 770, the function of which is described below.

Unlike the embodiment of FIGS. 10-12, the central core 732 is mounted to the proximal end of a connector body 780 (as opposed to the proximal end of a storage sealing section 336). The connector body 780 is a preferably rigid (e.g., polymeric) and generally cylindrical member, the proximal end of which receives and connects to the resilient prongs 772 of the central core 732. The liquid sealing section 736 is mounted to the distal end of the connector body 780 in essentially the same way as the liquid sealing section 336 mounts to the central core 332 of FIGS. 10-12. The description above with respect to the liquid sealing section 336 will suffice for description of the same vis-à-vis the plunger 724 of FIGS. 21-23C. It will only be briefly noted that the liquid sealing section 736 optionally comprises a head 754 having a film 756 wrapped thereon. Notably, the film 756 is wrapped entirely around the head 754 and continues along an underside of the head 754, wherein the film 756 is sandwiched between the head 754 and the connector body 780. The head 754 comprises a stem 763 that is assembled and secured into a central mating recess 760 of the connector body 780, e.g., by ultrasonic welding, an adhesive, a press-fit, a snap-fit or through threaded engagement.

The connector body 780 comprises an axial channel 784 leading to a wider opening 776 that optionally bores entirely through a center portion of the connector body 780, in a direction perpendicular to the central axis of the axial channel 784. This configuration simplifies injection molding of the connector body 780. The opening 776 comprises a ridge section 782 adjacent to where the axial channel 784 meets the opening 776. The prongs 772, at their distal ends, comprise radially outward projecting abutments 774. The abutments 774 are retained underneath the ridge section 782 to secure the central core 732 to the connector body 780.

To assemble the central core 732 to the connector body 780, the two components should be aligned and axially centered. The prongs 772 of the central core 732 are then inserted into the axial channel 784 of the connector body 780. The axial channel 784 is configured to facilitate the insertion of the prongs 772, e.g., with an annular chamfer 786 at the proximal end of the axial channel 784. When the prongs 772 contact the chamfer 786, the prongs 772 are urged to resiliently flex or compress radially inward so that the prongs 772 and abutments 774 fit entirely within the axial channel 784 as the prongs 772 are moved distally into the axial channel 784. Once the abutments 774 fully reach the wider opening 776, the prongs 772 are released from their compressed state and the abutments 774 are retained underneath the ridge section 782, preventing the central core 732 from being separated from the connector body 780. In short, the prongs 772 secure the central core 732 to the connector body 780 in a snap-fit configuration. This provides advantages during assembly of the plunger 724 into a syringe barrel, as explained now.

Figure 21:
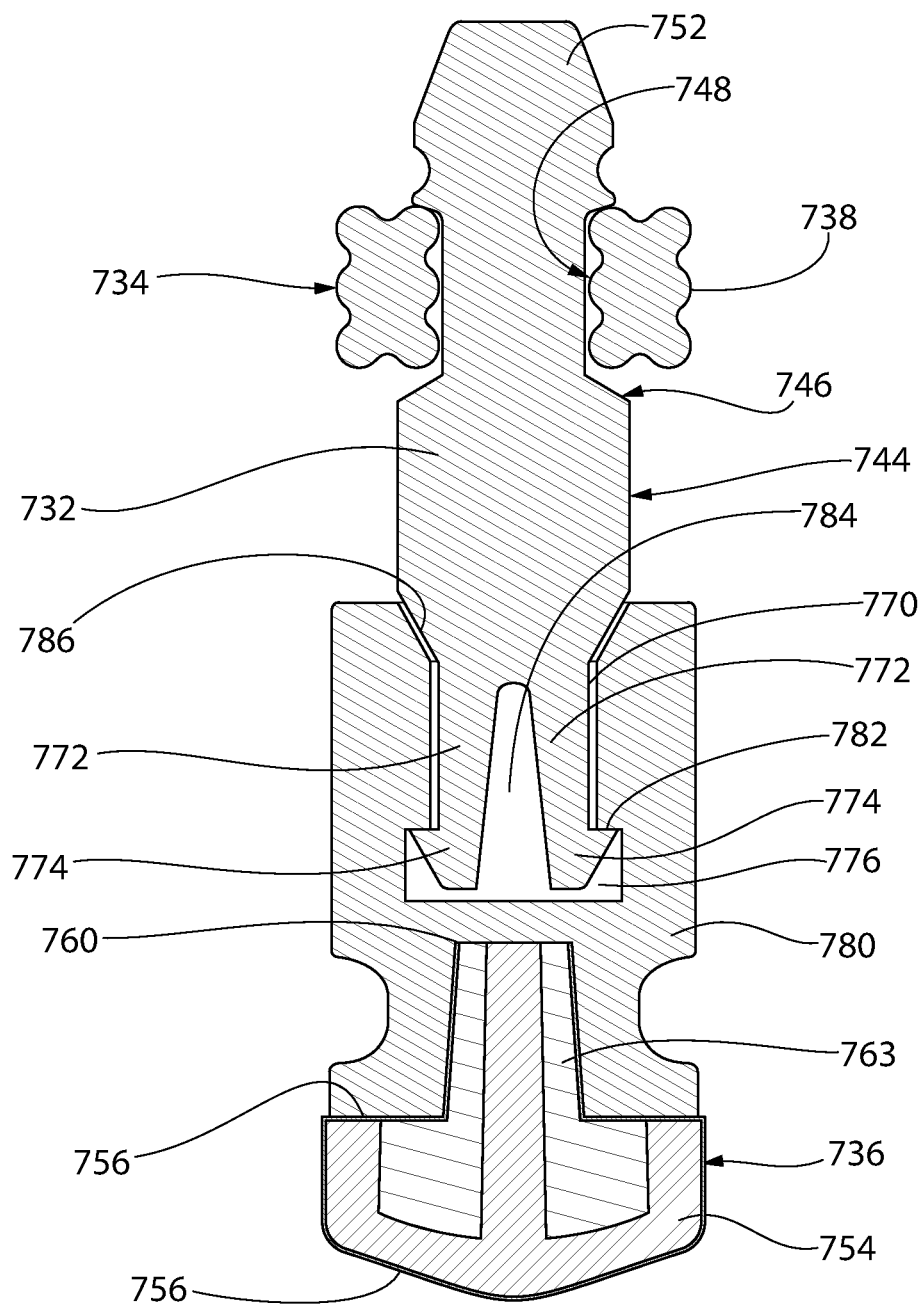
FIG. 21 is an axial sectional view of an alternative convertible plunger embodiment comprising a connector, which at a distal end thereof, is secured to the liquid sealing section and at a proximal end thereof, is secured to the central core.
Figures 22A, 22B:
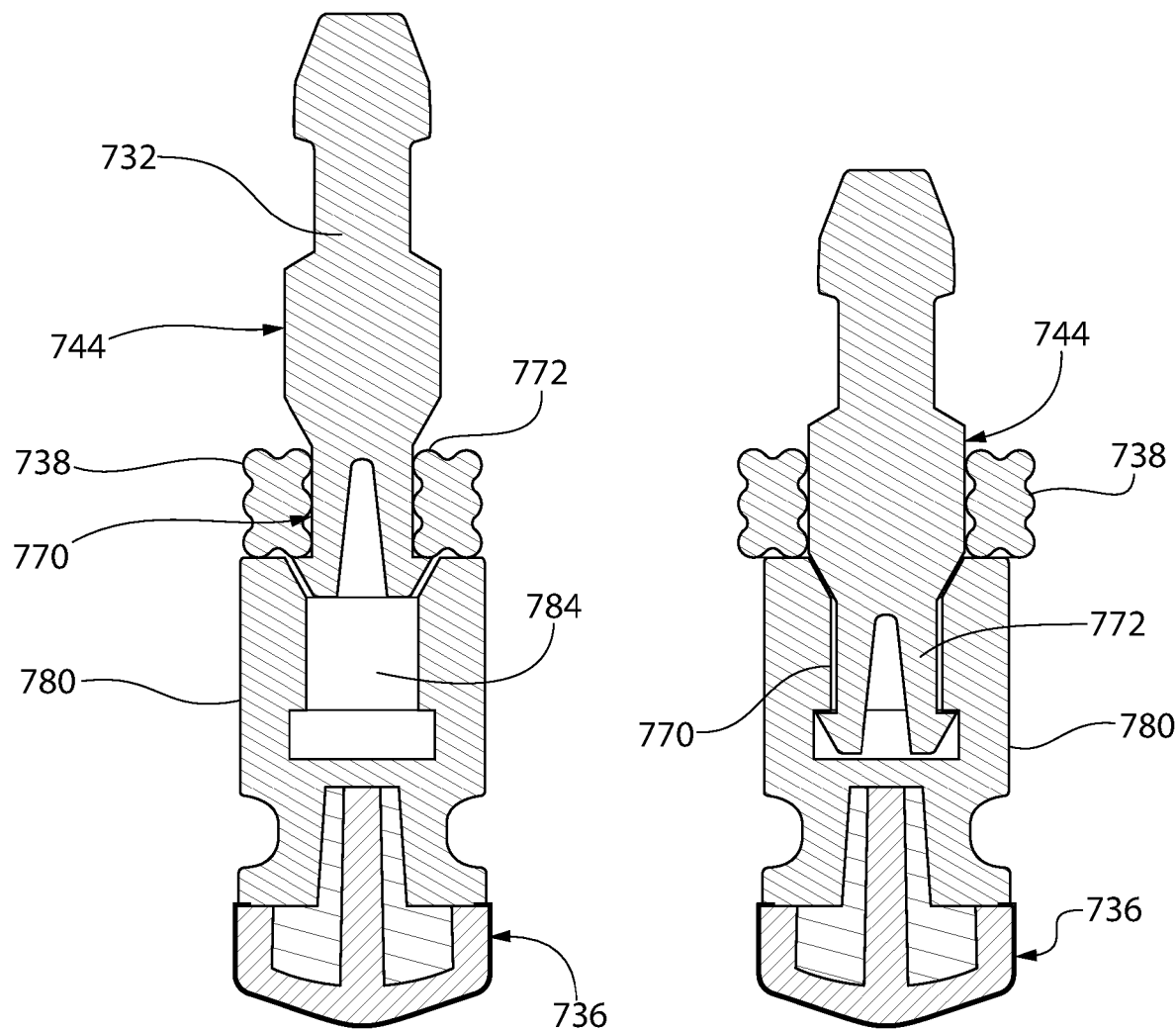
FIGS. 22A and 22B are schematic drawings illustrating the manner in which the convertible ring of FIG. 21 may be assembled.

FIGS. 22A and 22B are schematic drawings illustrating the manner in which the storage ring 738 via the central core 732 are assembled onto the connector body 780 and liquid sealing section 736 subassembly or article, thus forming a completed convertible plunger 724. FIG. 22A shows the components just prior to fully assembling them to form the plunger 724. As shown, the distal end of the central core 732 is protruding slightly into the axial channel 784 of the connector body 780 and is thus not yet secured thereto. Notably, in this position, the storage ring 738 is disposed on the annular insertion platform 770 of the central core 732 or ring carrier. The annular insertion platform 770 has a narrower outer diameter than the annular storage platform 744. As such, the outer diameter of the storage ring 738 is correspondingly less than the ring's 738 outer diameter when disposed on the storage platform 744, as shown in FIG. 22B. The comparatively small outer diameter of the storage ring 738, when disposed about the insertion platform 770, is configured to facilitate insertion of the ring 738 into a syringe barrel in such a way that the ring 738 does not contact the barrel wall or has only minimal contact with it. When on the insertion platform 770, the sealing ring 738 is in a "load position" wherein the ring 738 slides easily into the proximal end of the syringe barrel. As the prongs 772 are urged downward into the axial channel 784 of the connector body 780 to ultimately secure the central core 732 thereto (as shown in FIG. 22B), the storage ring 738 transitions from load position on the insertion platform 770 to engagement position, wherein the ring is disposed about the storage platform 744. Optionally, as shown in FIG. 22B, the entire ring 738, when the plunger is in storage mode, is disposed about the storage platform 744. In other words, no part of the ring 738 contacts the dispensing platform when in storage mode. This helps facilitate stability of the storage ring 738. Likewise, as shown in FIG. 21, the entire ring 738 is optionally disposed about the dispensing platform 748 when the plunger 724 is in dispensing mode, which facilitates stability during dispensing.

Notably, with the aforementioned process, the ring 738 is not separately urged or pushed with a device to set the ring 738 into engagement mode. Rather, the ring 738 is inserted into the syringe barrel with little or no barrel sidewall resistance by placing the ring in load position on the central core 732 before mounting the central core 732 to the connector body 780. As seen in both FIGS. 22A and 22B, the ring 738 is flush against the proximal end of the connector body when the ring is in load position and in engagement position. In other words, the ring 738 remains in a fixed position during loading while central core 732 moves relative to the ring. With no space between the ring 738 and the connector body 728 both before and after the ring 738 compresses against the barrel sidewall, there is no "pressure zone" between the storage ring 738 and the liquid sealing section 736. This design, therefore, addresses the problems identified above with loading the storage ring without distorting it or creating an unwanted pressure zone.

Figures 23A, 23B, 23C:
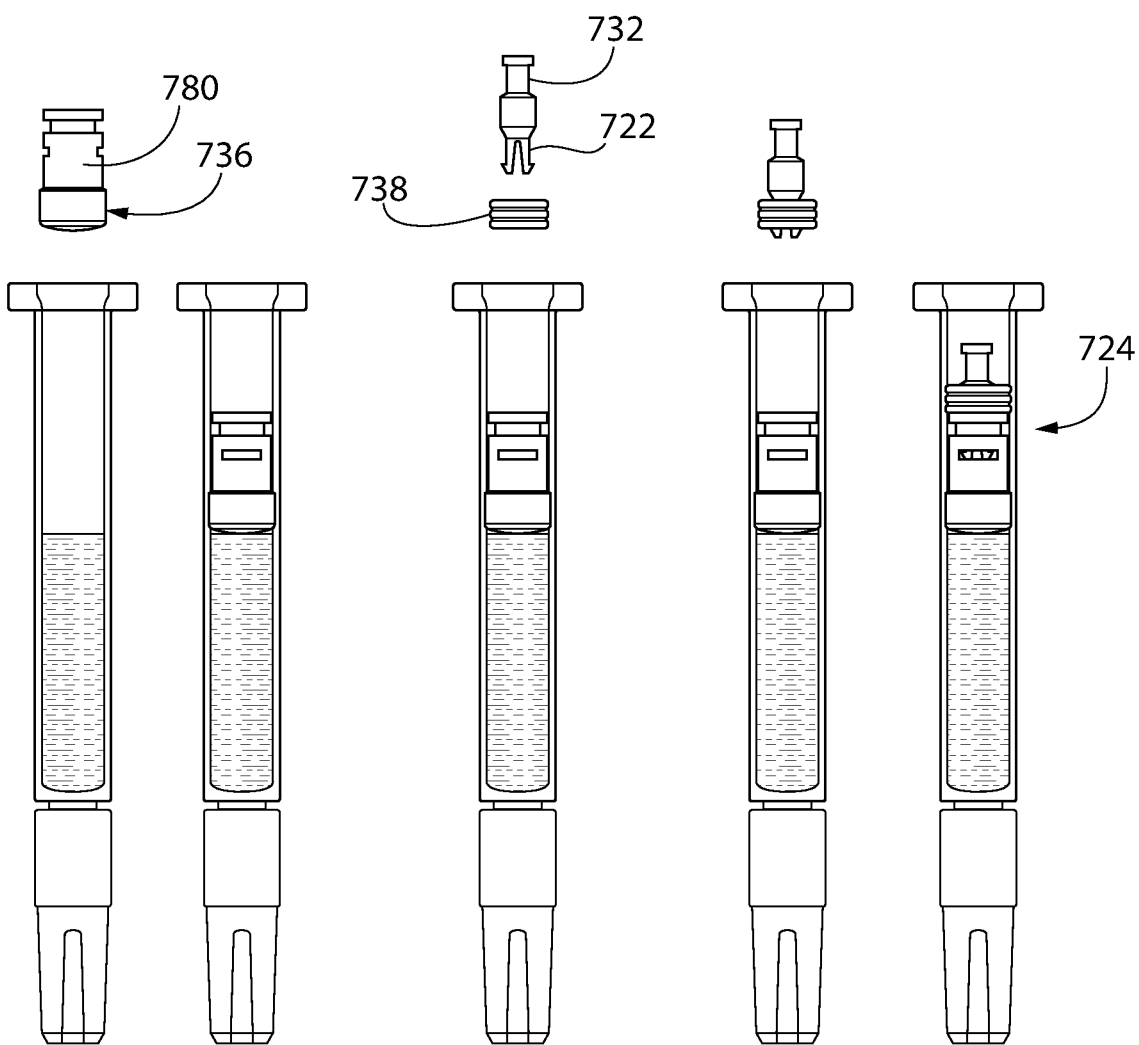
FIGS. 23A-23C are schematic drawings illustrating the manner in which the convertible plunger components of FIG. 21 may be loaded into and assembled within a syringe barrel.

The schematic drawings of FIGS. 23A-23C more fully illustrate the manner in which the components of the convertible plunger 724 may be loaded into a prefilled syringe and assembled. As shown in FIG. 23A, the liquid sealing section 736 and connector body 780 subassembly or article may be loaded into the plunger via traditional methods to load plungers. These include vent tube, vacuum loading and vacuum assist, all of which are described, below. Next, the storage ring 738 and central core 732 subassembly is created by disposing the ring 738 in load position 738 on the prongs 772 of the central core 732. As shown in FIG. 23C, the storage ring 738 and central core 732 subassembly is inserted, e.g., by push-rod or by a plunger rod assembled thereto, until the snap-fit is established with the connector body 780 to form the fully assembled convertible plunger, loaded in engagement mode. It is contemplated that liquid prefilled in the barrel provides resistance necessary to oppose the downward force applied when assembling the central core 732 to the connector body 780. The plunger 724 then may be used, just as described with other embodiments, to convert the plunger 724 from engagement position (shown in FIG. 23C) to release position (shown in FIG. 21). It should be noted that the expanded state of the plunger 724 is reducible to a constricted state by an operation that is applied to the internal portion of the plunger to reduce or eliminate the outward radial pressure provided by a comparatively rigid internal portion, in this case, the storage platform 744 of the ring carrier 732. The ring 738 is set in the expanded state through application of a setting force onto the convertible plunger 724 in a distal direction. The operation to reduce the plunger to the constricted state comprises application of an actuation force onto the convertible plunger 724 in the distal direction. With such a preferred embodiment, the plunger 724 does not need to be pulled back or primed to set it in, or remove it from engagement mode, before transitioning to dispensing mode and then dispensing product.

Figure 24:
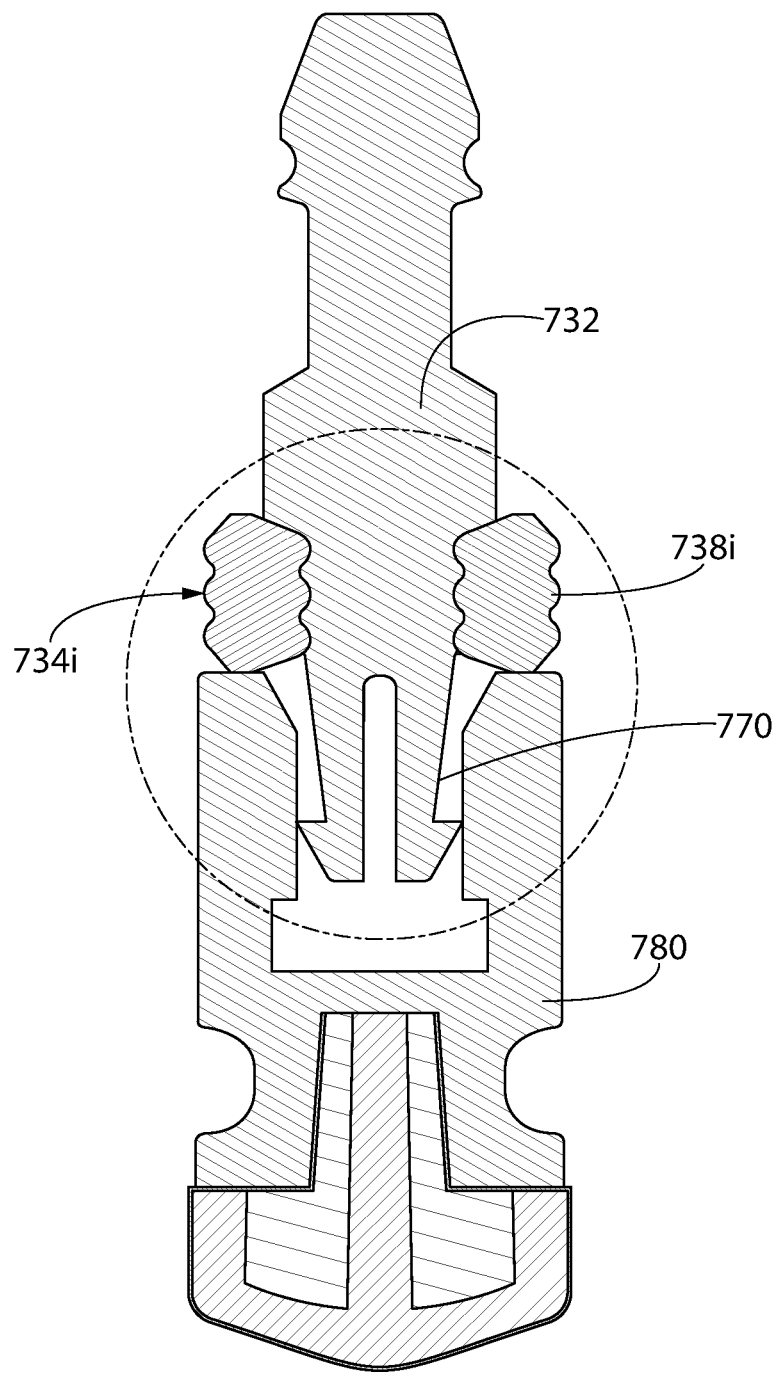
FIG. 24 is an axial sectional view of an alternative convertible plunger identical to the plunger of FIG. 21, except that the cross-section of the storage ring of FIG. 24 is an alternative geometry compared to that of FIG. 21.
Figure 24A:
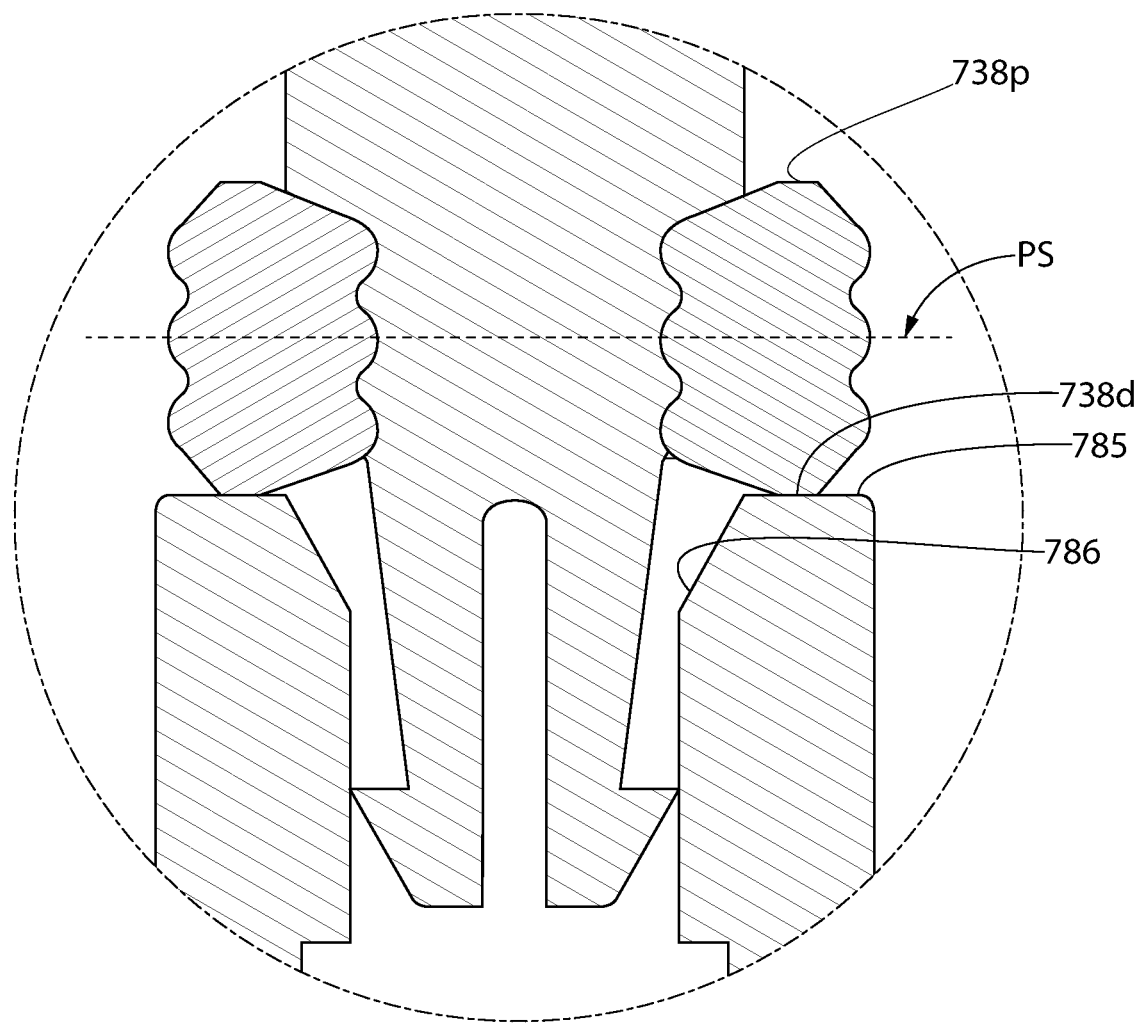
FIG. 24A is an enlarged partial view of the plunger of FIG. 24 highlighting the alternative geometry of the cross-section of the storage ring.

FIG. 24 is an axial sectional view of an alternative convertible plunger identical to the plunger of FIG. 21, except that the cross-section of the storage ring of FIG. 24 is an alternative geometry compared to that of FIG. 21. FIG. 24A is an enlarged partial view of the plunger of FIG. 24 highlighting the alternative geometry of the cross-section of the storage ring. As shown, the alternative storage ring 738i includes an outer surface facing generally radially outward away from the ring carrier. In its uncompressed state, the ring 738i includes a proximal end 738p, a distal end 738d and a radial plane of symmetry PS between the proximal 738p and distal 738d ends. Optionally, radial plane of symmetry PS is equidistant from the proximal 738p and distal 738d ends. The outer surface of the ring 738i is symmetrical on either side of the radial plane of symmetry PS. Optionally, the ring 738i is configured such that, in its uncompressed state, a given rib on the inside surface opposes a rib on the outside surface of the storage sealing section 734i. These features may help to facilitate stable seating and translation of the ring 738i. Further, the distal end of the ring 738b contacts the proximal end 785 of the connector body 780, without being disposed in or pressing against the annular chamfer 786.

Additional Methods and Apparatus for Assembling Convertible Plunger Into Syringe Barrel Given the novel configuration of the convertible plunger, as represented by exemplary embodiments described herein, traditional methods for assembling a conventional plunger into a prefilled syringe barrel after a filling operation, are not alone sufficient to assemble the convertible plunger into a syringe barrel. Traditional methods, however, may be incorporated into aspects of novel methods for assembling the convertible plunger into a syringe barrel.

There are three traditional methods for assembling a conventional plunger into a prefilled syringe. The first is use of a vent tube, wherein the plunger is pushed through a tube that is placed into the syringe and exits out the bottom of the tube into its final position within the syringe barrel. The second is use of a vacuum, which is created in the syringe and the plunger is introduced into the opening thereof. Differential pressure forces the plunger down into the barrel into a final position. A third method, known as vacuum assist, creates a vacuum and further includes a mechanical element to assist the plunger into its final position. Again, these traditional methods may be used to some extent to effectuate assembly of a convertible plunger into the syringe barrel. However, since the convertible plunger requires not only the plunger head to be disposed within the syringe barrel (which may be done, e.g., via one of the traditional methods recited above), but also setting the storage sealing section into an engagement position, traditional methods/apparatus are not equipped to adequately assemble convertible plungers into a medical barrel, such as a syringe. This section of the specification describes various methods and apparatus for assembling a convertible plunger into a syringe barrel. FIGS. 6A-6E, 13-16B and 18 illustrate apparatus for assembling independent storage sealing section plunger type embodiments into a syringe barrel. FIGS. 16A-17B illustrate apparatus for assembling insert and sleeve plunger type embodiments into a syringe barrel.

Independent storage sealing section plunger embodiments present the issue that the storage ring, if initially positioned in engagement mode (i.e., at its largest diameter), can render it difficult or impossible to effectuate automated plunger insertion into a syringe barrel. Applicants have therefore determined that it is preferred that such embodiments are not initially inserted into a syringe with the storage ring in (expanded) engagement position, but instead in (constricted) release position. Once the plunger is initially inserted in the barrel, e.g., through a traditional method, the storage ring may be displaced from release position and set in engagement position for commercial use.

Figure 6A:
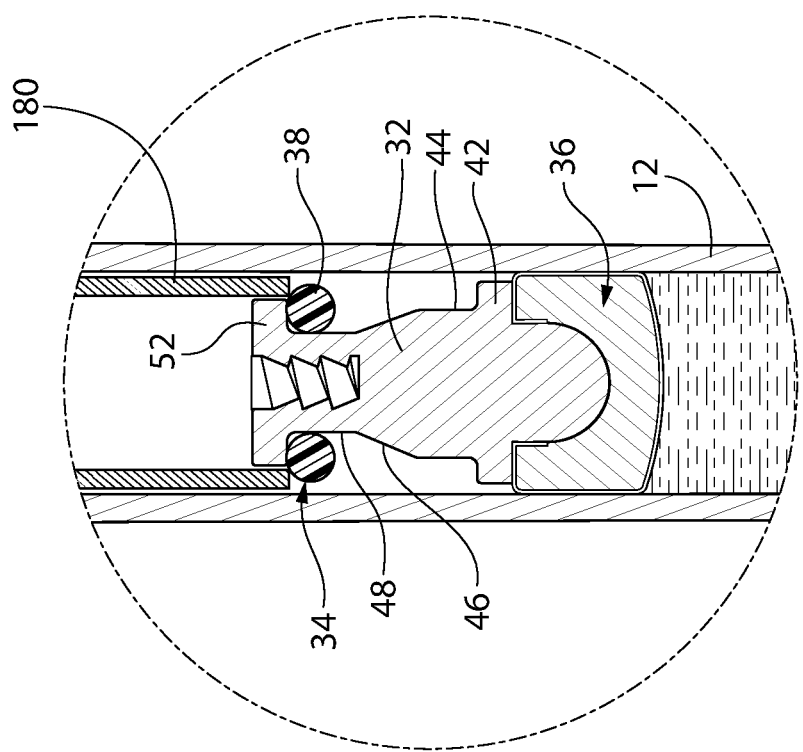
FIGS. 6A-6E constitute a series of enlarged isometric views of a portion of the syringe shown in FIG. 1 during the assembly of its convertible plunger.
Figure 6B:
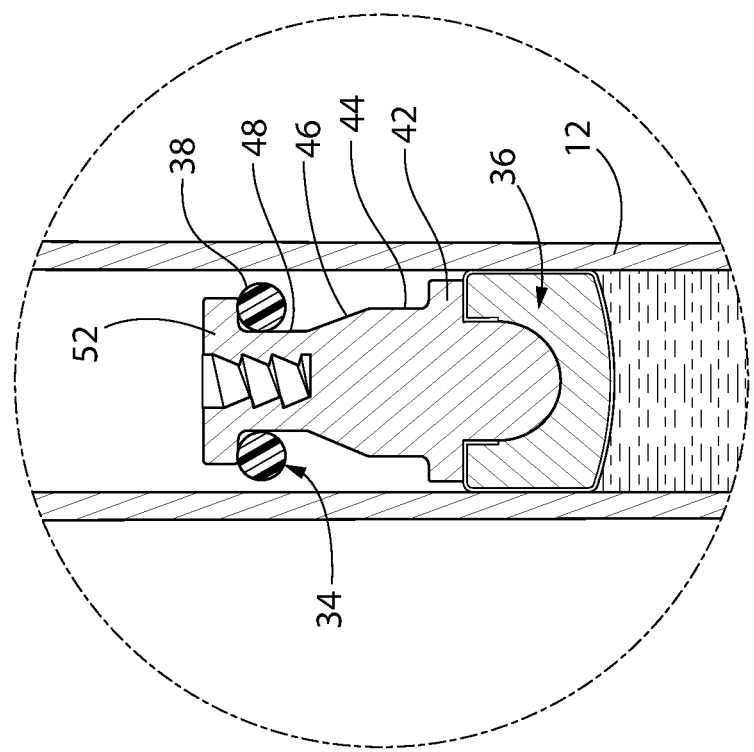
Figure 6D:
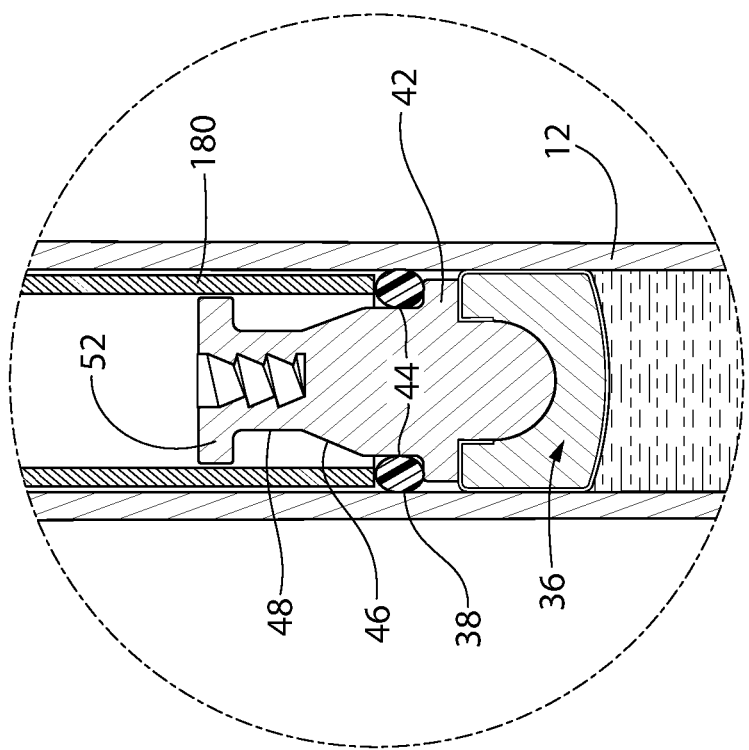
Figure 6C:
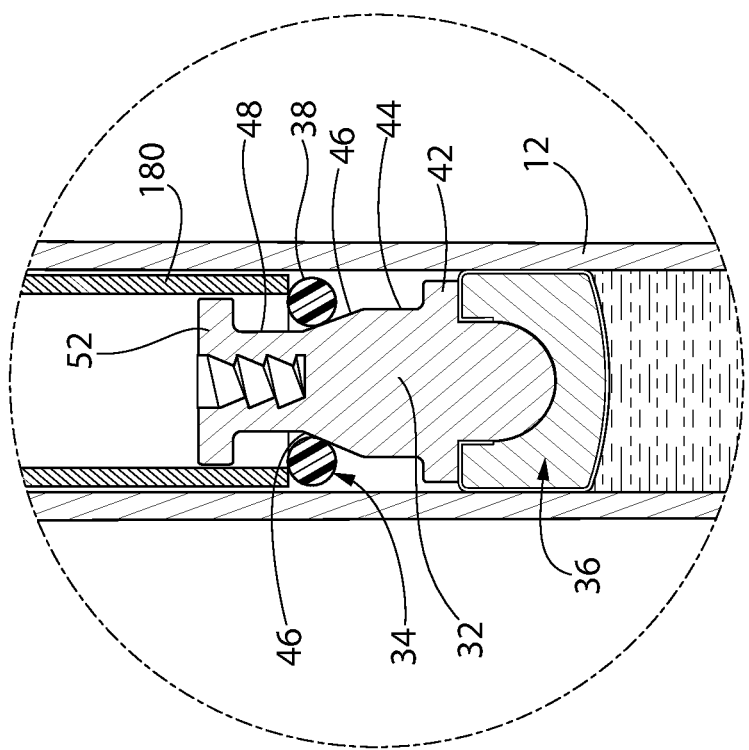
Figure 6E:
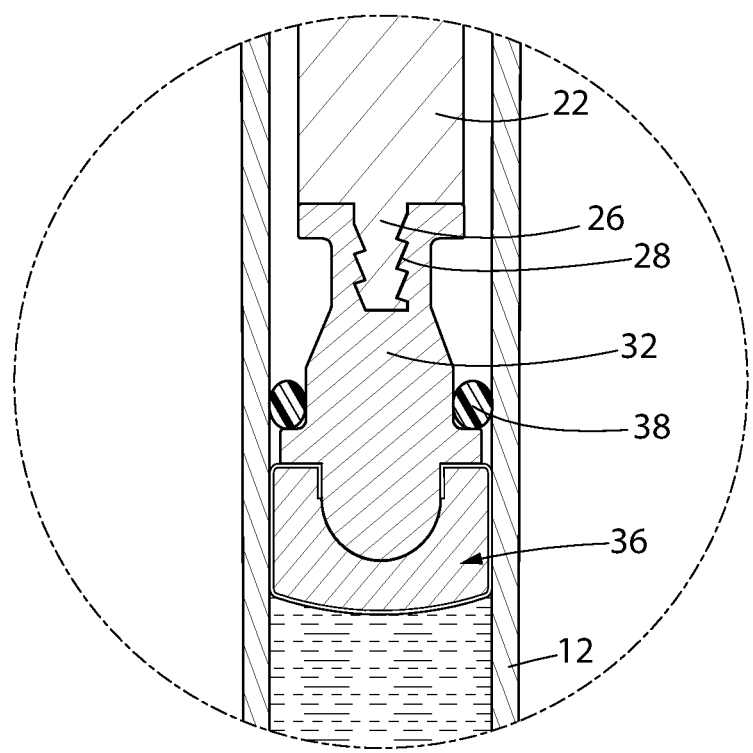

Turning now to FIGS. 6A to 6E the details of the assembly of the components making up the plunger assembly 20 within the barrel 12 of the syringe will now be described. To that end, the convertible plunger 24 is provided in the state wherein its O-ring 38 is located immediately under the flange 52. Thus the O-ring will be in its constricted state so that it will not engage the interior surface of the barrel when introduced therein. With the convertible plunger 24 in that state it is introduced into the proximal open end of the barrel 12 and freely slid to the longitudinal position it will be when in the plunger assembly is in its engagement position, like shown in FIG. 6A. A tubular tool 180 whose inner diameter is slightly larger than the outer diameter of the flange 52 of the central core 32 is then slid over that portion of the central core to engage a portion of the O-ring 38 disposed thereunder, such as shown in FIG. 6B. The tool 180 is then pushed downward to cause the O-ring to slide along the central core in the distal direction, whereupon it will ride up over the conical section 46 and thus be stretched radially outward, like shown in FIG. 6C. Continued pressing on the tool will eventually slide the O-ring into the annular recess 44, like shown in FIG. 6D whereupon it will snap into place in the holding position. Once that has been accomplished the tool 170 can be removed and the plunger rod 22 can then be connected to the convertible plunger 24. To that end the threaded projection 26 at the distal end of the plunger rod 22 can be screwed into the threaded hole or bore 28 in the central core, thereby completing the assembly of the plunger assembly within the syringe's barrel.

Figure 13:
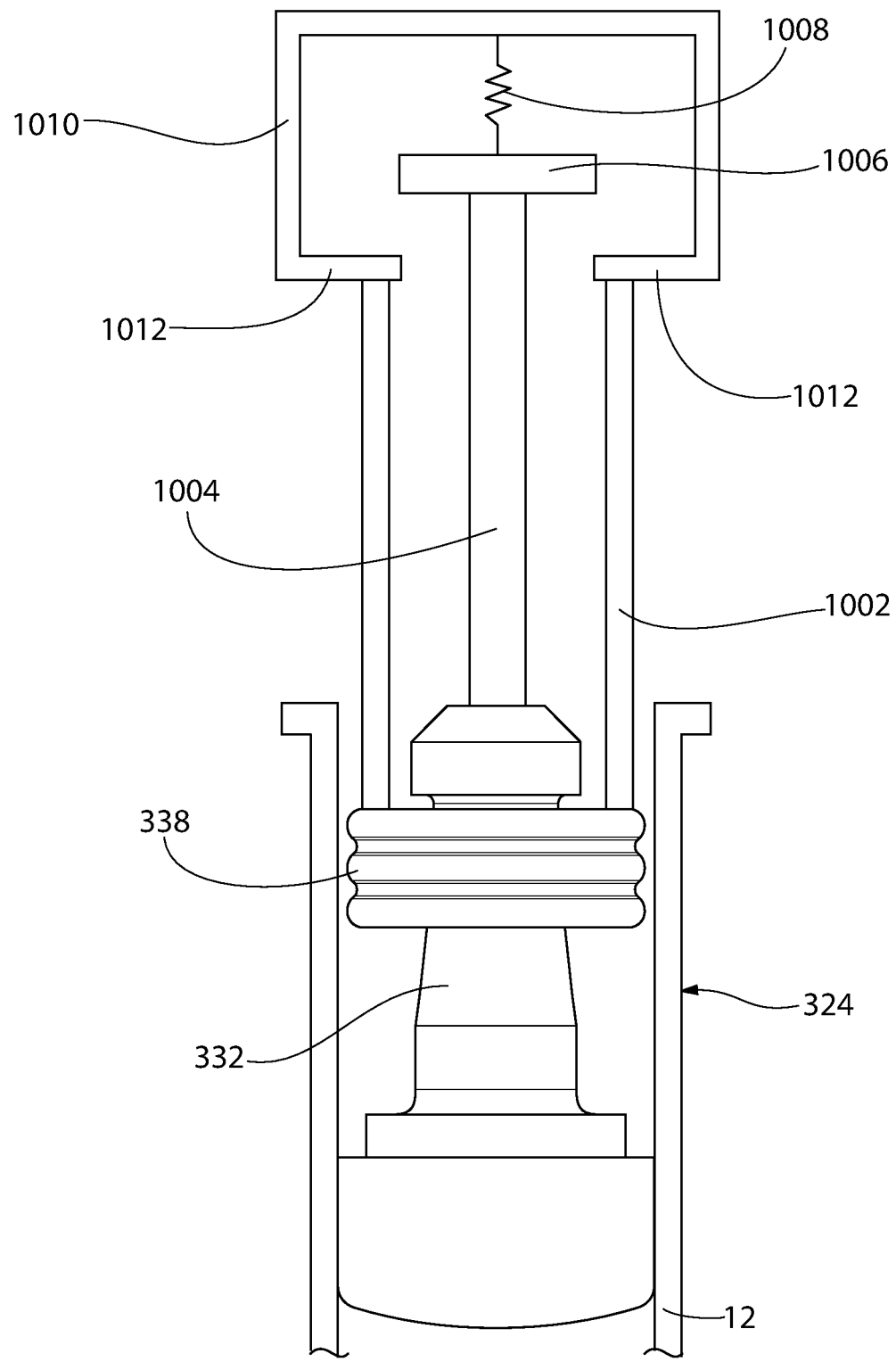
FIG. 13 is a schematic illustration of an embodiment of a plunger insertion apparatus for inserting the plunger of FIG. 10 into a medical barrel.

Referring to FIG. 13, there is shown an optional embodiment of a plunger insertion apparatus 1000, used, e.g., to set the convertible plunger 324 of FIGS. 10-12 in a syringe barrel. As a first step in a method of assembly, as discussed above, one of the traditional methods (e.g., vent tube, vacuum or vacuum assist) may be employed to initially dispose the plunger 324 within a syringe barrel. The apparatus 1000 may be used in a second step to set the ring 338 into engagement mode by displacing it from an initial position on the dispensing platform 348 to a position on the storage platform 344 of the central core 332.

The apparatus 1000 includes a mount 1010 which initially drives the entire plunger 324 distally in direction D using the plunger positioning rod 1004 until flanged end 1006 of the positioning rod 1004 is blocked by stops 1012, at which point plunger movement ceases. The continued downward movement collapses a spring 1008 affixed to a proximal end of the plunger positioning rod 1004, which causes an insertion tube 1002 that is axially driven distally in direction D by the mount 1010 continues to move distally to displace the storage ring 338 into the engagement position or storage sealing mode.

Referring to FIGS. 14A-C, there is shown an alternative optional embodiment of a plunger insertion apparatus 1020, used, e.g., to set the convertible plunger 324 of FIGS. 10-12 in a syringe barrel. As a first step in a method of assembly, as discussed above, one of the traditional methods (e.g., vent tube, vacuum or vacuum assist) may be employed to initially dispose the plunger 324 within a syringe barrel. The apparatus 1020 may be used in a second step to set the ring 338 into engagement mode by displacing it from an initial position on the dispensing platform 348 to a position on the storage platform 344 of the central core 332.

The apparatus 1020 includes a mount 1030 which actuates a tubular structure (similar to a vent tube) that includes an inner and outer component. Namely, an insertion tube 1022 is configured to drive the storage ring 338 distally in direction D while the outer constriction tube 1023 initially surrounds and constrains the outer diameter of the ring 338. Once the ring 338 is disposed about the storage platform 344 of the central core 332, the tube structure retracts (see FIG. 14B) such that the constriction tube 1023 releases the ring 338, enabling the ring 338 contact the barrel wall in the engagement position. The apparatus 1020 further includes a spring 1028, stops 1032 and a plunger positioning rod 1024 which function substantially as described above with respect to like components of the apparatus 1000 of FIG. 13. The mount 1030 initially drives the entire plunger 324 distally in direction D using the plunger positioning rod 1024 until the rim 1026 at the proximal end of the insertion tube 1022 is blocked by the stops 1032, at which point plunger movement ceases. However, the spring 1028 allows the constriction tube 1023 to continue past that point. The constriction tube 1023 first captures the outer diameter of the ring 338 and then moves down to the final position. The insertion tube 1022 moves independently of the mount 1030 to allow for the insertion tube 1022 to engage the storage ring 338 to support it during the phase when the constriction tube 1023 is capturing the sealing ring 338. The insertion tube 1022 remains in place to retain the sealing ring 338 in an engagement position while retracting the constriction tube 1023.

Figure 15A:
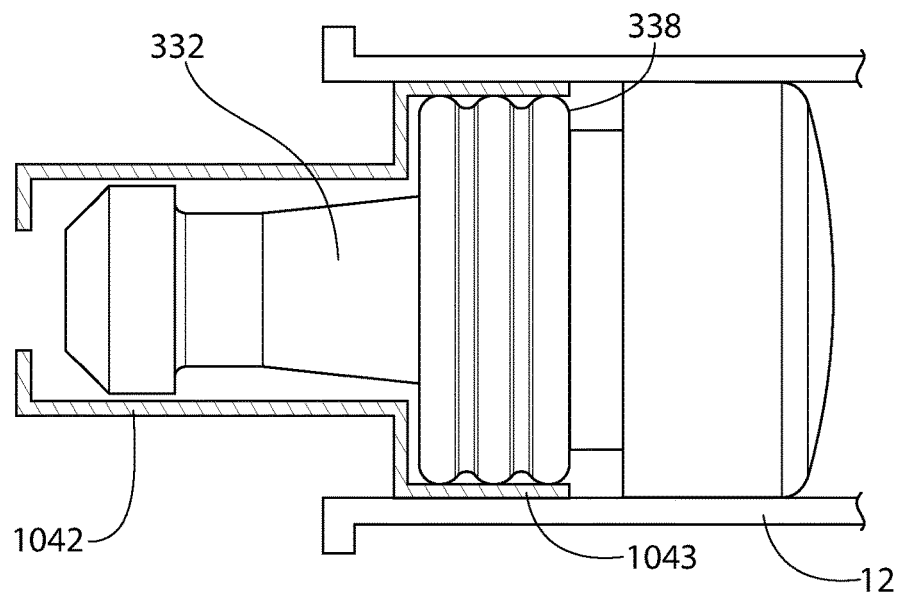
FIG. 15A is a partial schematic illustration of an alternative embodiment of a plunger insertion apparatus, according to an aspect of the invention, for inserting the plunger of FIG. 10 into a medical barrel, wherein the storage ring is set in storage sealing mode.
Figure 15B:
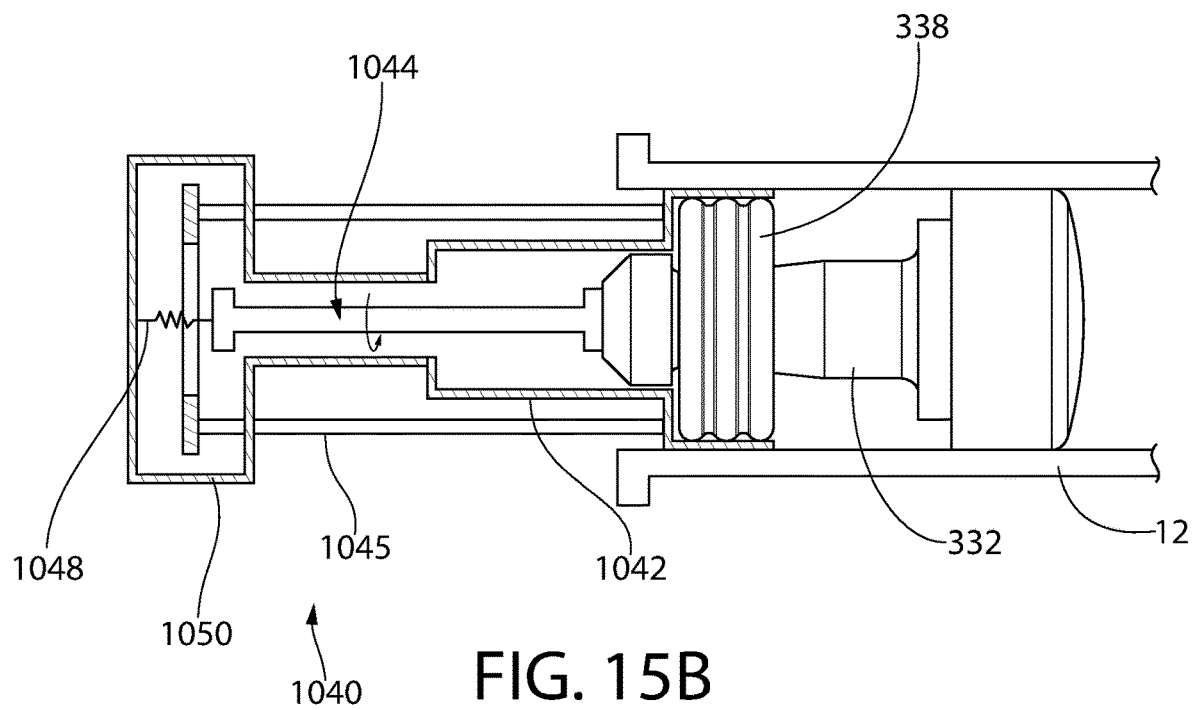
FIG. 15B is a more complete schematic illustration of FIG. 15A, showing additional components of the plunger insertion apparatus, wherein the storage ring is in a pre-storage sealing mode.

Referring to FIGS. 15A and 15B, there is shown an alternative optional embodiment of a plunger insertion apparatus 1040, used, e.g., to set the convertible plunger 324 of FIGS. 10-12 in a syringe barrel. As a first step in a method of assembly, as discussed above, one of the traditional methods (e.g., vent tube, vacuum or vacuum assist) may be employed to initially dispose the plunger 324 within a syringe barrel. The apparatus 1040 may be used in a second step to set the ring 338 into engagement mode by displacing it from an initial position on the dispensing platform 348 to a position on the storage platform 344 of the central core 332.

The outer diameter of the storage ring 338 is initially constrained by the constriction portion 1043 of a removable tubular component 1042. The component 1042 may be placed in position when the plunger 324 is manufactured or at the point of use before insertion into a syringe. If the removable tubular component 1042 is placed in position when the plunger is manufactured, the component 1042 may be disposable. If the removable tubular component 1042 is placed in position at the point of use, the component 1042 may be reusable. Once the storage ring 338 is placed onto the storage platform 344, the removable tubular component 1042 retracts and the storage ring 338 can expand into the engagement position.

As with other embodiments discussed above, the apparatus 1040 includes a mount 1050, spring 1048 and plunger positioning rod 1044. Optionally, the rod 1044 is telescoping to position the plunger 324 and engage the removable tubular component 1042 to remove it. There is further an outer frame 1045 that passes through the removable tubular component 1042 to engage the storage ring 338. An independent motion retains the sealing ring in a desired position while the removable tubular component 1042 is retracted.

Figure 18:
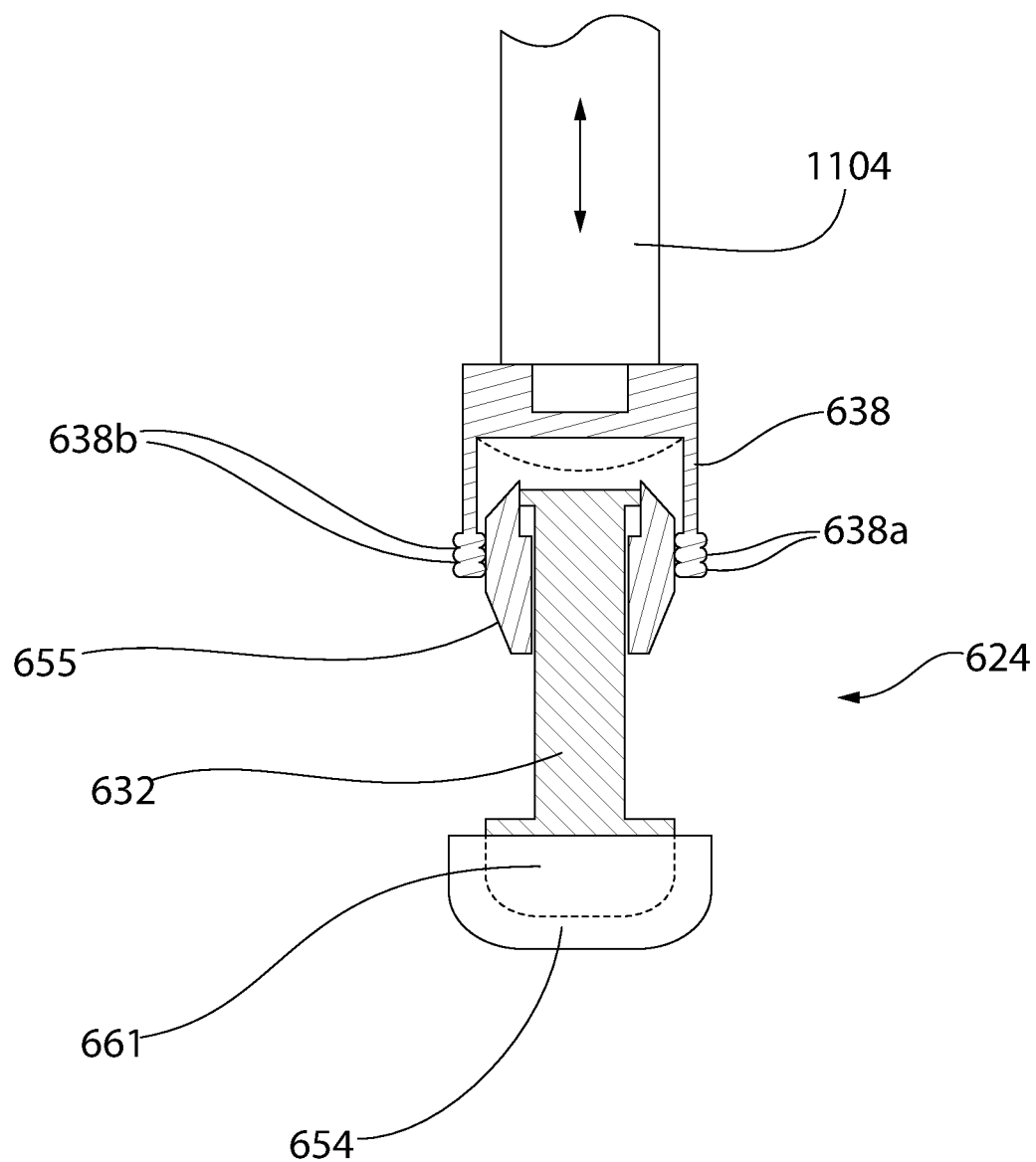
FIG. 18 is a cross-sectional view of an alternative embodiment of a convertible plunger according to an aspect of the invention with an optional plunger insertion apparatus assembling the plunger into a medical barrel.

Referring now to FIG. 18, there is shown an alternative embodiment of a convertible plunger 624. The plunger 624, like the embodiment of FIGS. 10-12, includes a film 656 on a plunger head 654 that is secured to an internal rigid support 661. The plunger 624 also includes a central core 632, but unlike other embodiments disclosed herein, the central core 632 is not exposed to ambient conditions, such as moisture, oxygen or unsterile conditions. In this embodiment, the storage ring 638 covers the proximal end of the central core 632 and also provides gas-tight sealing to protect syringe contents from the ambient environment. The ring 638 includes three ribs 638a with valleys 638b on either side of the middle rib 638a. Such multi ribbed configuration is advantageous for reasons provided above. An internal seal actuator 655 is positioned around a proximal portion of the central core 632 and is surrounded, in part, by the storage ring 638. The seal actuator 655 is configured to slide on the central core 632. The outer profile of the actuator 655 includes two ramped sections (a,c) and a flat section (b) therebetween.

The internal actuator 655 may be assembled onto the central core 632 and the material of the central core 632 may be displaced (e.g., via peening, ultrasonic energy, melting, etc.) over to retain the actuator 655. At that point, the storage ring 338 may be assembled onto the central core 632. The ramp (a) may retain the storage ring 338.

The plunger 624 may be inserted in a barrel initially by vacuum or vacuum assist. To set the ring 638 in engagement position, the ring 638 is displaced distally, which in turn moves the internal seal actuator 655 distally so that the flat section (b) compresses the ribs 638a against the barrel wall. If vacuum assist is used as a method step in assembling the plunger, a telescoping element such as that shown in FIG. 16A (discussed below) may be used to displace the ring 338 in the center initially to position the plunger 624 and then the larger diameter tube to move the actuator 655 into position.

In use, the convertible plunger 624 may be actuated simply by pushing it distally to dispense the syringe contents. The initial movement displaces the actuator 655 further to release the storage ring 638 from engagement position and transition it to dispensing position. Continued movement displaces the plunger distally 624 down the barrel.

Figure 16A:
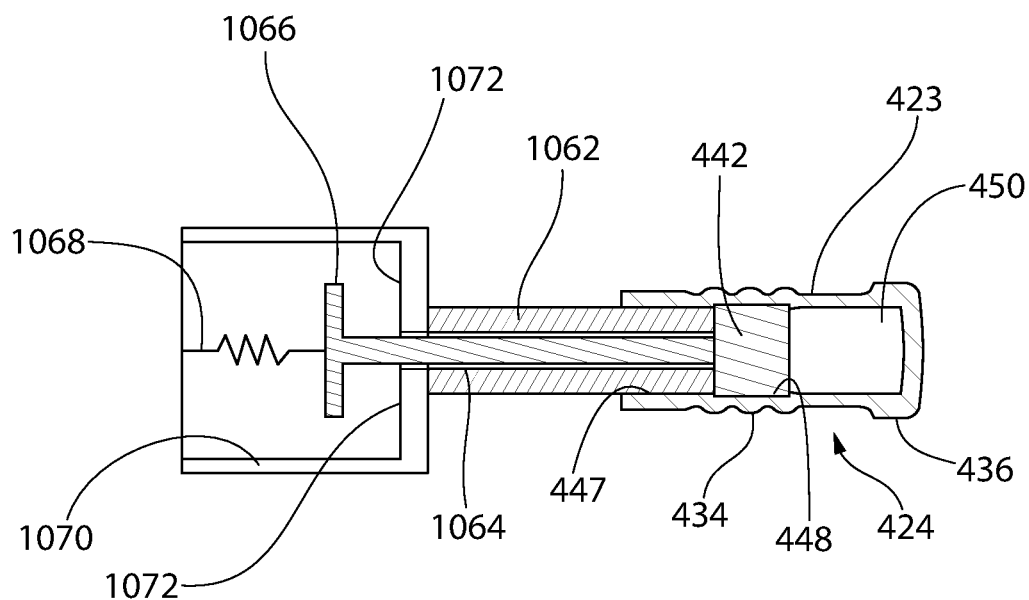
FIG. 16A is a sectional schematic illustration of a plunger insertion apparatus, according to an aspect of the invention, for an exemplary embodiment of an insert and sleeve convertible plunger.
Figure 16B:
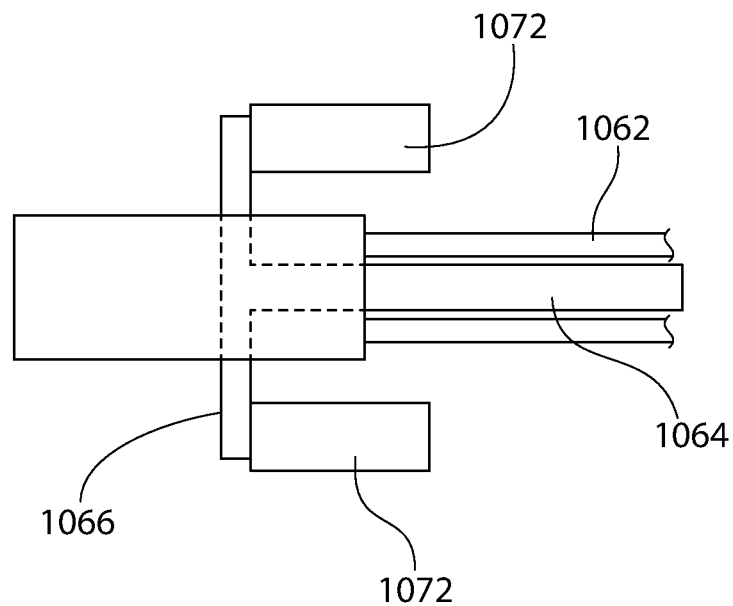
FIG. 16B is a partial schematic illustration of the plunger insertion apparatus of FIG. 16A, oriented 90 degrees from the view shown in FIG. 16A.

As mentioned above, methods and apparatus are also described in this specification for assembling insert and sleeve plunger type embodiments into a syringe barrel. One such apparatus is shown in FIGS. 16A and 16B. The insert and sleeve convertible plunger 424 includes a preferably elastomeric plunger sleeve 423 having a storage sealing section 434 and liquid sealing section 436. The plunger sleeve 423 further comprises internal cavities 447, 448, 450, which are in communication with each other and are configured to receive movable insertion of an insert 442. Cavity 448 is adjacent to the storage sealing section 434. When the plunger 424 is in engagement position, the insert 442 is disposed in the cavity 448 to provide compression of the storage sealing section 434 against a syringe barrel wall. To transition to dispensing mode, the insert 442 is advanced from cavity 448 to cavity 450.

The proximal most cavity or pre-load cavity 447 is the initial location of the insert 442 when assembling the plunger 424 into a syringe barrel. In this position, the plunger does not provide gas-tight compression against the syringe barrel, enabling the plunger 424 to advance distally to a desired point within the syringe. Such insertion may be effectuated with the plunger insertion apparatus 1060. The apparatus includes a mount 1070, spring 1068, central rod 1064, outer sleeve 1062, flanged end 1066 of the central rod 1064 and stops 1072. The rod 1064 may place the plunger 424 in the proper location with a syringe. A collapsing sleeve 1062 continues to move distally after the plunger is positioned. The continued movement moves the insert 442 into cavity 448 where the storage sealing section 434 becomes set in the engagement position for commercial distribution.

Figure 17A:
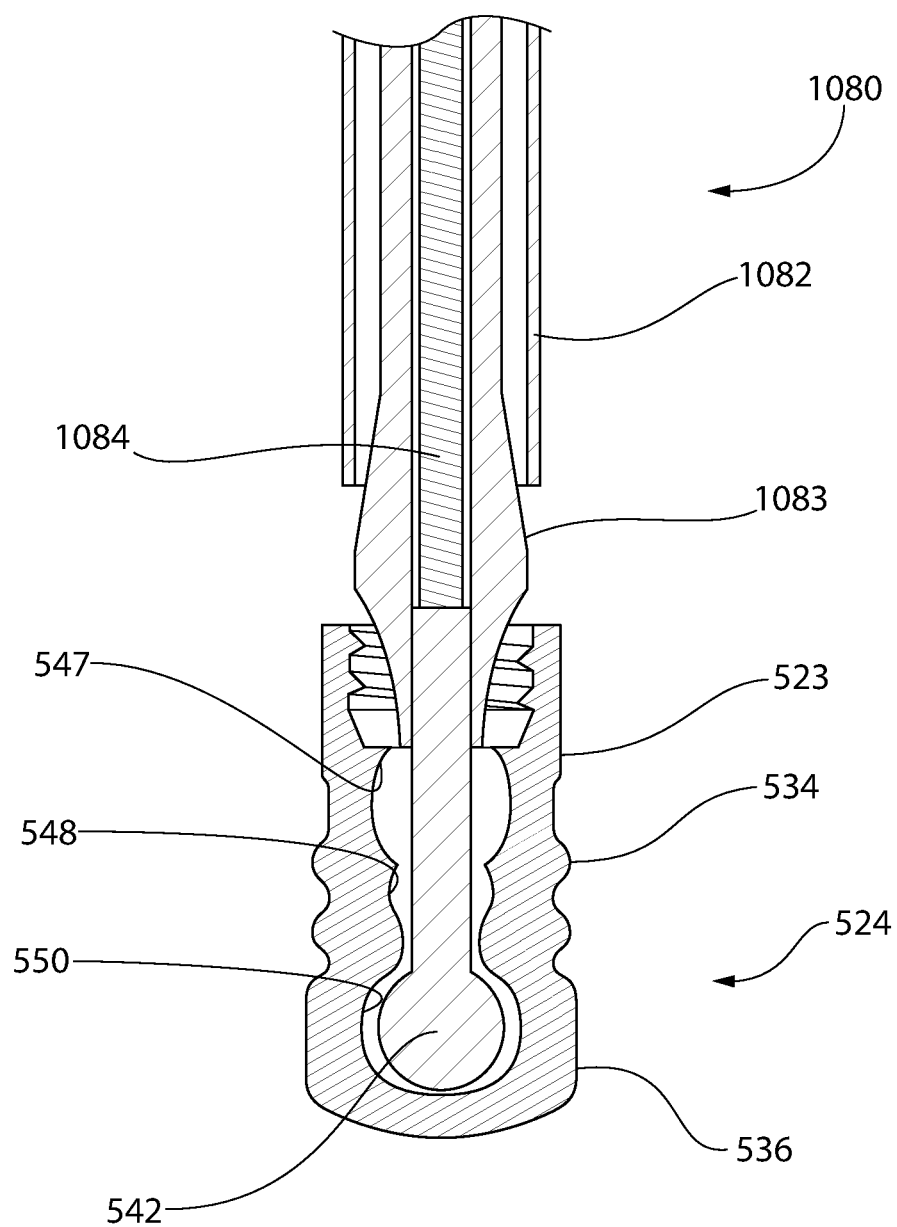
FIG. 17A is a partial cross-sectional view of an alternative plunger insertion apparatus, according to an aspect of the invention, for another exemplary embodiment of an insert and sleeve convertible plunger.
Figure 17B:
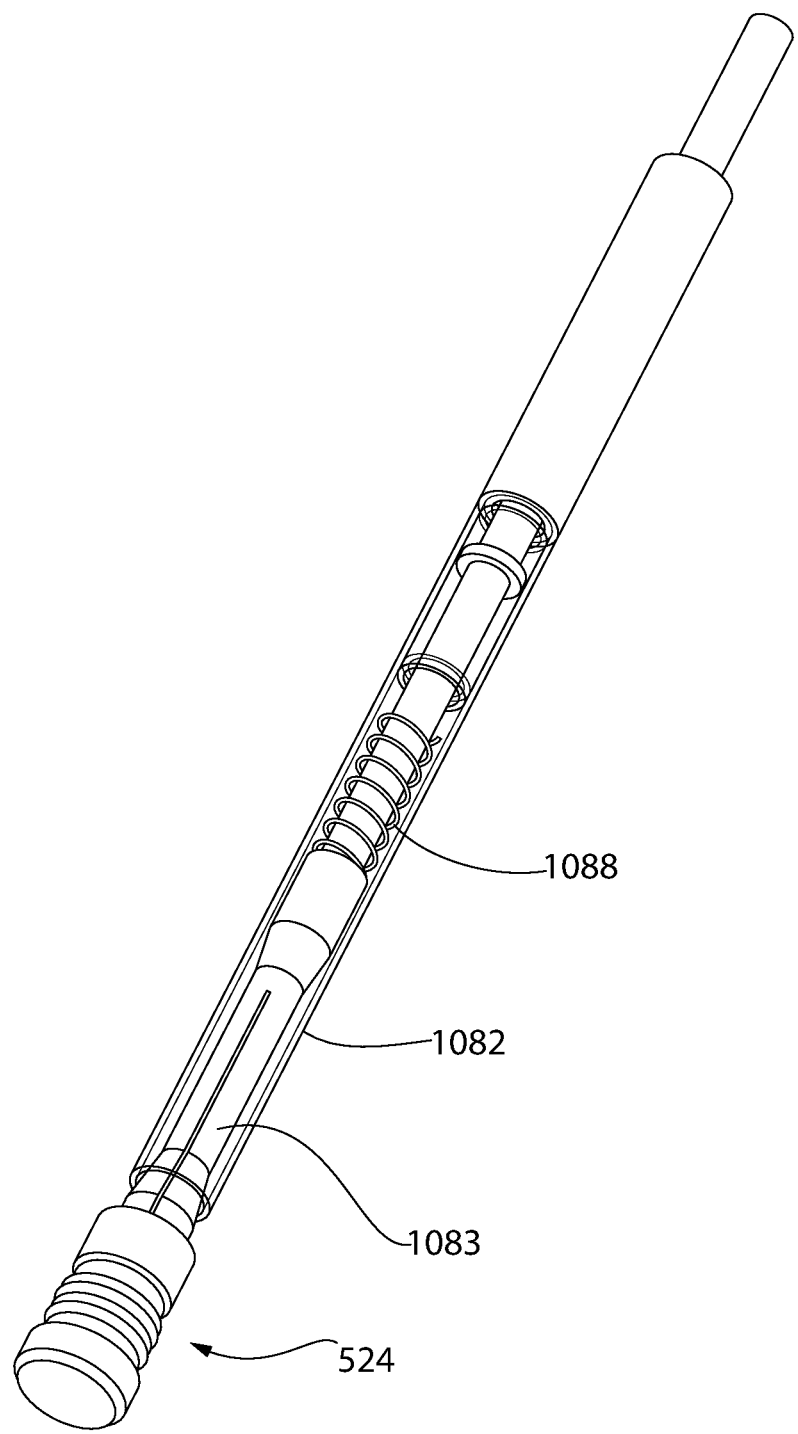
FIG. 17B is a perspective view of the plunger insertion apparatus and plunger of FIG. 17A.

Referring to FIGS. 17A and 17B, there is shown a plunger insertion apparatus 1080 for an insert and sleeve convertible plunger 524. The plunger 524 includes a preferably elastomeric plunger sleeve 523 having a storage sealing section 534 and liquid sealing section 536. The plunger sleeve 523 further comprises internal cavities 547, 548 and 550, which are in communication with each other and are configured to receive movable insertion of an insert 542. Cavity 548 is adjacent to the storage sealing section 534. When the plunger 524 is in engagement position, the insert 542 is disposed in the cavity 548 to provide compression of the storage sealing section 534 against a syringe barrel wall. To transition to dispensing mode, the insert 542 is advanced from cavity 548 to cavity 550.

When initially disposing the plunger 524 within a syringe barrel, the insert 542 is initially positioned in the distal most cavity, 550. In this position, the insert may be advanced in the barrel with the plunger positioning rod 1084 that is disposed with a sleeve 1082 of the apparatus. A gripper 1083 is then used to grasp the proximal end of the insert and retract the insert so that it is positioned within cavity 548, thus generating compression of the storage sealing section 534 against the syringe barrel to put the plunger 524 in an engagement position.

Optionally in any embodiment of convertible plunger according to the invention, the plunger provides a break loose force and glide force below 15 N, optionally below 10 N, optionally below 9 N, optionally below 8 N. optionally below 7 N, optionally below 6 N, optionally below 4 N, optionally between about 2 N and about 5.5 N, optionally between about 2 N and about 4 N, substantially or entirely without the presence of a flowable lubricant between the barrel and the plunger's barrel-contacting surfaces. Optionally in any embodiment of convertible plunger according to the invention, the plunger provides a differential between break loose force and glide force of optionally below 2 N, optionally below 1.5 N, optionally below 1.0 N, optionally below 0.5 N, optionally below 0.4 N, optionally below 0.25 N. Optionally in any embodiment of convertible plunger according to the invention, the plunger provides a differential between break loose force and glide force of optionally below 20%, optionally below 15%, optionally below 12%, optionally below 10%, optionally below 8%, optionally between 2.5% and 6%. These differentials between break loose force and glide force are provided substantially or entirely without the presence of a flowable lubricant between the barrel and the plunger's barrel-contacting surfaces.

In any embodiment, the liquid sealing section (via the plunger head) provides a liquid tight seal and optionally (albeit preferably) CCI. If a CCI level seal for the liquid sealing section is to be provided, the sterile barrier provided by the liquid sealing section may be verified by using both of the following two tests: (1) microbial ingress testing using a liquid immersion technique; and (2) the dye penetration test. The microbial ingress test using a liquid immersion technique involves providing a challenge organism provided in a liquid, immersing the sample container in the liquid while a vacuum is applied to the contents section of the container, and after a designated time, testing to see if the challenge organism migrated past the liquid sealing section. The dye penetration test involves placing a sample container, with the plunger head disposed therein, into a dye bath, applying a vacuum to obtain a manometer reading lower than 635 mmHg for two minutes and visually or using an ultraviolet reading technique, determining whether any of the dye passed through the liquid sealing section. Ultimately, both tests should be passed in order to verify CCI provided by the liquid sealing section.

Absence of Flowable Lubricant in Injectable Drug Product

It has been observed that protein-based drugs can denature or otherwise degrade. A principal way the drug denatures is to unfold and then to cause aggregates to form in the drug product. The primary container can cause protein to denature. One factor that can cause such denaturing is the presence of silicone oil lubricant (a type of flowable lubricant). Droplets of silicone oil can detach from the container wall and interact with the drug. These droplets cause proteins in the liquid to unfold.

A big problem with biologic drugs is the possibility of an immune response by the patient. An immune response can be caused by aggregates (particles) in the drug that are injected into the patient. These aggregates may cause the production of antibodies in the patient that: (1) render the drug ineffective or (2) cause a severe autoimmune response. A small quantity of particles can cause an immune response. The % of proteins that have aggregated in the drug may be very, very small but can cause an immune response. For example, drugs taken by MS and Crohn's Disease patients develop an immune response within 2 years. This requires the patient to stop taking the drug and/or switch drugs.

The number of protein-based drugs has increased significantly over the past five years and this trend will continue. Drug therapies are being used to treat more chronic indications. This means that patients are taking the drugs longer and are more prone to side effects caused by the drug.

Previously, protein drugs were taken for acute indications and side effects were limited.

The amount of contaminants in the drug may increase over the shelf life. The threshold for measuring contaminants is at the detection limit of the instrumentation—so the concentrations are going lower and lower. The concentration of these particles is low ppb/ml, but this may still be enough to cause an immune response. Accordingly, the need to avoid use of flowable lubricants is particularly pressing with biologic drugs, i.e., polypeptide compositions or protein compositions that are provided in prefilled syringes.

In an optional aspect of the invention, a convertible plunger according to any embodiment disclosed herein, which does not require the use of a flowable lubricant between the syringe barrel wall and the barrel-contacting surfaces of the plunger, is particularly beneficial for prefilled syringes containing a polypeptide composition or protein composition. In this way, flowable lubricant, e.g., silicone oil, will not migrate into the drug (and ultimately into the patient) and therefore will not denature the biologic components of the drug composition. As such, shelf life of the biologic drug may be optimized. Moreover, in this way, undesired immune responses by the patient otherwise caused by silicone oil giving rise to aggregates in the drug can be avoided. Thus an "oil-free solution" is particularly desirable for biologics.

Accordingly, in an optional embodiment, the invention is directed to use of a convertible plunger according to any embodiment disclosed herein, disposed in a prefilled syringe. The syringe includes a medical barrel having an inner wall and an injectable drug product, optionally a liquid composition, disposed in a product containing area of the medical barrel, the injectable drug product comprising a polypeptide composition or protein composition that is susceptible to denaturing from interaction with particles generated from a flowable lubricant. The medical barrel has a distal dispensing end for dispensing the injectable drug product and an open proximal end configured for receipt of the convertible plunger. According to an optional embodiment of the invention, the polypeptide composition or protein composition is susceptible to one or more of the following negative effects from interaction with particles generated from a flowable lubricant: denaturing of proteins in the composition; agglomeration of proteins in the composition; degradation of proteins in the composition; triggering an undesired immune response in a patient; and degrading efficacy of the drug product. Flowable lubricant-generated particles are absent from the drug product such that the drug product is not subject to any of the aforementioned negative effects that may otherwise result from interaction with flowable lubricant-generated particles.

The present embodiments are particularly useful for the administration of lyophilized pharmaceuticals, including small molecules and biologicals, such as those presently marketed as lyophilized or powdered drugs for injection. These include, by way of non-limiting examples, ActHIB® vaccine, Aldesleukin, ampicillin, asparaginase, amphotericin B (Amphotec, Amphocin, others), ATryn antithrombin, Bendamustine, Bleomycin, Bortezomib, Carboplatin, Carmustine, Caverject Powder (Alprostadil), Certolizumab (CI-MZIA®), Cefazolin, Cefonicid, Ceftazidime, Ceftriaxone sodium, Cisplatin, Cytarabine, Cytoxan (cyclophosphamide), Dacarbazine, Daunorubicin, Degarelix, Desferrioxamine Mesilate, Doxorubicin (Adriamycin), Epirubicin, Erythrocin lactobionate, estrogen, Gemcitabine, glucagon, human chorionic gonadotropin, human growth hormone, human menopausal gonadotropin (HMG, menotrpin), human plasma, HcG 5000 IU-5 ml, immune globulin (Carimune, Gammagard®), Interferon beta 1a (Avonex), Intron A (interferon alfa-2b), Kogenate FS (recombinant factor VII) Leucovorin calcium, leuproreline, methylprednisolone, Leukine (sargramostim), Menomune® vaccine, MMR and MMRV vaccines, Peginterferon alfa-2b (PegIntron), Remicade® infliximab, Sermorelin/GHRH6-5 ml, somatropin (Genotropin, Saizen®), Sincalide (Kinevac), thiotepa, Vecuronium bromide, Vfend (voriconazole), Vincristine, Varicella vaccines, and Zostavax.

Some excipients are included in powdered or lyophilized products, such as solubilizers or buffers, may be considered functional excipients. Excipients used in various lyophilized formulations include bulking agents, buffering agents, tonicity modifiers, antimicrobial agents, surfactants and co-solvents, and are well-known in the art. See, e.g., Baheti et al., Excipients Used in Lyophilization of Small Molecules, 1 J. Excipients & Food Chem. 41 (2010). Similarly, diluents are well-known in the art, such as water for injection, and often include excipients, e.g., saline or Ringer's solution.

Industry Standards for Testing Aspects of Plunger

Testing of compression setting properties of the plunger assembly may be conducted using methods known in the art, for example, ASTM D395.

Testing of adhesive properties or bonding strength between the film and the plunger may be conducted using methods known in the art, for example, according to ASTM D1995-92(2011) or D1876-08.

Plunger sliding force is the force required to maintain movement of a plunger in a syringe or cartridge barrel, for example during aspiration or dispense. It can advantageously be determined using, e.g., the ISO 7886-1:1993 test known in the art, or to the currently pending published test method to be incorporated into ISO 11040-4. Plunger breakout force, which may be tested using the same method as that for testing plunger sliding force, is the force required to start a stationary plunger moving within a syringe or cartridge barrel. Machinery useful in testing plunger sliding and breakout force is, e.g., an Instron machine using a 50 N transducer.

Testing for extractables, i.e., amount of material that migrates from the plunger into the liquid within the syringe or cartridge, may be conducted using methods set forth in Ph. Eur. 2.9.17 Test for Extractable Volume of Parenteral Preparations, for example.

Testing of container closure integrity (CCI) may be done using a vacuum decay leak detection method, wherein a vacuum his maintained inside of a test volume and pressure rise is measured over time. A large enough pressure rise is an indication that there is flow into the system, which is evidence of a leak. Optionally, the vacuum decay test is implemented over two separate cycles. The first cycle is dedicated to detecting large leaks over a very short duration. A relatively weak vacuum is pulled for the first cycle because if a gross leak is detected, a large pressure differential is not necessary to detect a large pressure rise. Use of a first cycle as described helps to shorten total test time if a gross leak exists. If no leak is detected in the first cycle, a second cycle is run, which complies with ASTM F2338-09 Standard Test Method for Nondestructive Detection of Leaks in Packages by Vacuum Decay Method. The second cycle starts out with a system evaluation to lower the signal to noise ratio in the pressure rise measurements. A relatively strong vacuum is pulled for a long period of time in the second cycle to increase the chance of detecting a pressure rise in the system.

Testing of air leakage past the syringe piston during aspiration may be conducted using methods known in the art, for example, ISO 7886-1:1993.

Testing of liquid leakage at syringe piston under compression may be conducted using methods known in the art, for example, ISO 7886-1:1993.

Convertible Plungers Used In PECVD-Coated Syringe Barrels

In another aspect, the present invention includes use of any embodiments (or combination of embodiments) of plungers according to the invention in syringes having a PECVD coating or PECVD coating set. The syringes may be made from, e.g., glass or plastic. Optionally, the syringe barrel according to any embodiment is made from an injection moldable thermoplastic material that appears clear and glass-like in final form, e.g., a cyclic olefin polymer (COP), cyclic olefin copolymer (COC) or polycarbonate. Such materials may be manufactured, e.g., by injection molding, to very tight and precise tolerances (generally much tighter than achievable with glass). This is a benefit when trying to balance the competing considerations of seal tightness and low plunger force in plunger design.

This section of the disclosure focuses primarily on prefilled syringes as a preferred implementation of optional aspects of the invention. Again, however, it should be understood that the present invention may include any parenteral container that utilizes a plunger, such as syringes, cartridges, auto-injectors, prefilled syringes, prefilled cartridges or vials.

For some applications, it may be desired to provide one or more coatings or layers to the interior wall of a parenteral container to modify the properties of that container. For example, one or more coatings or layers may be added to a parenteral container, e.g., to improve the barrier properties of the container and prevent interaction between the container wall (or an underlying coating) and drug product held within the container. Such coatings or layers may be constructed in accordance with the teachings of co-pending PCT Application PCT/US2014/023813, filed on Mar. 11, 2014, which is incorporated by reference herein in its entirety.

Figure 1A:
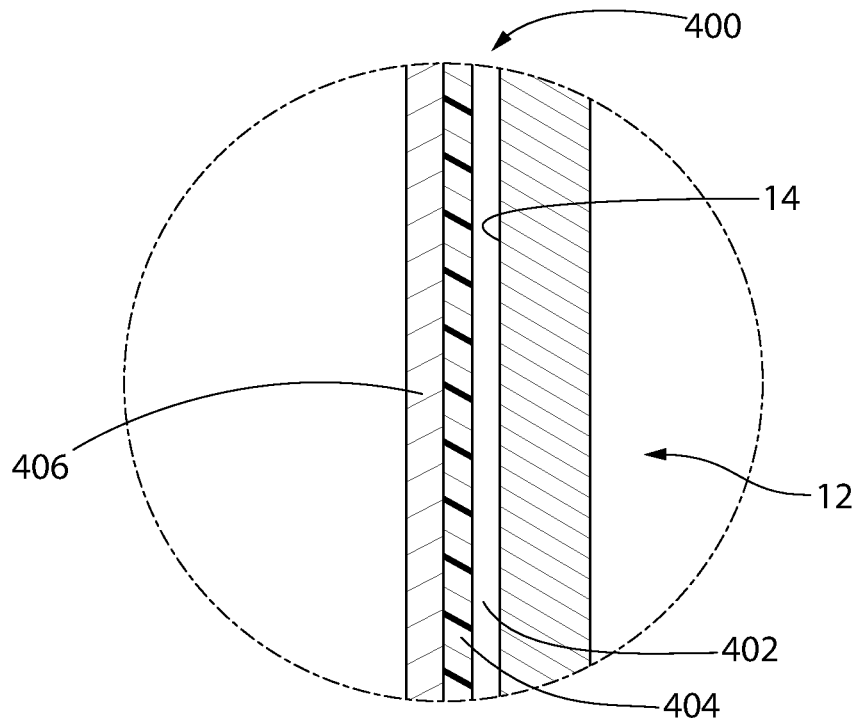
FIG. 1A is an enlarged sectional view of a first alternative embodiment of the inner surface of the syringe of FIG. 1, comprising a tri-layer coating set disposed thereon.
Figure 1B:
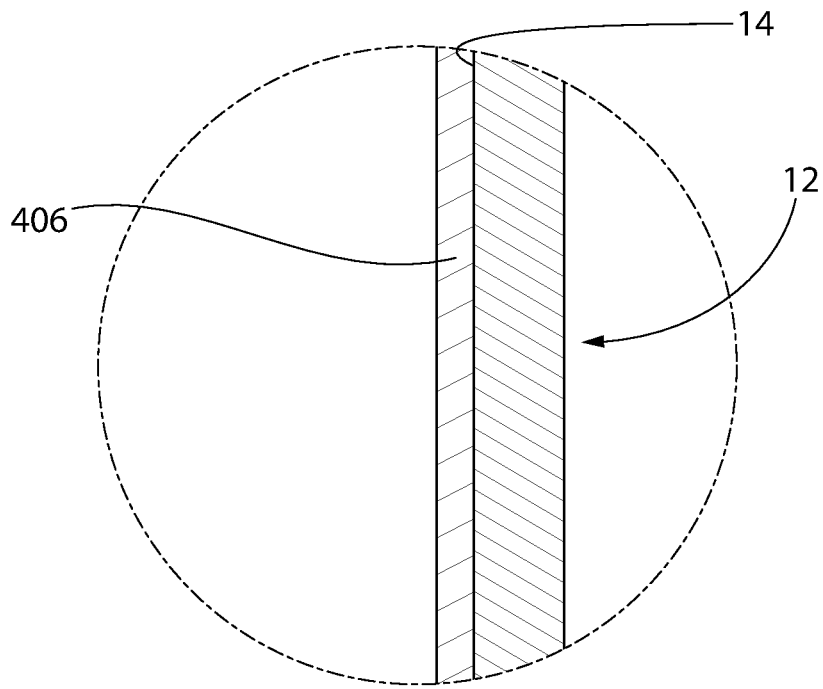
FIG. 1B is an enlarged sectional view of a second alternative embodiment of the inner surface of the syringe of FIG. 1, comprising an organo-siloxane coating disposed thereon.

For example, as shown in FIG. 1A, which is a first alternative embodiment of an enlarged sectional view of the barrel 12 of the syringe 10 of FIG. 1, the inner surface 14 of the barrel 12 may include a coating set 400 comprising one or more coatings or layers. The barrel 12 may include at least one tie coating or layer 402, at least one barrier coating or layer 404, and at least one organo-siloxane coating or layer 406. The organo-siloxane coating or layer 406 preferably has pH protective properties. This embodiment of the coating set 400 is referred to herein as a "tri-layer coating set" in which the barrier coating or layer 404 of $SiO_x$, is protected against contents having a pH otherwise high enough to remove it by being sandwiched between the pH protective organo-siloxane coating or layer 406 and the tie coating or layer 402. The contemplated thicknesses of the respective layers in nanometers (preferred ranges in parentheses) are given in the following Tri-layer Thickness Table:

| Tri-layer Thickness Table | | |
|---|---|---|
| Adhesion (nm) | Barrier (nm) | Protection (nm) |
| 5-100 | 20-200 | 50-500 |
| (5-20) | (20-30) | (100-200) |

Properties and compositions of each of the coatings that make up the tri-layer coating set are now described.

The tie coating or layer 402 has at least two functions. One function of the tie coating or layer 402 is to improve adhesion of a barrier coating or layer 404 to a substrate (e.g., the inner surface 14 of the barrel 12), in particular a thermoplastic substrate, although a tie layer can be used to improve adhesion to a glass substrate or to another coating or layer. For example, a tie coating or layer, also referred to as an adhesion layer or coating can be applied to the substrate and the barrier layer can be applied to the adhesion layer to improve adhesion of the barrier layer or coating to the substrate.

Another function of the tie coating or layer 402 has been discovered: a tie coating or layer 402 applied under a barrier coating or layer 404 can improve the function of a pH protective organo-siloxane coating or layer 406 applied over the barrier coating or layer 404.

The tie coating or layer 402 can be composed of, comprise, or consist essentially of $SiO_xC_y$, in which x is between 0.5 and 2.4 and y is between 0.6 and 3. Alternatively, the atomic ratio can be expressed as the formula $Si_wO_xC_y$. The atomic ratios of Si, O, and C in the tie coating or layer 402 are, as several options:

Si 100: O 50-150: C 90-200 (i.e. w=1, x=0.5 to 1.5, y=0.9 to 2);

Si 100: O 70-130: C 90-200 (i.e. w=1, x=0.7 to 1.3, y=0.9 to 2)

Si 100: O 80-120: C 90-150 (i.e. w=1, x=0.8 to 1.2, y=0.9 to 1.5)

Si 100: O 90-120: C 90-140 (i.e. w=1, x=0.9 to 1.2, y=0.9 to 1.4), or

Si 100: O 92-107: C 116-133 (i.e. w=1, x=0.92 to 1.07, y=1.16 to 1.33).

The atomic ratio can be determined by XPS. Taking into account the H atoms, which are not measured by XPS, the tie coating or layer 402 may thus in one aspect have the formula $Si_wO_xC_yH_z$ (or its equivalent $SiO_xC_y$), for example where w is 1, x is from about 0.5 to about 2.4, y is from about 0.6 to about 3, and z is from about 2 to about 9. Typically, a tie coating or layer 402 would hence contain 36% to 41% carbon normalized to 100% carbon plus oxygen plus silicon.

The barrier coating or layer 404 for any embodiment defined in this specification (unless otherwise specified in a particular instance) is a coating or layer, optionally applied by PECVD as indicated in U.S. Pat. No. 7,985,188. The barrier coating preferably is characterized as a "$SiO_x$" coating, and contains silicon, oxygen, and optionally other elements, in which x, the ratio of oxygen to silicon atoms, is from about 1.5 to about 2.9. The thickness of the $SiO_x$ or other barrier coating or layer can be measured, for example, by transmission electron microscopy (TEM), and its composition can be measured by X-ray photoelectron spectroscopy (XPS). The barrier layer is effective to prevent oxygen, carbon dioxide, or other gases from entering the container and/or to prevent leaching of the pharmaceutical material into or through the container wall.

Preferred methods of applying the barrier 404 layer and tie layer 402 to the inner surface 14 of the barrel 12 is by plasma enhanced chemical vapor deposition (PECVD), such as described in, e.g., U.S. Pat. App. Pub. No. 20130291632, which is incorporated by reference herein in its entirety.

The Applicant has found that barrier layers or coatings of $SiO_x$ are eroded or dissolved by some fluids, for example aqueous compositions having a pH above about 5. Since coatings applied by chemical vapor deposition can be very thin—tens to hundreds of nanometers thick—even a relatively slow rate of erosion can remove or reduce the effectiveness of the barrier layer in less time than the desired shelf life of a product package. This is particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the $SiO_x$ coating. Optionally, this problem can be addressed by protecting the barrier coating or layer, or other pH sensitive material, with a pH protective organo-siloxane coating or layer.

Optionally, the pH protective organo-siloxane coating or layer 406 can be composed of, comprise, or consist essentially of $Si_wO_xC_yH_z$ (or its equivalent $SiO_xC_y$) or $Si_wN_xC_yH_z$ or its equivalent $SiN_xC_y$). The atomic ratio of Si:O:C or Si:N:C can be determined by XPS (X-ray photoelectron spectroscopy). Taking into account the H atoms, the pH protective coating or layer may thus in one aspect have the formula $Si_3O_xC_yH_z$, or its equivalent $SiO_xC_y$, for example where w is 1, x is from about 0.5 to about 2.4, y is from about 0.6 to about 3, and z is from about 2 to about 9.

Typically, expressed as the formula $Si_wO_xC_y$, the atomic ratios of Si, O, and C are, as several options:
- Si 100: O 50-150: C 90-200 (i.e. w=1, x=0.5 to 1.5, y=0.9 to 2);
- Si 100: O 70-130: C 90-200 (i.e. w=1, x=0.7 to 1.3, y=0.9 to 2)
- Si 100: O 80-120: C 90-150 (i.e. w=1, x=0.8 to 1.2, y=0.9 to 1.5)
- Si 100: O 90-120: C 90-140 (i.e. w=1, x=0.9 to 1.2, y=0.9 to 1.4)
- Si 100: O 92-107: C 116-133 (i.e. w=1, x=0.92 to 1.07, y=1.16 to 1.33), or
- Si 100: O 80-130: C 90-150.

Alternatively, the organo-siloxane coating or layer can have atomic concentrations normalized to 100% carbon, oxygen, and silicon, as determined by X-ray photoelectron spectroscopy (XPS) of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

Optionally, the atomic concentration of carbon in the pH protective coating or layer 406, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer 406 can be increased in comparison to the organosilicon precursor, and/or the atomic ratio of oxygen to silicon can be decreased in comparison to the organosilicon precursor.

An exemplary empirical composition for a pH protective coating according to the present invention is $SiO_{1.3}C_{0.8}H_{3.6}$.

Optionally in any embodiment, the pH protective coating or layer 406 comprises, consists essentially of, or consists of PECVD applied silicon carbide.

Optionally in any embodiment, the pH protective coating or layer 406 is applied by employing a precursor comprising, consisting essentially of, or consisting of a silane. Optionally in any embodiment, the silane precursor comprises, consists essentially of, or consists of any one or more of an acyclic or cyclic silane, optionally comprising, consisting essentially of, or consisting of any one or more of silane, trimethylsilane, tetramethylsilane, Si2-Si4 silanes, triethyl silane, tetraethyl silane, tetrapropylsilane, tetrabutylsilane, or octamethylcyclotetrasilane, or tetramethylcyclotetrasilane.

Optionally in any embodiment, the pH protective coating or layer 406 comprises, consists essentially of, or consists of PECVD applied amorphous or diamond-like carbon. Optionally in any embodiment, the amorphous or diamond-like carbon is applied using a hydrocarbon precursor. Optionally in any embodiment, the hydrocarbon precursor comprises, consists essentially of, or consists of a linear, branched, or cyclic alkane, alkene, alkadiene, or alkyne that is saturated or unsaturated, for example acetylene, methane, ethane, ethylene, propane, propylene, n-butane, i-butane, butane, propyne, butyne, cyclopropane, cyclobutane, cyclohexane, cyclohexene, cyclopentadiene, or a combination of two or more of these. Optionally in any embodiment, the amorphous or diamond-like carbon coating has a hydrogen atomic percent of from 0.1% to 40%, alternatively from 0.5% to 10%, alternatively from 1% to 2%, alternatively from 1.1 to 1.8%.

Optionally in any embodiment, the pH protective coating or layer 406 comprises, consists essentially of, or consists of PECVD applied SiNb. Optionally in any embodiment, the PECVD applied SiNb is applied using a silane and a nitrogen-containing compound as precursors. Optionally in any embodiment, the silane is an acyclic or cyclic silane, optionally comprising, consisting essentially of, or consisting of silane, trimethylsilane, tetramethylsilane, Si2-Si4 silanes, triethylsilane, tetraethylsilane, tetrapropylsilane, tetrabutylsilane, octamethylcyclotetrasilane, or a combination of two or more of these. Optionally in any embodiment, the nitrogen-containing compound comprises, consists essentially of, or consists of any one or more of: nitrogen gas, nitrous oxide, ammonia or a silazane. Optionally in any embodiment, the silazane comprises, consists essentially of, or consists of a linear silazane, for example hexamethylene disilazane (HMDZ), a monocyclic silazane, a polycyclic silazane, a polysilsesquiazane, or a combination of two or more of these.

Optionally in any embodiment, the PECVD for the pH protective coating or layer 406 is carried out in the substantial absence or complete absence of an oxidizing gas. Optionally in any embodiment, the PECVD for the pH protective coating or layer 406 is carried out in the substantial absence or complete absence of a carrier gas.

Optionally an FTIR absorbance spectrum of the pH protective coating or layer 406 SiOxCyHz has a ratio greater than 0.75 between the maximum amplitude of the Si—O—Si symmetrical stretch peak normally located between about 1000 and 1040 cm-1, and the maximum amplitude of the Si—O—Si asymmetric stretch peak normally located between about 1060 and about 1100 cm-1. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment.

Optionally, in any embodiment the pH protective coating or layer 406, in the absence of the medicament, has a non-oily appearance. This appearance has been observed in some instances to distinguish an effective pH protective coating or layer 406 from a lubricity layer (e.g., as described in U.S. Pat. No. 7,985,188), which in some instances has been observed to have an oily (i.e. shiny) appearance.

The pH protective coating or layer optionally can be applied by plasma enhanced chemical vapor deposition (PECVD) of a precursor feed comprising an acyclic siloxane, a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors. Some particular, non-limiting precursors contemplated for such use include octamethylcyclotetrasiloxane (OMCTS).

Optionally, an FTIR absorbance spectrum of the pH protective coating or layer 406 of composition $SiO_xC_yH_z$ has a ratio greater than 0.75 between the maximum amplitude of the Si—O—Si symmetrical stretch peak between about 1000 and 1040 cm-1, and the maximum amplitude of the Si—O—Si asymmetric stretch peak between about 1060 and about 1100 cm-1.

Other precursors and methods can be used to apply the pH protective coating or layer 406 or passivating treatment. For example, hexamethylene disilazane (HMDZ) can be used as the precursor. HMDZ has the advantage of containing no oxygen in its molecular structure. This passivation treatment is contemplated to be a surface treatment of the SiOx barrier layer with HMDZ. To slow down and/or eliminate the decomposition of the silicon dioxide coatings at silanol bonding sites, the coating must be passivated. It is contemplated that passivation of the surface with HMDZ (and optionally application of a few mono layers of the HMDZ-derived coating) will result in a toughening of the surface against dissolution, resulting in reduced decomposition. It is contemplated that HMDZ will react with the —OH sites that are present in the silicon dioxide coating, resulting in the evolution of NH3 and bonding of S—(CH3)3 to the silicon (it is contemplated that hydrogen atoms will be evolved and bond with nitrogen from the HMDZ to produce NH3).

Another way of applying the pH protective coating or layer is to apply as the pH protective coating or layer an amorphous carbon or fluorocarbon coating, or a combination of the two.

Amorphous carbon coatings can be formed by PECVD using a saturated hydrocarbon, (e.g. methane or propane) or an unsaturated hydrocarbon (e.g. ethylene, acetylene) as a precursor for plasma polymerization. Fluorocarbon coatings can be derived from fluorocarbons (for example, hexafluoroethylene or tetrafluoroethylene). Either type of coating, or a combination of both, can be deposited by vacuum PECVD or atmospheric pressure PECVD. It is contemplated that that an amorphous carbon and/or fluorocarbon coating will provide better passivation of an SiOx barrier layer than a siloxane coating since an amorphous carbon and/or fluorocarbon coating will not contain silanol bonds.

It is further contemplated that fluorosilicon precursors can be used to provide a pH protective coating or layer over a SiOx barrier layer. This can be carried out by using as a precursor a fluorinated silane precursor such as hexafluorosilane and a PECVD process. The resulting coating would also be expected to be a non-wetting coating.

Yet another coating modality contemplated for protecting or passivating a SiOx barrier layer is coating the barrier layer using a polyamidoamine epichlorohydrin resin. For example, the barrier coated part can be dip coated in a fluid polyamidoamine epichlorohydrin resin melt, solution or dispersion and cured by autoclaving or other heating at a temperature between 60 and 100° C. It is contemplated that a coating of polyamidoamine epichlorohydrin resin can be preferentially used in aqueous environments between pH 5-8, as such resins are known to provide high wet strength in paper in that pH range. Wet strength is the ability to maintain mechanical strength of paper subjected to complete water soaking for extended periods of time, so it is contemplated that a coating of polyamidoamine epichlorohydrin resin on a SiOx barrier layer will have similar resistance to dissolution in aqueous media. It is also contemplated that, because polyamidoamine epichlorohydrin resin imparts a lubricity improvement to paper, it will also provide lubricity in the form of a coating on a thermoplastic surface made of, for example, COC or COP.

Even another approach for protecting a SiOx layer is to apply as a pH protective coating or layer a liquid-applied coating of a polyfluoroalkyl ether, followed by atmospheric plasma curing the pH protective coating or layer. For example, it is contemplated that the process practiced under the trademark TriboGlide® can be used to provide a pH protective coating or layer 406 that is also provides lubricity.

Thus, a pH protective coating for a thermoplastic syringe wall according to an aspect of the invention may comprise, consist essentially of, or consist of any one of the following: plasma enhanced chemical vapor deposition (PECVD) applied silicon carbide having the formula $SiO_xC_yH_z$, in which x is from 0 to 0.5, alternatively from 0 to 0.49, alternatively from 0 to 0.25 as measured by X ray photo-electron spectroscopy (XPS), y is from about 0.5 to about 1.5, alternatively from about 0.8 to about 1.2, alternatively about 1, as measured by XPS, and z is from 0 to 2 as measured by Rutherford Backscattering Spectrometry (RBS), alternatively by Hydrogen Forward Scattering Spectrometry (HFS); or PECVD applied amorphous or diamond-like carbon, $CH_z$, in which z is from 0 to 0.7, alternatively from 0.005 to 0.1, alternatively from 0.01 to 0.02; or PECVD applied $SiN_b$, in which b is from about 0.5 to about 2.1, alternatively from about 0.9 to about 1.6, alternatively from about 1.2 to about 1.4, as measured by XPS.

PECVD apparatus suitable for applying any of the PECVD coatings or layers described in this specification, including the tie coating or layer, the barrier coating or layer or the organo-siloxane coating or layer, is shown and described in U.S. Pat. No. 7,985,188 and U.S. Pat. App. Pub. No. 20130291632. This apparatus optionally includes a vessel holder, an inner electrode, an outer electrode, and a power supply. A vessel seated on the vessel holder defines a plasma reaction chamber, optionally serving as its own vacuum chamber. Optionally, a source of vacuum, a reactant gas source, a gas feed or a combination of two or more of these can be supplied. Optionally, a gas drain, not necessarily including a source of vacuum, is provided to transfer gas to or from the interior of a vessel seated on the port to define a closed chamber.

It is contemplated that syringes having a plunger-contacting inner surface comprising an organo-siloxane coating, without a separate discrete lubricity coating or substantially without the presence of a flowable lubricant, may still provide adequate lubricity for plunger advancement. As used herein, "substantially without the presence of a flowable lubricant," means that a flowable lubricant (e.g., PDMS) is not provided to a syringe barrel in amounts that would contribute to the lubricity of the plunger-syringe system. Since it is sometimes the practice to use a flowable lubricant when handling plungers prior to assembling them into syringes, "substantially without the presence of a flowable lubricant" in some cases may contemplate the presence of trace amounts of such lubricant as a result of such handling practices.

Accordingly, in one aspect, the invention is directed to an organo-siloxane coating on the inner surface of a parenteral container which provides lubricious properties conducive to acceptable plunger operation. The organo-siloxane coating may, for example, be any embodiment of the pH protective coating discussed above. The organo-siloxane coating may be applied directly to the interior wall of the container or as a top layer on a multi-layer coating set, e.g., the tri-layer coating set discussed above. Preferably, this embodiment would obviate the need for a discrete lubricity coating, e.g., as described in U.S. Pat. No. 7,985,188 or a flowable lubricant, e.g., silicone oil.

The organo-siloxane coating can optionally provide multiple functions: (1) a pH resistant layer that protects an underlying layer or underlying polymer substrate from drug products having a pH from 4-10, optionally from 5-9; (2) a drug contact surface that minimizes aggregation, extractables and leaching; (3) in the case of a protein-based drug, reduced protein binding on the container surface; and (4) a lubricating layer, e.g., to facilitate plunger advancement when dispensing contents of a syringe.

Use of an organo-siloxane coating on a polymer-based container as the contact surface for a plunger provides distinct advantages. Plastic syringes and cartridges may be injection molded to tighter tolerances than their glass counterparts. It is contemplated that the dimensional precision achievable through injection molding allows optimization of the inside diameter of a syringe to provide sufficient compression to the plunger for CCI and gas-tightness on the one hand, while not over-compressing the plunger so as to provide desired plunger force upon administration of the drug product. Optimally, this would eliminate or dramatically reduce the need for lubricating the syringe or cartridge with a flowable lubricant or a discrete lubricity coating, thus reducing manufacturing complexity and avoiding problems associated with silicone oil.

Various aspects of the invention will be illustrated in more detail with reference to the following Examples, but it should be understood that the present invention is not deemed to be limited thereto.

EXAMPLES

Example 1: Low and Consistent $F_i$ and $F_m$

In this example, it is demonstrated how convertible plungers according to an aspect of the present invention achieved extraordinarily low and consistent breakout force $F_i$ and maintenance force $F_m$ with only a very slight difference in average $F_i$ versus $F_m$. Most notably, these forces were achieved without the presence of flowable lubricant between the syringe barrel and barrel-contacting surfaces of the plunger. These results are especially surprising since the plunger provides robust CCI and gas-tight sealing configured to protect the sterility and quality of contents within the syringe over a typical shelf-life of a prefilled syringe (see Example 2, below).

A group of eighteen plungers having the configuration of the convertible plunger 324 of FIGS. 10-12 were assembled and set into storage sealing mode within plastic syringes having tri-layer coating sets 400 (FIG. 1A) deposited on the inner surfaces thereof. The syringes were filled with water for injection. Each of the plungers were actuated to transition from storage sealing mode to dispensing mode and then were advanced distally down each syringe barrel to dispense the water.

Figure 19A:
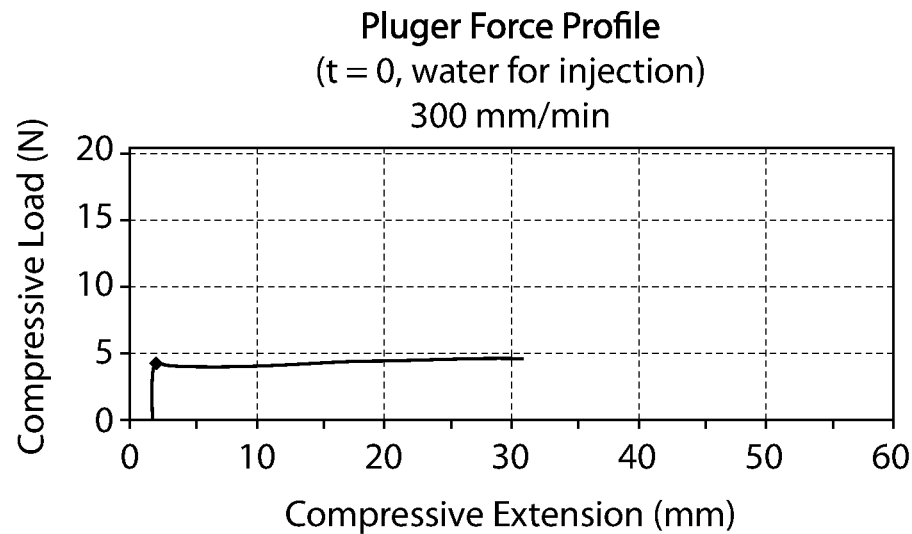
FIG. 19A is a chart detailing the average plunger force profile of plungers according to an embodiment of the present invention, as discussed in Example 1 herein.
Figure 19B:
FIG. 19B is a chart of the raw data for plunger force of the eighteen plungers that were tested, as discussed in Example 1 herein.

FIGS. 19A and 19B graphically illustrate the plunger force results of these tests. FIG. 19B provides the raw data points comparing $F_i$ (left) to $F_m$ (right). As that chart shows, the forces between $F_i$ versus $F_m$ were substantially similar and very low. Even the highest force readings on both sides were under 7N and the average forces were approximately 5N. Moreover, the average difference between $F_i$ and $F_m$ was only about 0.5N. In practical terms, such a differential between $F_i$ and $F_m$ is virtually unnoticeable to a syringe handler or a patient receiving an injection therefrom. FIG. 19A illustrates the average plunger force profile along a 30 mm travel distance in the syringe barrel, again showing an average force of about 5N, which remained very consistent between initiation and glide over the length of the barrel.

In terms of percentages, the average breakout force being about 5.5 N with the average glide force being about 5.0 N, that equates to less than a 10% differential between average $F_i$ and $F_m$.

Figure 20:
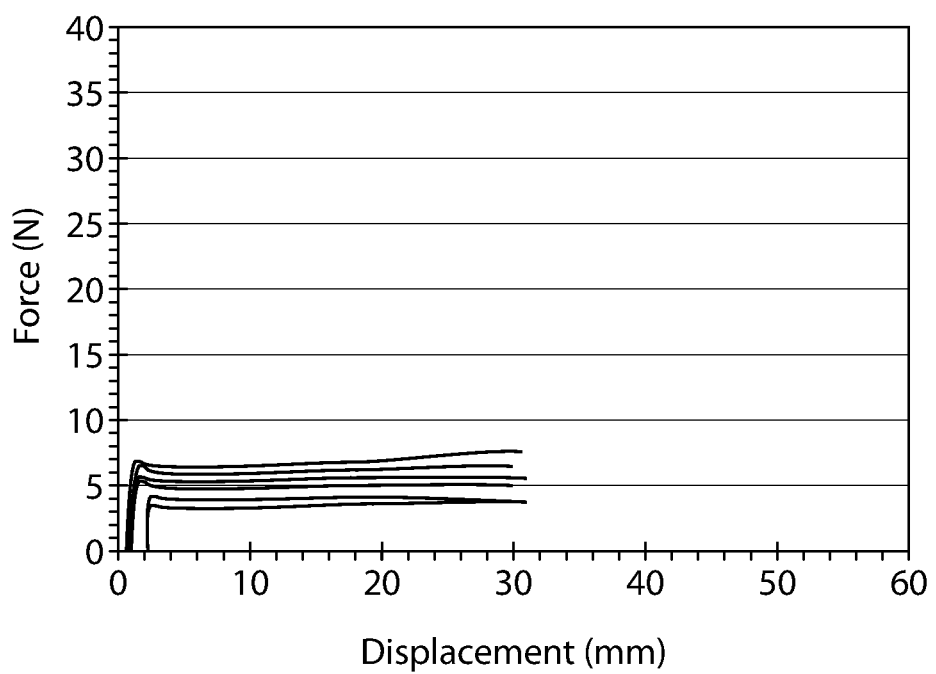
FIG. 20 is a chart of plunger force, discussed also in Example 1, for another set of similarly configured plungers and syringes as those tested and described with respect to FIGS. 19A and 19B.

A separate group of eight plungers and syringes having essentially the same configuration as their counterparts described with respect to FIGS. 19A and 19B, except without liquid in the syringe (i.e., dry) were also subjected to the same plunger force testing. This separate group of plungers demonstrated plunger forces generally between 4.3 N to 7.5 N in empty or dry syringes, as shown in FIG. 20.

The foregoing results demonstrate that the invention can be used to deliver injectable medications to a patient without applying too much pressure and without dramatic changes in the amount of force necessary from initial actuation of the plunger through completion of delivery. Moreover, this may be achieved without flowable lubricant between the plunger and syringe wall. This is a notable achievement.

Example 2: CCI Testing Using Vacuum Decay

The previous example demonstrated the surprisingly low and consistent plunger force that plungers, according to an aspect of the invention, are capable of providing. The present example tested the "competing consideration" of CCI ("competing' with respect to plunger force, as discussed in the Background section above). CCI was tested using the vacuum decay method, as discussed above under the subsection heading, "Industry Standards for Testing Aspects of Plunger."

Plungers subjected to this test had the configuration of the convertible plunger 324 of FIGS. 10-12 and were assembled and set into storage sealing mode within plastic syringes having tri-layer coating sets 400 (FIG. 1A) deposited on the inner surfaces thereof. The particular focus with this test—aside from testing plunger CCI generally—was to determine any correlation between plunger shaft diameter and CCI. The plunger shaft diameter refers to (see FIG. 12) diameter of the annular storage platform 344 of the central core 332, supporting the storage ring 338 in the engagement position.

Five sets of plungers respectively having shaft diameters of 3.25 mm, 3.29 mm, 3.43 mm, 3.51 mm, 3.56 mm, 3.61 mm, 3.68 mm and 3.71 mm were tested in standard 6.48 mm syringe barrels using the vacuum decay method. The results demonstrated that every plunger passed except for one plunger out of four having a 3.25 mm shaft diameter. While thicker shaft diameter may increase the likelihood of providing CCI, it may simultaneously affect plunger force. Thus, a balance must be struck to manage these competing considerations.

Example 3: High Altitude Testing of Convertible Plunger

When prefilled syringes are filled with liquid contents, a gas bubble is typically formed therein. One concern with prefilled syringes is that in their transport, shifts in temperature and pressure (e.g. from changes in altitude) present a possible risk of undesirably displacing the plunger proximately, causing it to potentially contact unsterile portions of the syringe. For example, reduced pressure at high altitudes (e.g., when the product is in a plane or truck driving through a mountain pass) may cause plunger movement and provide a pathway for microbial ingress as the plunger returns to its original position when the reduced pressure is removed.

As altitude increases and pressure drops, this risk of plunger movement and resulting contamination increases. A cabin in a commercial aircraft is typically pressurized to replicate pressure at 8,000 feet altitude. Trucks driving through a mountain pass may be exposed to altitudes as high as 12,000 feet. Packaged products in non-pressurized holds, such as in feeder aircraft, can be exposed to altitudes as high as 16,000-19,000 feet.

In this example, seal movement of the plunger was assessed using vacuum pressure. A plunger was placed into a syringe, the storage ring was set into engagement position and then placed on the test fixture. A vacuum was generated at the flange end of the syringe to replicate air shipment. The test reproduced conditions of 20,000 feet altitude for a period of 16 hours. These would be regarded as exceptionally severe conditions for transport. Surprisingly, no movement of the plunger or the storage ring was observed under such conditions. This test provided results that substantially exceed the ASTM Standard D6653/D6653M-13 Standard Test method for Determining the Effects of High Altitude on Package System by Vacuum Method, which requires positive results at 14,000 to 16,000 feet for a period of one hour.

Figure 25:
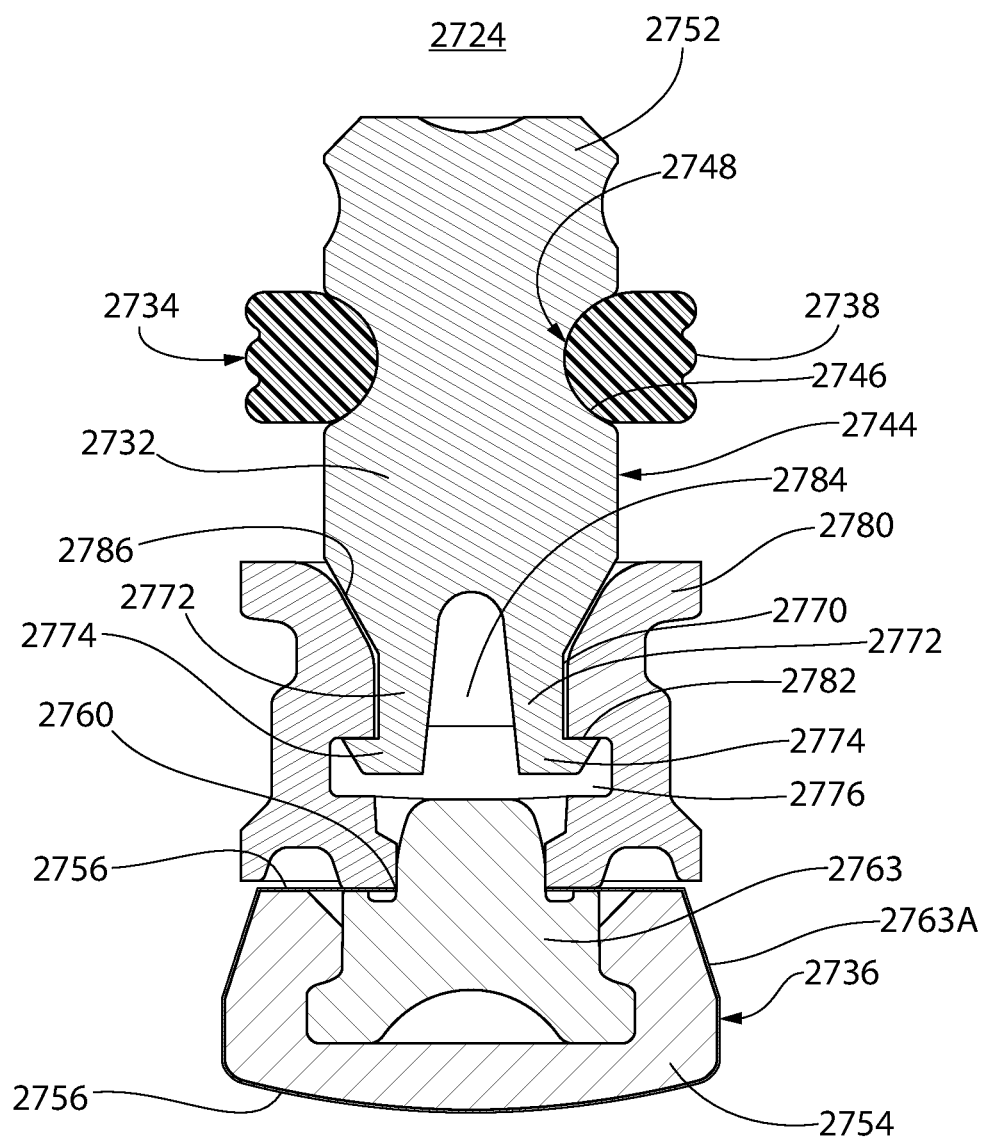
FIG. 25 is an axial sectional view of yet another embodiment of the convertible plunger, in accordance with the present invention, comprising a connector, which at a distal end thereof, is secured to the liquid sealing section and at a proximal end thereof, is secured to the central core or ring carrier.
Figure 26A:
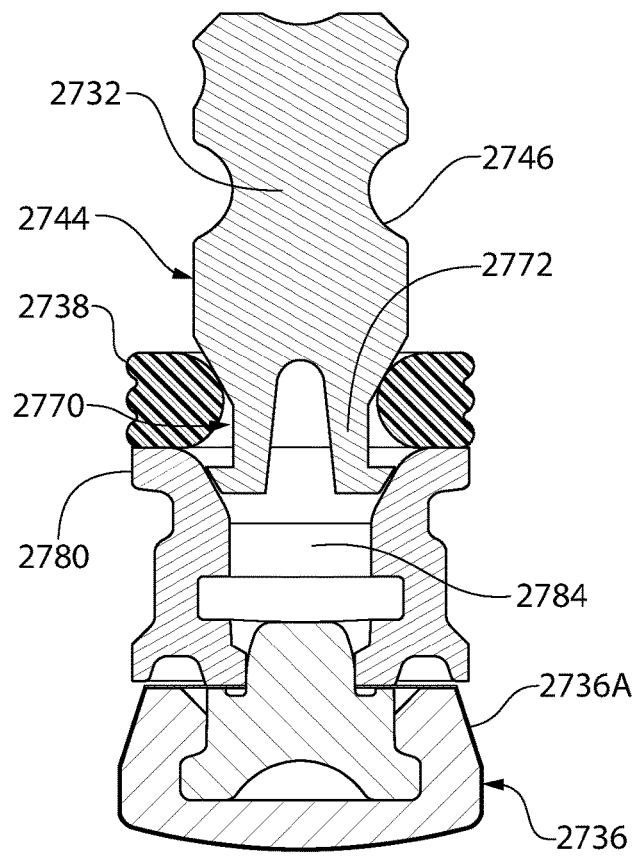
FIGS. 26A and 26B are schematic drawings illustrating the manner in which the convertible ring of FIG. 25 may be assembled.
Figure 26B:
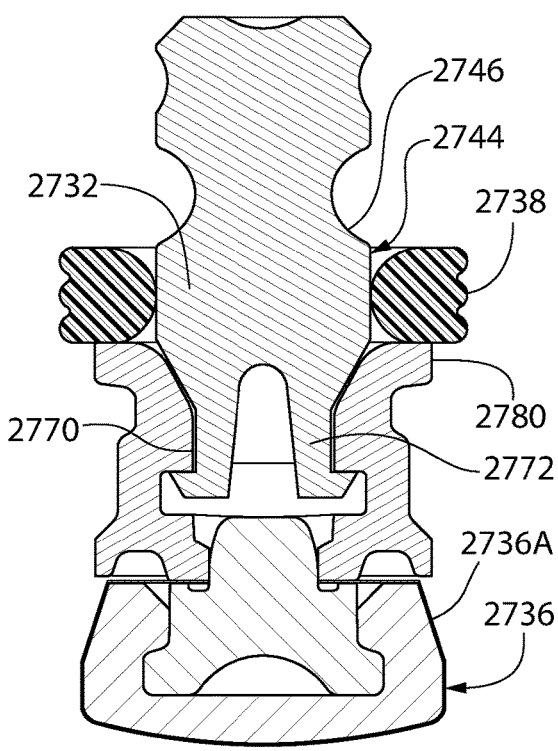
Figures 27A, 27B, 27C:
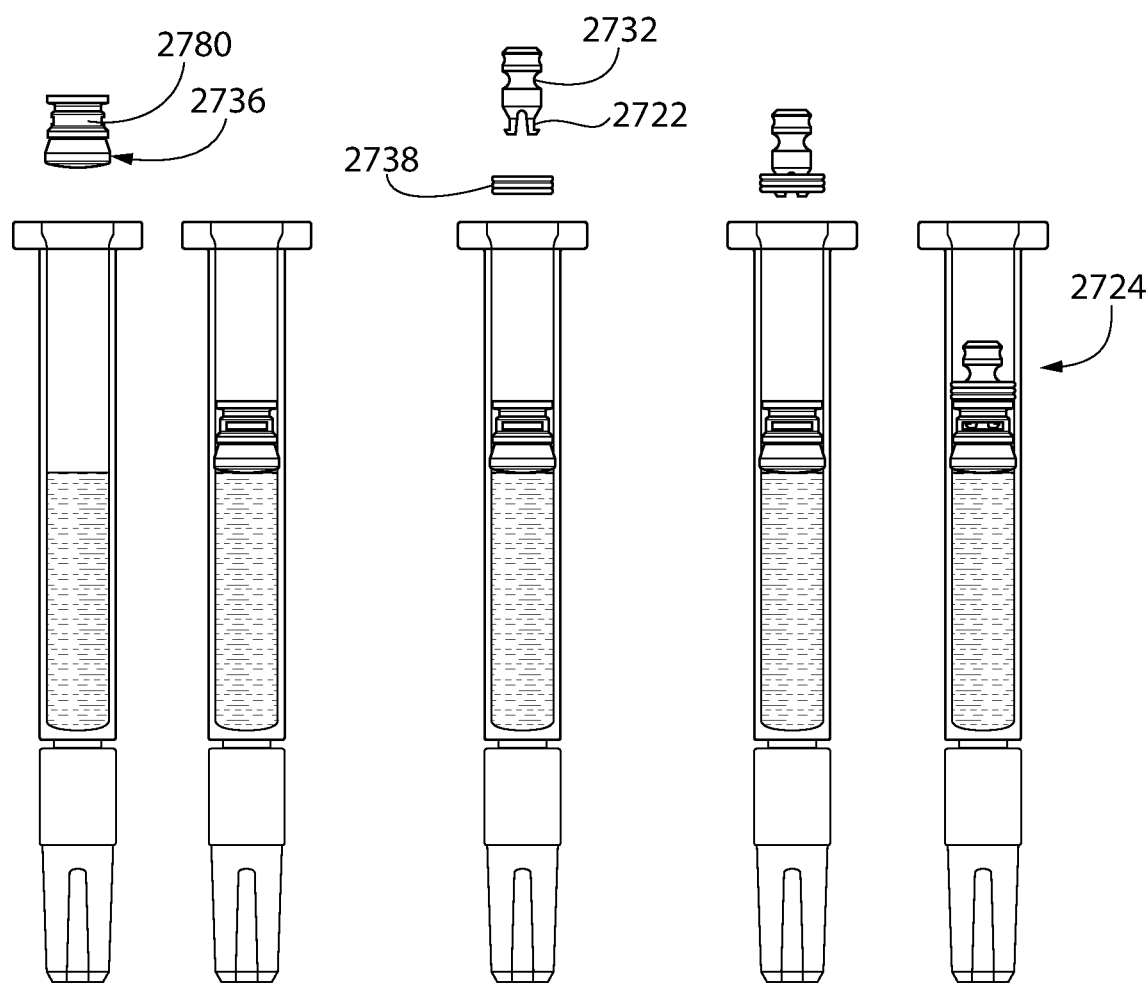
FIGS. 27A-27C are schematic drawings illustrating the manner in which the convertible plunger components of FIG. 25 may be loaded into and assembled within a syringe barrel.

Yet another alternative embodiment of convertible plunger was designed, manufactured, and evaluated to show the robust capabilities of plungers in accordance with the present invention as well as modifications that may be made for manufacturability, material selection, and ancillary functionality, as shown in FIGS. 25-27C. The plunger 2724 is, to some extent, structurally and functionally similar to the plunger 724 of FIGS. 21-23C, although there are important differences to the construction and assembly of the plunger 2724. For the sake of brevity, similar features as between the embodiments (e.g., material and configuration of the storage ring, the manner in which the plunger is secured to a plunger rod, the basic function of the plunger, etc.) will not be discussed in great depth here. However, differences may be noted. The convertible plunger according to this embodiment comprises a ring carrier in the form of a rigid central core 2732, which would be coaxial with the central axis of a syringe barrel when assembled into a syringe (as shown in FIGS. 27A-27C). As shown in FIG. 26A, the storage sealing section 2734, in the form of a storage ring 2738, is mounted on a portion of the central core 2732. The central core 2732 is an elongated rigid member comprising, from the proximal end thereof, a flange 2752 (which may be secured to a plunger rod, e.g., via threaded engagement or snap fit) which is adjacent to an annular dispensing platform 2748. Distal to the dispensing platform 2748 is an annular steep transition region 2746 which leads to the annular storage platform 2744. Accordingly, the storage platform is also considered the second position for the storage ring 2738, since the storage ring 2738 is initially in a first position about the annular insertion platform 2770 (see FIG. 26A) and caused to rest at the second position at the storage platform 2744 during assembly (see FIG. 26B). As operation of the syringe is started and the initiation or breakout force $F_i$ is overcome, displacement of storage ring 2738 from storage platform 2744 to dispensing platform 2748 is achieved with the force shown in position (2) of FIG. 29. The maintenance force $F_m$ is shown in position (3) of FIG. 29 which continues until a 30 mm travel distance in the syringe barrel is completed.

As detailed with reference to FIGS. 25 and 26B, the central core 2732 is mounted to the proximal end of a connector body 2780. The connector body 2780 is a preferably rigid (e.g., polymeric) and generally cylindrical member, the proximal end of which receives and connects to the resilient prongs 2772 of the central core 2732. The liquid sealing section 2736 is mounted to the distal end of the connector body 2780 in essentially the same way as in the previous embodiments. The description above with respect to the liquid sealing section 736 will suffice for description of the same vis-à-vis the plunger 2724 of FIGS. 25-27C.

It is noted that there are certain key distinctions between the embodiment of the present invention shown in FIGS. 25-27C and the embodiment shown in FIGS. 21-23C. A first distinction is that the embodiment in FIGS. 25-27C utilizes a different liquid sealing section 2736 preferably made of a thermoset rubber (e.g., butyl rubber) instead of a thermoplastic elastomer, as described above with reference to earlier embodiments. This material selection is believed to restrict the thermoset head 2754 from conforming to the syringe wall, thereby reducing, but maintaining surface area contact and improving overall performance consistency over time. The thermoset head 2754 features a more defined sealing section 2736, particularly in the sealing surface that would contact the fluid (e.g., a more consistent wetted area) which is believed to yield a more consistent maintenance force (as described below with reference to FIG. 29). The thermoset head 2754 also permits the manufacture of a steeper relief angle 2736A (e.g., chamfer) on head 2754, without having a manufacturing or molding parting line in the liquid sealing section 2736. This reduces the overall surface area of the head 2754 which is believed to reduce the magnitude of applied forces. Additionally, the thermoset head 2754 not being bonded (e.g., via ultrasonic weld) to stem 2763 is believed to provide manufacturing and operational benefits. For example, the wall thickness of the thermoset head 2754 (between the inner-core and syringe wall) can be reduced without detrimentally affecting the functional parameters, resulting in improved product design and less manufacturing material while maintaining or improving functional performance.

In at least one embodiment, the convertible plunger does not have an elastomeric component in direct material contact with the product-containing space. Even though the plunger head may be made from a thermoset rubber or TPE, the convertible plunger may be configured such that these materials do not have direct contact with product in a prefilled syringe. These materials have the tendency to leach into the stored product. One way to address this is through application of a film to the plunger head, as discussed herein. Alternatively, the elastomeric component, such as a thermoset rubber (e.g., butyl rubber), may be formulated to reduce or eliminate such leaching or material compatibility concerns.

As in the earlier embodiments, the liquid sealing section 2736 optionally comprises a head 2754 having a film 2756 wrapped thereon. Notably, the film 2756 is wrapped entirely around the head 2754 and continues along an underside of the head 2754, wherein the film 2756 is sandwiched between the head 2754 and the connector body 2780. The head 2754 comprises a stem 2763 that is assembled and secured into a central mating recess 2760 of the connector body 2780, e.g., by ultrasonic welding, an adhesive, a press-fit, a snap-fit or through threaded engagement. Connector body 2780 is substantially similar to connector body 780 although, notably, dimensional changes are permitted in connector body 2780 because stem 2763 does not require the longer dimensional configuration of stem 763. This unique engagement between stem 2763 and connector body 2780, and between head 2754 and stem 2763, greatly simplifies the manufacturability of the components, and the resulting dimensions of the components, while preserving or improving the operational functionality of the convertible plunger 2724.

The connector body 2780 comprises an axial channel 2784 leading to a wider opening 2776 that optionally bores entirely through a center portion of the connector body 2780, in a direction perpendicular to the central axis of the axial channel 2784. This configuration simplifies injection molding of the connector body 2780. The opening 2776 comprises a ridge section 2782 adjacent to where the axial channel 2784 meets the opening 2776. The prongs 2772, at their distal ends, comprise radially outward projecting abutments 2774. The abutments 2774 are retained underneath the ridge section 2782 to secure the central core 2732 to the connector body 2780.

To assemble the central core 2732 to the connector body 2780, the two components should be aligned and axially centered. The prongs 2772 of the central core 2732 are then inserted into the axial channel 2784 of the connector body 2780. The axial channel 2784 is configured to facilitate the insertion of the prongs 2772, e.g., with an annular chamfer 2786 at the proximal end of the axial channel 2784. When the prongs 2772 contact the chamfer 2786, the prongs 2772 are urged to resiliently flex or compress radially inward so that the prongs 2772 and abutments 2774 fit entirely within the axial channel 2784 as the prongs 2772 are moved distally into the axial channel 2784. Once the abutments 2774 fully reach the wider opening 2776, the prongs 2772 are released from their compressed state and the abutments 2774 are retained underneath the ridge section 2782, preventing the central core 2732 from being separated from the connector body 2780. In short, the prongs 2772 secure the central core 2732 to the connector body 2780 in a snap-fit configuration. This provides advantages during assembly of the plunger 2724 into a syringe barrel.

FIGS. 26A and 26B are schematic drawings illustrating the manner in which the storage ring 2738 via the central core 2732 are assembled onto the connector body 2780 and liquid sealing section 2736 subassembly or article, thus forming a completed convertible plunger 2724. FIG. 26A shows the components just prior to fully assembling them to form the plunger 2724. As shown, the distal end of the central core 2732 is protruding slightly into the axial channel 2784 of the connector body 2780 and is thus not yet secured thereto. Notably, in this position, the storage ring 2738 is disposed on the annular insertion platform 2770 of the central core 2732 or ring carrier. The annular insertion platform 2770 has a narrower outer diameter than the annular storage platform 2744. As such, the outer diameter of the storage ring 2738 is correspondingly less than the ring's 2738 outer diameter when disposed on the storage platform 2744, as shown in FIG. 26B. The comparatively small outer diameter of the storage ring 2738, when disposed about the insertion platform 2770, is configured to facilitate insertion of the ring 2738 into a syringe barrel in such a way that the ring 2738 does not contact the barrel wall or has only minimal contact with it. When on the insertion platform 2770, the sealing ring 2738 is in a "load position" wherein the ring 2738 slides easily into the proximal end of the syringe barrel. As the prongs 2772 are urged downward into the axial channel 2784 of the connector body 2780 to ultimately secure the central core 2732 thereto (as shown in FIG. 26B), the storage ring 2738 transitions from load position on the insertion platform 2770 to engagement position, wherein the ring is disposed about the storage platform 2744. Optionally, as shown in FIG. 26B, the entire ring 2738, when the plunger is in storage mode, is disposed about the storage platform 2744. In other words, no part of the ring 2738 contacts the dispensing platform when in storage mode. This helps facilitate stability of the storage ring 2738. Likewise, as shown in FIG. 25, the entire ring 2738 is optionally disposed about the dispensing platform 2748 when the plunger 2724 is in dispensing mode, which facilitates stability during dispensing. Of particular note, the alignment of ring 2738 and the dispensing platform 2748 in this embodiment is believed to enable better transition from the annular storage platform 2744, through the transition region 2746, and into the dispensing platform 2748. Additionally, the contoured dispensing platform 2748 catches the ring 2738 and holds it in place axially and radially after disengagement from the storage platform 2744 during operation. Optionally, the dispensing platform 2748 and transition region 2746 together provide a uniform annular inner radius about the perimeter of the central core 2732. This configuration improves the maintenance force parameters (as described with reference to FIG. 29) as it more uniformly transitions the ring 2738 from the storage platform 2744 and more evenly retains the ring 2738 within the dispensing platform 2748. Optionally, a lubrication layer, such as a solid phase lubrication layer, may be applied to one or both of the contact surfaces between the storage platform 2744 of the central core 2732 and the inner diameter of the ring 2738 to facilitate the transition of the ring 2738 from the storage platform 2744 to the dispensing platform 2748. For example, a solid phase lubrication layer comprising a PTFE, or a crosslinked perfluoropolyether oil, or a polyfluoroalkyl ether followed by atmospheric plasma may be applied to such surfaces. In a preferred embodiment, such a solid phase lubrication layer is applied only to the central core 2732 to facilitate the transition of the ring 2738 from the storage platform 2744 to the dispensing platform 2748.

Notably, with the aforementioned process, the ring 2738 is not separately urged or pushed with a device to set the ring 2738 into engagement mode. Rather, the ring 2738 is inserted into the syringe barrel with little or no barrel sidewall resistance by placing the ring in load position on the central core 2732 before mounting the central core 2732 to the connector body 2780. The schematic drawings of FIGS. 27A-27C more fully illustrate the manner in which the components of the convertible plunger 2724 may be loaded into a prefilled syringe and assembled. As shown in FIG. 23A, the liquid sealing section 736 and connector body 780 subassembly may be loaded into the plunger via traditional methods to load plungers. For brevity, reference is made to the discussion above with regards to FIGS. 23A-23C for the loading of the convertible plunger into a syringe.

Figure 28:
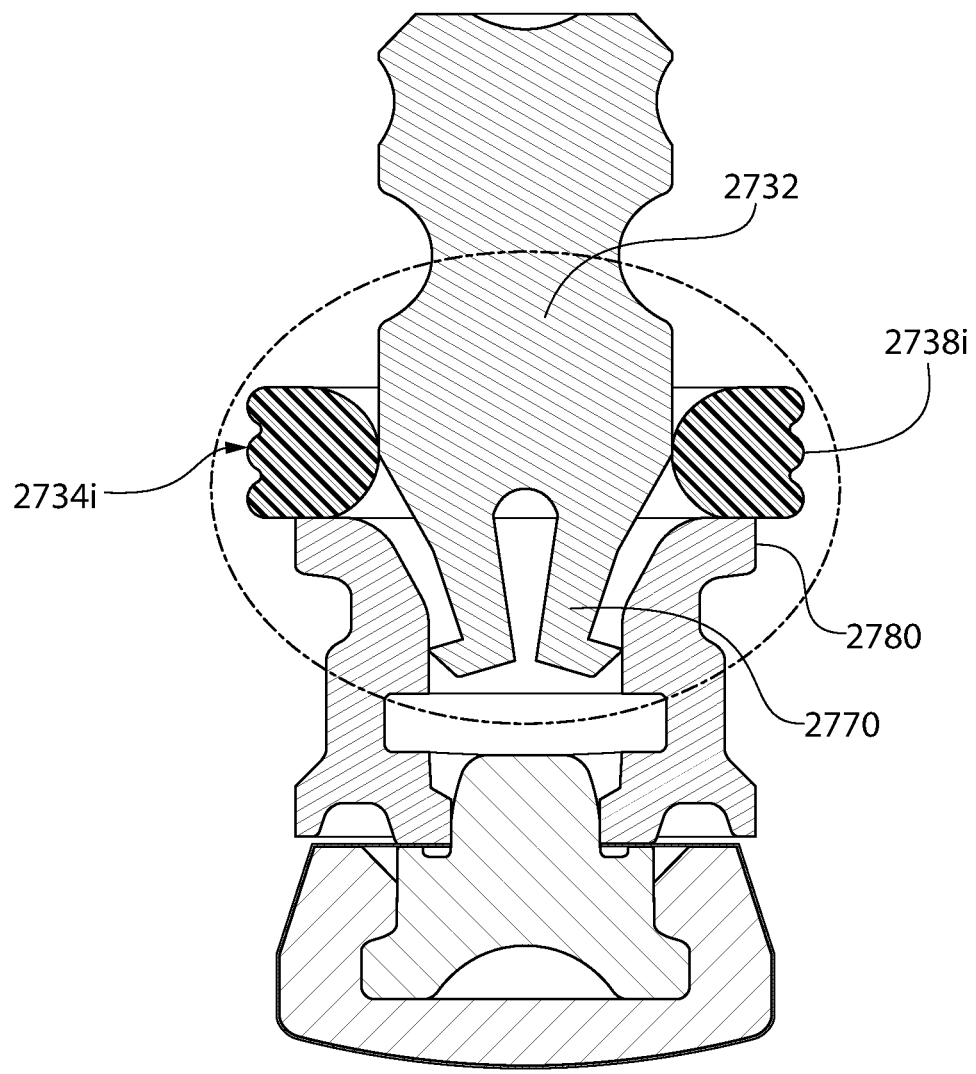
FIG. 28 is an axial sectional view of a convertible plunger identical to the plunger of FIG. 25.
Figure 28A:
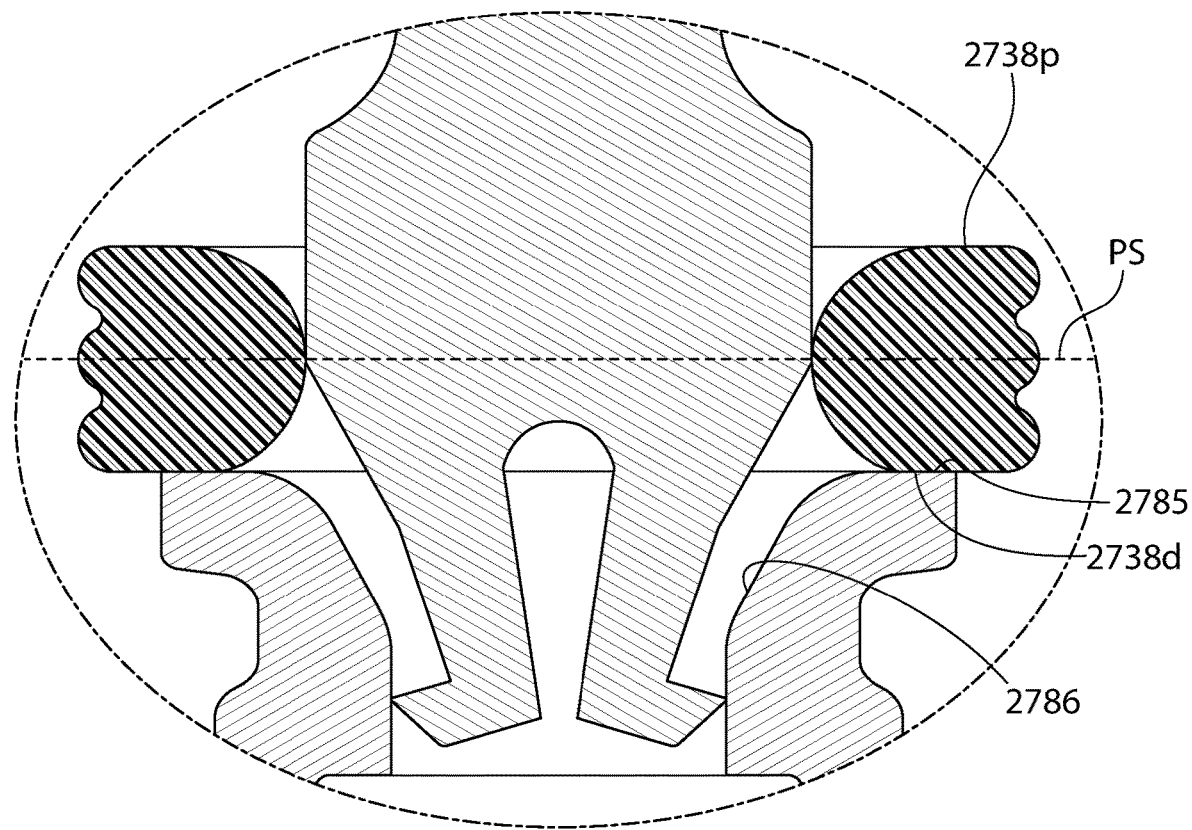
FIG. 28A is an enlarged partial view of the plunger of FIG. 28.

FIG. 28 is an axial sectional view of an convertible plunger identical to the plunger of FIG. 25. FIG. 28A is an enlarged partial view of the plunger of FIG. 28. The configuration shown in the embodiments of FIGS. 25-27C, as highlighted in FIGS. 28 and 28A, also feature a ring 2738 that has a "3-1 lobe" configuration, with 3 lobes or ribs on the outer diameter of the ring 2738 and one lobe or rib on the inner diameter. The one lobe or rib on the inner diameter, working in conjunction with the other features described herein, has been found to yield low disengagement forces which contribute to low initiation forces (as discussed further herein with reference to FIG. 29). It is preferred that the geometry of the inner lobe or rib on the inner diameter of the ring 2738 match complementary geometry of the uniform annular inner radius provided by the transition region 2746 and dispensing platform 2748, when the ring 2738 is disposed about the dispensing platform 2748. Optionally, this configuration facilitates the smooth and uniform transition of the ring 2738 from the storage platform 2744 to the dispensing platform 2748. Further, this configuration provides a deep dispensing platform 2748 for retaining the ring 2738, wherein the dispensing platform 2748 and inner diameter or surface of the ring 2738 have complementary mating geometry. In this way, the ring 2738 is securely retained about the dispensing platform such that shifting of the ring 2738 is reduced or eliminated. As a consequence, it is contemplated that the ring 2738, once secured about the dispensing platform 2738 during a dispensing operation in a syringe, will have substantially no contact or optionally no contact at all with the inner wall of a syringe barrel. While not being limited to this theory, it is believed that this configuration thus contributes to a very low, smooth/consistent plunger force and desirable force profile, e.g., as that shown in FIG. 29.

Figure 29:
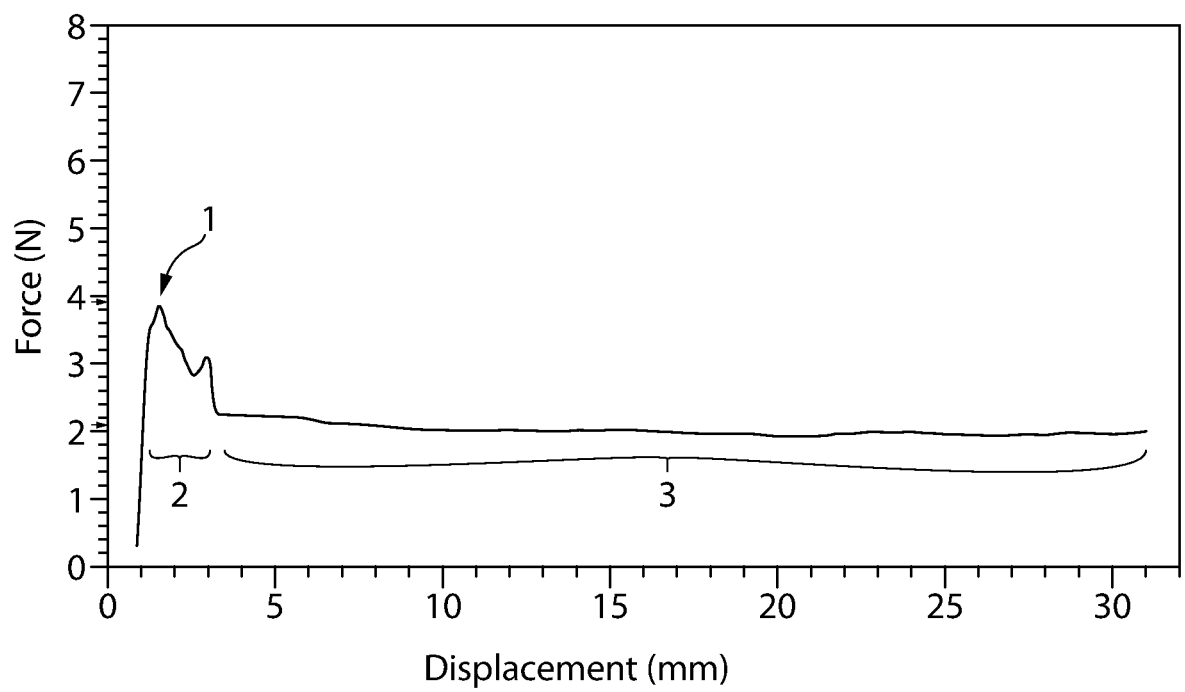
FIG. 29 is a chart of plunger force for an exemplary convertible plunger as shown in FIGS. 25-28A.

The embodiments of the present invention shown in FIGS. 25-28A demonstrated how such convertible plungers similarly achieved extraordinarily low breakout force $F_i$ and maintenance force $F_m$, as shown in the plunger force chart of FIG. 29. Again, these forces were achieved without the presence of flowable lubricant between the syringe barrel and barrel-contacting surfaces of the plunger. Even with this flowable lubricant-free solution, the plungers of the present invention continue to provide robust CCI and gas-tight sealing in order to protect the sterility and quality of contents within the syringe. FIG. 29 illustrates the plunger force profile along a 30 mm travel distance in the syringe barrel. The specimen was tested at 180 mm/min with 1 ml of water for injection (WFI) in a 1 ml Long 27G staked needle syringe, in accordance with at least one embodiment of the present invention. Position (1) shows the measure of initiation or breakout force F. The range covered by position (2) is believed to be the force associated with the displacement of storage ring 2738 from storage platform 2744 to dispensing platform 2748. The storage platform is also considered the second position for the storage ring 2738, since the storage ring 2738 is initially in a first position about the annular insertion platform 2770 (see FIG. 26A) and caused to rest at the second position at the storage platform 2744 during assembly (see FIG. 26B). As operation of the syringe is started and the initiation or breakout force $F_i$ is overcome, displacement of storage ring 2738 from storage platform 2744 to dispensing platform 2748 is achieved with the force shown in position (2) of FIG. 29. The maintenance force $F_m$ is shown in position (3) of FIG. 29 which continues until a 30 mm travel distance in the syringe barrel is completed. As the chart in FIG. 29 shows, both breakout force $F_i$ and maintenance force $F_m$ were very low, ranging between 2N-4N (below 5N). In practical terms, such a difference between $F_i$ and $F_m$ is virtually unnoticeable to a syringe handler or a patient receiving an injection therefrom. The evaluation of this embodiment of the present invention again showed a very low force profile (below 5N) between initiation and glide over the length of the barrel. Such low forces were achieved due to the uniqueness of the embodiments of the present invention and were achieved without flowable lubricant between the plunger and syringe wall.

Recitation of Exemplary Embodiments

The following exemplary embodiments further describe optional aspects of the invention and are part of this Specification. These exemplary embodiments are set forth in a format substantially akin to claims (each with numerical designations followed by the letter A), although they are not technically claims of the present application. The following exemplary embodiments refer to each other in dependent relationships as "embodiments" instead of "claims."

1A. A convertible plunger comprising:
 a. an internal portion and a generally cylindrical exterior surface that surrounds at least part of the internal portion;
 b. the generally cylindrical exterior surface comprising a compressible and resilient storage sealing section that is maintained in an expanded state by outward radial pressure provided by the internal portion;
 c. the internal portion being comparatively more rigid than the storage sealing section;
 d. the expanded state being reducible to a constricted state by an operation that is applied to the internal portion of the plunger to reduce or eliminate the outward radial pressure;
 e. the storage sealing section in the constricted state:
  i. having a reduced maximum diameter or cross-sectional width than the storage sealing section in the expanded state; and/or
  ii. being less resistant to inward radial compression compared to the storage sealing section in the expanded state;
 f. wherein the storage sealing section is configured to be set in the expanded state through application of a setting force onto the convertible plunger in a distal direction, optionally when the convertible plunger is disposed in a medical barrel;
 g. the operation being application of an actuation force onto the convertible plunger in the distal direction, optionally when the convertible plunger is disposed in a medical barrel.
 h. the convertible plunger further including a liquid sealing section on a distal end of the convertible plunger, the liquid sealing section having a generally cylindrical exterior surface configured to provide a seal against an inner wall of a medical barrel when the convertible plunger is disposed therein, the liquid sealing section having a film or a cap covering a product-facing surface and sidewall of the liquid sealing section.

2A. A pre-filled syringe comprising:
 a. a medical barrel having an inner wall and an injectable drug product, optionally a liquid composition, disposed in a product containing area of the medical barrel, the medical barrel having a distal dispensing end for dispensing the injectable drug product and an open proximal end configured for receipt of a convertible plunger; and b. a convertible plunger according to embodiment 1A or 95A disposed within the medical barrel.

3A. A pre-filled syringe comprising:

a. a medical barrel having an inner wall and an injectable drug product, optionally a liquid composition, disposed in a product containing area of the medical barrel, the medical barrel having a distal dispensing end for dispensing the injectable drug product and an open proximal end configured for receipt of a convertible plunger;

b. a convertible plunger disposed within the medical barrel proximal to the injectable drug product, the convertible plunger comprising:

i. an internal portion and a generally cylindrical exterior surface that surrounds at least part of the internal portion;

ii. the generally cylindrical exterior surface comprising a compressible and resilient storage sealing section that is maintained in an expanded state by outward radial pressure provided by the internal portion, thereby rendering the convertible plunger in storage mode;

iii. the internal portion being comparatively more rigid than the storage sealing section;

iv. the expanded state being reducible to a constricted state by an operation that is applied to the internal portion of the plunger to reduce or eliminate the outward radial pressure to transition the convertible plunger from the storage mode to a dispensing mode;

v. the storage sealing section in the constricted state:
1. having a reduced maximum diameter or cross-sectional width than the storage sealing section in the expanded state; and/or
2. being less resistant to inward radial compression compared to the storage sealing section in the expanded state;

c. wherein the convertible plunger provides a break loose force and glide force below 15 N, optionally below 10 N, optionally below 9 N, optionally below 8 N, optionally below 7 N, optionally below 6 N, optionally below 4 N, optionally between 2 N and 5.5 N, optionally between 2 N and 4 N, entirely without the presence of a flowable lubricant between the inner wall of the medical barrel and the convertible plunger's barrel-contacting surfaces.

4A. A convertible plunger comprising:

a. an internal portion and a generally cylindrical exterior surface that surrounds at least part of the internal portion;

b. the generally cylindrical exterior surface comprising a compressible and resilient storage sealing section that is maintained in an expanded state by outward radial pressure provided by the internal portion;

c. the internal portion being comparatively more rigid than the storage sealing section;

d. the expanded state being reducible to a constricted state by an operation that is applied to the internal portion of the plunger to reduce or eliminate the outward radial pressure;

e. the storage sealing section in the constricted state:

i. having a reduced maximum diameter or cross-sectional width than the storage sealing section in the expanded state; and/or ii. being less resistant to inward radial compression compared to the storage sealing section in the expanded state;

f. a plunger head provided at a distal end of the convertible plunger, the plunger head comprising a liquid sealing section configured to provide a liquid tight seal and optionally a CCI seal against an inner wall of a medical barrel, wherein the plunger head comprises a first component;

g. the storage sealing section being mounted to and axially movable about a second component or integral with the second component;

h. wherein the first component and second component are separate components that are assembled to form the convertible plunger.

5A. A pre-filled syringe comprising:

a. a medical barrel having an inner wall and an injectable drug product, optionally a liquid composition, disposed in a product containing area of the medical barrel, the medical barrel having a distal dispensing end for dispensing the injectable drug product and an open proximal end configured for receipt of a convertible plunger; and b. a convertible plunger according to embodiment 4A disposed within the medical barrel.

6A. A pre-filled syringe comprising:

a. a medical barrel having an inner wall and an injectable drug product, optionally a liquid composition, disposed in a product containing area of the medical barrel, the injectable drug product comprising a polypeptide composition or protein composition, the medical barrel having a distal dispensing end for dispensing the injectable drug product and an open proximal end configured for receipt of a convertible plunger;

b. a convertible plunger disposed within the medical barrel proximal to the injectable drug product, the convertible plunger comprising:

i. an internal portion and a generally cylindrical exterior surface that surrounds at least part of the internal portion;

ii. the generally cylindrical exterior surface comprising a compressible and resilient storage sealing section that is maintained in an expanded state by outward radial pressure provided by the internal portion, thereby rendering the convertible plunger in storage mode;

iii. the internal portion being comparatively more rigid than the storage sealing section;

iv. the expanded state being reducible to a constricted state by an operation that is applied to the internal portion of the plunger to reduce or eliminate the outward radial pressure to transition the convertible plunger from the storage mode to a dispensing mode;

v. the storage sealing section in the constricted state:
1. having a reduced maximum diameter or cross-sectional width than the storage sealing section in the expanded state; and/or
2. being less resistant to inward radial compression compared to the s storage sealing section in the expanded state;

c. the convertible plunger providing a break loose force and glide force below 15 N, optionally below 10 N, optionally below 9 N, optionally below 8 N, optionally below 7 N, optionally below 6 N, optionally below 4 N, optionally between 2 N and 5.5 N, optionally between 2 N and 4 N, entirely without the presence of a flowable lubricant between the inner wall of the medical barrel and the convertible plunger's barrel-contacting surfaces;
d. wherein flowable lubricant-generated particles are absent from the drug product.
7A. A method for assembling a convertible plunger into a medical barrel to form a syringe, the method comprising the steps of:
a. providing a medical barrel having an inner wall and a product containing area, the product containing area being configured for containing an injectable drug product, optionally a liquid composition, the medical barrel having a distal dispensing end for dispensing an injectable drug product and an open proximal end configured for receipt of a convertible plunger;
b. inserting a convertible plunger through the open proximal end of the medical barrel and disposing the convertible plunger within the medical barrel proximal to the product containing area, the convertible plunger comprising:
  i. an internal portion and a generally cylindrical exterior surface that surrounds at least part of the internal portion;
  ii. the generally cylindrical exterior surface comprising a compressible and resilient storage sealing section that is maintained in an expanded state by outward radial pressure provided by the internal portion, thereby rendering the convertible plunger in storage mode;
  iii. the internal portion being comparatively more rigid than the storage sealing section;
  iv. the expanded state being reducible to a constricted state by an operation that is applied to the internal portion of the plunger to reduce or eliminate the outward radial pressure to transition the convertible plunger from the storage mode to a dispensing mode;
  v. the storage sealing section in the constricted state:
    1. having a reduced maximum diameter or cross-sectional width than the storage sealing section in the expanded state; and/or
    2. being less resistant to inward radial compression compared to the storage sealing section in the expanded state; and
c. applying a setting force onto the convertible plunger in a distal direction in order to set the storage sealing section in the expanded state, thereby placing the convertible plunger in the storage mode.
8A. The method of embodiment 7A, wherein the convertible plunger in the storage mode is configured to transition to the dispensing mode upon providing an actuation force onto the convertible plunger in a distal direction.
9A. The method of embodiments 7A or 8A, wherein the syringe is pre-filled in a manufacturing filling process with a drug product in the product containing area.
10A. The syringe of any of embodiments 2A, 3A, 5A and 6A, or the method of any of embodiments 7A-9A, wherein flowable lubricant is absent from the product containing area.
11A. The syringe of any of embodiments 2A, 3A, 5A, 6A and 10A or the method of any of embodiments 7A-10A, wherein the barrel is made from an injection moldable thermoplastic resin, optionally COP or COC.
12A. The syringe of any of embodiments 2A, 3A, 5A, 6A, 10A and 11A or the method of any of embodiments 7-11, wherein the barrel has an organo-siloxane coating or layer on the interior wall of the barrel, optionally wherein the organosiloxane coating or layer is a pH protective coating, optionally as a top layer of a tri-layer coating set.
13A. The syringe of any of embodiments 2A, 3A, 5A, 6A and 10A-12A or the method of any of embodiments 7A-12A, wherein the storage sealing section in the expanded state forms a liquid-tight, CCI and gas-tight interface with the interior wall of the barrel, optionally wherein the gas-tight interface is substantially impermeable to oxygen, nitrogen, water vapor and/or ethylene oxide.
14A. The syringe of any of embodiments 2A, 3A, 5A, 6A and 10A-13A or the method of any of embodiments 7A-13A, wherein the storage sealing section in the expanded state forms a CCI and gas-tight seal over a product shelf-life of 6 months, one year, optionally 18 months, optionally 24 months, optionally three years.
15A. The syringe of any of embodiments 2A, 5A, 6A and 10A-14A or the method of any of embodiments 7A-14A, wherein the plunger provides a break loose force and glide force below 15 N, optionally below 10 N, optionally below 9 N, optionally below 8 N, optionally below 7 N, optionally below 6 N, optionally below 4 N, optionally between 2 N and 5.5 N, optionally between 2 N and 4 N, entirely without the presence of a flowable lubricant between the barrel and the plunger's barrel-contacting surfaces.
16A. The syringe of any of embodiments 2A, 3A, 5A, 6A and 10A-15A or the method of any of embodiments 7A-15A, wherein the plunger provides a differential between break loose force and glide force of optionally below 2 N, optionally below 1.5 N, optionally below 1.0 N, optionally below 0.5 N, optionally below 0.4 N, optionally below 0.25 N, entirely without the presence of a flowable lubricant between the barrel and the plunger's barrel-contacting surfaces.
17A. The syringe of any of embodiments 2A, 3A, 5A, 6A and 10A-16A or the method of any of embodiments 7A-16A, wherein the plunger provides a differential between break loose force and glide force of optionally below 20%, optionally below 15%, optionally below 12%, optionally below 10%, optionally below 8%, optionally between 2.5% and 6% entirely without the presence of a flowable lubricant between the barrel and the plunger's barrel-contacting surfaces.
18A. The syringe of any of embodiments 2A, 3A, 5A, 6A and 10A-17A or the method of any of embodiments 7A-17A, wherein the convertible plunger is secured to a plunger rod, forming a plunger assembly, wherein the plunger rod is configured to be pressed in a distal direction to actuate the plunger and dispense the drug product.
19A. The syringe of any of embodiments 2A, 3A, 5A, 6A and 10A-18A or the method of any of embodiments 7A-18A, wherein the storage sealing section includes at least two annular ribs separated by an annular valley therebetween.
20A. The syringe of any of embodiments 2A, 3A, 5A and 10A-17A or the method of any of embodiments 7A-17A, wherein the drug product is an injectable liquid selected from the group consisting of: a small molecule pharmaceutical drug product, a biologic, a vaccine, a peptide-based drug, a protein-based drug, sterile water or saline solution for injection and a diagnostic medium.

21A. The syringe of any of embodiments 2A, 3A, 5A, 6A, 10A and 12A-20A or the method of any of embodiments 7A-10A and 12A-20A, wherein the barrel is made from glass.

22A. The syringe of any of embodiments 2A, 3A, 5A, 6A and 10A-21A or the method of any of embodiments 7A-21A, wherein the convertible plunger further comprises a liquid sealing section that is located distal to the storage sealing section, the liquid sealing section comprising a film coating having a lower coefficient of friction than a substrate to which the film coating is applied, the film coating optionally being a fluoropolymer film, the liquid sealing section preferably providing a liquid tight seal against the inner wall of the barrel.

23A. The syringe of any of embodiments 2A, 3A, 5A, 6A and 10A-22A or the method of any of embodiments 7A-22A, wherein the syringe is a component of an auto injector.

24A. The syringe of any of embodiments 2A, 3A, 5A, 6A and 10A-23A or the method of any of embodiments 7A-23A, wherein the syringe is a 0.5 mL syringe.

25A. The syringe of any of embodiments 2A, 3A, 5A, 6A and 10A-24A or the method of any of embodiments 7A-24A, wherein the barrel has an inner diameter of from 2.5 mm to 4.6 mm.

26A. The syringe of any of embodiments 2A, 3A, 5A, 6A and 10A-25A or the method of any of embodiments 7A-25A, wherein the storage sealing section is on an outer storage ring disposed about the convertible plunger, the convertible plunger being configured to axially translate distally relative to the storage ring when transitioning from storage mode to dispensing mode.

27A. The syringe of any of embodiments 2A, 3A, 5A, 6A and 10A-26A or the method of any of embodiments 7A-26A:
a. the injectable drug product comprising a polypeptide composition or protein composition that is susceptible to one or more of the following negative effects from infraction with particles generated from a flowable lubricant:
i. denaturing of proteins in the composition;
ii. agglomeration of proteins in the composition;
iii. degradation of proteins in the composition;
iv. triggering an undesired immune response in a patient; and
v. degrading efficacy of the drug product;
b. wherein flowable lubricant-generated particles are absent from the drug product such that the drug product is not subject to the one or more of the negative effects from flowable lubricant-generated particles 28A. A method for using the syringe of any of embodiments 2A, 3A, 5A, 6A and 10A-27A or a syringe made according to the method of any of embodiments 7A-26A for ophthalmic applications, wherein the syringe contains 5-50 microliters, optionally 10-30 microliters, optionally 10-20 microliters of ophthalmic drug in the product-containing space and wherein the barrel has an inner diameter of from 2.5 mm to 4.6 mm, the method comprising:
a. inserting a needle into a patient's eye tissue wherein the needle provides fluid communication from the product-containing area through the dispensing end of the barrel;
b. actuating the convertible plunger to transition from storage mode to dispensing mode, wherein step (b) precedes step (a) or step (a) precedes step (b); and
c. injecting the ophthalmic drug into the patient's eye tissue.

29A. A convertible plunger for disposition within a barrel of a medical container, the barrel being configured for receipt of an injectable product therein and having a central axis and an interior wall surrounding the axis, the plunger being configured to be moved within the barrel along the axis from a storage mode to a dispensing mode, the plunger comprising a ring carrier having a compressible and resilient storage ring disposed thereon which is configured to displace axially, optionally by sliding, along the ring carrier from an engagement position, wherein the storage ring is disposed about a storage platform of the ring carrier, to a release position wherein the storage ring is disposed about a dispensing platform having a narrower cross-sectional width or diameter than the storage platform, the storage platform being optionally comparatively more rigid than the storage ring, the storage ring comprising a storage sealing section configured to apply outward radial pressure on the interior wall when the storage sealing section is in the engagement position, the storage sealing section being configured in the release position to provide reduced or no outward radial pressure on the interior wall, the plunger further comprising a plunger head mounted at a distal end of the plunger, the plunger head having a liquid sealing section configured to contact and provide a seal against the interior wall, wherein the plunger head is a separate component assembled with the ring carrier to form the convertible plunger.

30A. The convertible plunger of embodiment 29A, wherein the plunger head is a separate component assembled directly with the ring carrier to form the convertible plunger 31A. A convertible plunger comprising:
a. a first subassembly comprising an optionally polymeric and optionally generally cylindrical connector body having a distal end and a proximal end, the first subassembly further comprising a plunger head, which is a separate component that is assembled to the distal end of the connector body, the plunger head having a liquid sealing section configured to contact and provide a seal against an interior wall of a medical barrel when disposed therein;
b. a second subassembly comprising an elongate ring carrier, which is optionally polymeric, having a distal end and a proximal end, the distal end of the ring carrier being secured to the proximal end of first subassembly, the proximal end of the ring carrier configured to be secured to a plunger rod, the ring carrier comprising, from its proximal end, an annular dispensing platform and an annular storage platform distal to the dispensing platform, the annular storage platform having a larger maximum diameter or cross-sectional width than the dispensing platform, the second subassembly further comprising a compressible and resilient storage ring, which is optionally elastomeric, disposed about the ring carrier and configured to displace axially thereon, optionally slide axially thereon;
c. wherein the storage platform is optionally comparatively more rigid than the storage ring.

32A. The convertible plunger of embodiment 31A, the proximal end of the connector body comprising a recess or axial channel, the ring carrier further comprising an annular insertion platform distal to the annular storage platform, the annular insertion platform having a smaller maximum diameter or cross-sectional width than the storage platform, the insertion platform being disposed in the recess or axial channel so as to fixedly secure the first subassembly to the second subassembly.

33A. The convertible plunger of any of embodiments 29A-32A, there being a fluoropolymer film wrapped about the liquid sealing section.

34A. The convertible plunger of any of embodiments 29A-33A, wherein the storage ring includes at least two annular ribs separated by an annular valley therebetween.

35A. The convertible plunger of any of embodiments 29A-34A, wherein the storage ring in an uncompressed state comprises a rib on an inside surface of the storage ring and an opposing rib on the outer surface of the storage sealing section.

36A. The convertible plunger of any of embodiments 29A-35A, the storage ring comprising an outer surface facing generally radially outward away from the ring carrier, wherein when the storage ring is in an uncompressed state, the outer surface comprises a proximal end, a distal end and a radial plane of symmetry between the proximal and distal ends, optionally equidistant from the proximal and distal ends, wherein the outer surface is symmetrical on either side of the radial plane of symmetry.

37A. A pre-filled syringe comprising:
a. a medical barrel having an inner wall and an injectable drug product, optionally a liquid composition, disposed in a product containing area of the medical barrel, the medical barrel having a distal dispensing end for dispensing the injectable drug product and an open proximal end configured for receipt of a convertible plunger;
b. a convertible plunger according to any of embodiments 28A-35A disposed within the medical barrel.

38A. The pre-filled syringe of embodiment 37A, wherein the storage sealing section, when the storage ring is disposed about the storage platform, is maintained in an expanded state by outward radial pressure provided by the storage platform to create compression between the storage sealing section and the inner wall of the barrel, thereby rendering the convertible plunger in storage mode, the expanded state being reducible to a constricted state upon transitioning the storage ring to being disposed about the dispensing platform whereupon the compression between the storage sealing section and the inner wall of the barrel is reduced or eliminated, thereby rendering the convertible plunger in dispensing mode.

39A. The pre-filled syringe of embodiment 38A, wherein the entire storage ring is disposed about the storage platform when the plunger is in storage mode.

40A. The pre-filled syringe of embodiments 38A or 39A, wherein the entire storage ring is disposed about the dispensing platform when the plunger is in dispensing mode.

41A. The pre-filled syringe of any of embodiments 38A-40A, wherein the storage sealing section is configured to be set in the expanded state through application of a setting force onto the convertible plunger in a distal direction.

42A. The pre-filled syringe of any of embodiments 38A-41A, wherein the convertible plunger in storage mode is configured to transition to dispensing mode upon providing an actuation force onto the convertible plunger in a distal direction.

43A. An assembly comprising:
a. a plunger head comprising a compressible and resilient material, optionally an elastomer or a thermoplastic elastomer, for providing a seal, optionally a liquid tight seal, when disposed in a medical barrel, the plunger comprising a distal product-facing surface, a proximal end and a sidewall therebetween configured for contacting an inner wall of a medical barrel to form the seal when disposed in the medical barrel;
b. a rigid component or rigid subassembly, optionally a ring carrier, a central core and/or a connector body, fixedly secured at a distal end of the rigid component or rigid subassembly, to the proximal end of the plunger head; and
c. a fluoropolymer film piece wrapped about the plunger head, entirely covering the product-facing surface and sidewall, the fluoropolymer film piece having an edge about its perimeter, wherein the edge is not exposed on the assembly, optionally because the edge is sandwiched between the plunger head and the rigid component or rigid subassembly.

44A. A method for making a fluoropolymer film coated liquid sealing section for a plunger, optionally as a component of a convertible plunger, the method comprising the steps of:
a. providing a plunger head comprising a compressible and resilient material, optionally an elastomer, disposed over a comparatively more rigid support, optionally a polymer support, the plunger head comprising a distal product-facing surface, a proximal end and a sidewall therebetween configured for contacting an inner wall of a medical barrel to form a seal, optionally a liquid tight seal, when disposed in a medical barrel, the plunger head optionally comprising a stem extending from the proximal end;
b. loading the plunger head in tooling;
c. providing a fluoropolymer film preform and applying a vacuum thereto to pull the film preform into preform tooling, the preform along one side being smaller in surface area than the combined surface area of product-facing surface and sidewall;
d. clamping the preform about at least a portion of its perimeter, inverting the preform optionally using a vacuum and pushing the plunger head into the inverted preform so as to stretch the preform to conform to the product-facing surface and sidewall of the plunger head;
e. pushing the plunger head and preform through a tool to gather excess film extending from the proximal end of the plunger head;
f. gripping the plunger head with a gripper to fix the plunger in place; and
g. trimming excess film from the proximal end of the plunger and optionally rotating the plunger head to break the plunger head free from trimmed excess film.

45A. The method of embodiment 44A, wherein the plunger head comprises an elastomer disposed over a polymer support, the plunger head having been made through two-shot injection molding, wherein a first shot injects the rigid support within a mold and the second shot injects the elastomer in the mold, or vice versa.

46A. The method of embodiment 45A, wherein the elastomer comprises a polyolefin based thermoplastic elastomer and the polymer support comprises a polyolefin, optionally polypropylene, cyclic olefin polymer or cyclic olefin copolymer.

47A. A method for making an assembly, the method comprising the steps of:
a. providing a plunger head comprising a compressible and resilient material, optionally an elastomer, disposed over a comparatively more rigid polymer support, the plunger head comprising a distal product-facing surface, a proximal end and a sidewall therebetween configured for contacting an inner wall of a medical barrel to form a seal, optionally a liquid tight seal, when disposed in a medical barrel;
b. optionally providing a fluoropolymer film wrapped about the plunger head, entirely covering the product-facing surface and sidewall;
c. providing a polymeric and optionally generally cylindrical connector body having a distal end and a proximal end, the proximal end of the plunger head being assembled to the distal end of the connector body and optionally secured thereto by joining, optionally by welding, the rigid support of the plunger head to the distal end of the connector body, wherein respective materials of the rigid support and connector body are configured to be compatible with each other for ultrasonic welding;
d. providing an elongate polymeric ring carrier having a distal end and a proximal end, the distal end of the ring carrier being assembled to the proximal end of the connector body, wherein the ring carrier comprises a material having lower gas permeability, optionally lower oxygen permeability, nitrogen permeability, water vapor permeability and/or ethylene oxide permeability, than the connector body.

48A. The method of embodiment 47A, further comprising the step of:
e. disposing an elastomeric storage ring about the ring carrier, the ring carrier being configured to displace axially relative to the storage ring.

49A. The method of embodiments 47A or 48A, wherein: the compressible and resilient material of the plunger head is optionally a thermoplastic elastomer; and/or the rigid support is optionally polypropylene; and/or the connector body is polypropylene; and/or the ring carrier is cyclic olefin polymer.

50A. A method for assembling a convertible plunger into a pre-filled syringe comprising the steps of:
a. providing a syringe barrel having a central axis and an interior wall surrounding the axis, the barrel comprising a dispensing end, an open top and a product containing area therebetween, the product containing area being pre-filled to a desired amount with an injectable drug product, optionally a liquid composition;
b. providing a first subassembly (or article) comprising a rigid and generally cylindrical connector body having a distal end and a proximal end, the proximal end having a recess or axial channel, the first subassembly further comprising a plunger head, which is a separate component that is assembled to the distal end of the connector body, the plunger head having a liquid sealing section configured to contact and provide a seal against the interior wall of the barrel when disposed therein;
c. providing a second subassembly (or article) comprising a rigid elongate ring carrier having a distal end and a proximal end, the distal end configured to be secured to the first subassembly, the proximal end configured to be secured to a plunger rod, the ring carrier comprising, from its proximal end, an annular dispensing platform, and an annular storage platform distal to the dispensing platform, the annular storage platform having a larger maximum diameter or cross-sectional width than the dispensing platform and an annular insertion platform distal to the annular storage platform, the annular insertion platform having a smaller maximum diameter or cross-sectional width than the storage platform, the second subassembly further comprising a compressible and resilient storage ring, which is optionally elastomeric, disposed about the ring carrier and configured to displace axially thereon, optionally slide axially thereon;
d. loading the first subassembly into the syringe barrel with the plunger head located distally in the barrel with respect to the connector body, the loading step optionally being achieved through a vent tube, vacuum or vacuum assist loading method;
e. positioning the storage ring about the insertion platform and axially aligning the second subassembly with the recess or axial channel of the connector body, the distal end of the ring carrier facing the recess or axial channel; and
f. after step (e), moving the first subassembly toward the second subassembly and/or vice versa to dispose the second subassembly into the syringe barrel, whereupon the insertion platform is inserted into the recess or axial channel while the storage ring contacts the proximal end of the connector body, wherein as the insertion platform is further inserted into the storage ring, the storage ring is pushed off the insertion platform and is disposed about the storage platform, thereby creating a compression seal between the storage ring and the interior wall of the barrel and fixedly securing the first subassembly to the second subassembly, thereby assembling the convertible plunger.

51A. The method of embodiment 50A, wherein a pressure zone is not created between the storage ring and the first subassembly.

52A. The method of embodiments 50A or 51A, wherein no flowable lubricant is applied between the convertible plunger and the interior wall of the syringe barrel.

53A. The method of any of embodiments 50A-52A, wherein while the storage ring is disposed about the insertion platform and the second subassembly is disposed within the syringe barrel, the storage ring either does not contact the interior wall of the syringe barrel or, if the storage ring does contact the interior wall, the storage ring provides less radial pressure against the interior wall than the storage ring exerts upon completion of step (f).

54A. The method of any of embodiments 50A-53A, wherein step (f) places the convertible plunger in storage mode, wherein the storage ring provides a gas-tight and CCI seal.

55A. The method of any of embodiments 50A-54A, wherein the plunger head is wrapped in a fluoropolymer film prior to assembly to the connector body, wherein the edge is not exposed on the convertible plunger, optionally because a portion of the film is sandwiched between the plunger head and the distal end of the connector body after being assembled to the connector body.

56A. The method of any of embodiments 50A-55A, wherein the plunger head comprises a rigid polymeric support with an elastomeric material disposed around the support, optionally made in a two shot injection molding process.

57A. The method of any of embodiments 50A-56A, wherein the convertible plunger in storage mode is configured to transition to a dispensing mode upon providing an actuation force onto the convertible plunger in a distal direction.
58A. The method of any of embodiments 50A-57A, wherein flowable lubricant is absent from the product containing area.
59A. The method of any of embodiments 50A-58A, wherein the barrel is made from an injection moldable thermoplastic resin, optionally COP or COC.
60A. The method of any of embodiments 50A-59A, wherein the barrel has an organo-siloxane coating or layer on the interior wall of the barrel, optionally wherein the organosiloxane coating or layer is a pH protective coating, optionally as a top layer of a tri-layer coating set.
61A. The method of any of embodiments 50A-60A, wherein the storage sealing section in the expanded state forms a liquid-tight, CCI and gas-tight interface with the interior wall of the barrel, optionally wherein the gas-tight interface is substantially impermeable to oxygen, nitrogen, water vapor and/or ethylene oxide.
62A. The method of any of embodiments 50A-61A, wherein the storage sealing section in the expanded state forms a CCI and gas-tight seal over a product shelf-life of optionally 6 months, optionally one year, optionally 18 months, optionally 24 months, optionally three years.
63A. The method of any of embodiments 50A-62A, wherein the plunger provides a break loose force and glide force below 15 N, optionally below 10 N, optionally below 9 N, optionally below 8 N, optionally below 7 N, optionally below 6 N, optionally below 4 N, optionally between 2 N and 5.5 N, optionally between 2 N and 4 N, entirely without the presence of a flowable lubricant between the barrel and the plunger's barrel-contacting surfaces.
64A. The method of any of embodiments 50A-63A, wherein the plunger provides a differential between break loose force and glide force of optionally below 2 N, optionally below 1.5 N, optionally below 1.0 N, optionally below 0.5 N, optionally below 0.4 N, optionally below 0.25 N, entirely without the presence of a flowable lubricant between the barrel and the plunger's barrel-contacting surfaces.
65A. The method of any of embodiments 50A-64A, wherein the plunger provides a differential between break loose force and glide force of optionally below 20%, optionally below 15%, optionally below 12%, optionally below 10%, optionally below 8%, optionally between 2.5% and 6% entirely without the presence of a flowable lubricant between the barrel and the plunger's barrel-contacting surfaces.
66A. The method of any of embodiments 50A-65A, wherein the convertible plunger is secured to a plunger rod, forming a plunger assembly, wherein the plunger rod is configured to be pressed in a distal direction to actuate the plunger and dispense the drug product.
67A. The method of any of embodiments 50A-66A, wherein the storage sealing section includes at least two annular ribs separated by an annular valley therebetween.
68A. The method of any of embodiments 50A-67A, wherein the syringe is a 0.5 mL syringe.
69A. The method of any of embodiments 50A-68A, wherein the barrel has an inner diameter of from 2.5 mm to 4.6 mm.
70A. The method of any of embodiments 50A-69A:
a. the injectable drug product comprising a polypeptide composition or protein composition that is susceptible to one or more of the following negative effects from interaction with particles generated from a flowable lubricant:
i. denaturing of proteins in the composition;
ii. agglomeration of proteins in the composition;
iii. degradation of proteins in the composition;
iv. triggering an undesired immune response in a patient; and
v. degrading efficacy of the drug product;
b. wherein flowable lubricant-generated particles are absent from the drug product such that the drug product is not subject to the one or more of the negative effects from flowable lubricant-generated particles.
71A. The method of any of embodiments 50A-70A, wherein compression of the storage ring disposed on the ring carrier does not compress the ring carrier.
72A. The method of any of embodiments 50A-71A, wherein the storage ring, when the plunger is in storage mode and during transition from storage mode to dispensing mode, preferentially adheres to the interior wall of the barrel, optionally wherein a lubricating means is provided between the storage ring and the ring carrier to facilitate displacing, optionally by sliding, of the storage ring axially along the ring carrier while adhering to the interior wall of the barrel during transition from storage mode to dispensing mode.
73A. A method for using a syringe made according to the method of any of embodiments 50-72, wherein the syringe contains 5-50 microliters, optionally 10-30 microliters, optionally 10-20 microliters of ophthalmic drug in the product-containing space and wherein the barrel has an inner diameter of from 2.5 mm to 4.6 mm, the method comprising:
a. inserting a needle into a patient's eye tissue wherein the needle provides fluid communication from the product-containing area through the dispensing end of the barrel;
b. actuating the convertible plunger to transition from storage mode to dispensing mode, wherein step (b) precedes step (a) or step (a) precedes step (b); and
c. injecting the ophthalmic drug into the patient's eye tissue.
74A. A convertible plunger assembly configured to be disposed within a syringe barrel and advanced in a dispensing direction to dispense the contents of the syringe barrel, the plunger assembly comprising:
a. a plunger having an axial cavity and at least two axially spaced generally annular ribs, each having an inner diameter and an outer diameter, joined by an intermediate sleeve portion of reduced outer diameter; and
b. a sliding shaft that is received in the axial cavity and displaceable along its axis, the sliding shaft including at least one annular cylindrical ring and at least one reduced diameter portion axially displaced from the ring.
75A. The convertible plunger assembly of embodiment 74A, in which the plunger sleeve has an engaged position relative to the sliding shaft, in which at least one ring biases or increases the biasing force of the inner diameters of at least two annular ribs, providing outward radial pressure that maintains the at least two adjacent ribs of the plunger in an expanded state.

76A. The convertible plunger assembly of embodiment 75A, in which the axially spaced annular ribs each have substantially the same outer diameter when the plunger sleeve is in the engaged position.

77A. The convertible plunger assembly of embodiments 75A or 76A, in which the axially spaced annular ribs each have substantially the same inner diameter when the plunger sleeve is in the engaged position.

78A. The convertible plunger assembly of any of embodiments 74A-77A, in which the plunger sleeve has a disengaged position relative to the sliding shaft, in which each ring is axially displaced with respect to the inner diameter of at least one annular rib, reducing the outward radial pressure on the at least one annular rib.

79A. The convertible plunger assembly of embodiment 78A, in which in the disengaged position each ring is axially displaced with respect to the inner diameter of each annular rib, reducing the outward radial pressure on each annular rib.

80A. The convertible plunger assembly of any of embodiments 74A-79A, in which at least one reduced diameter portion of the sliding shaft is located axially behind the ring relative to the dispensing direction.

81A. The convertible plunger assembly of any of embodiments 74A-80A, further comprising a second reduced diameter portion of the sliding shaft located axially forward of the ring relative to the dispensing direction.

82A. The convertible plunger assembly of any of embodiments 74A-81A, in which the plunger sleeve comprises at least three axially spaced annular ribs, each having an inner diameter and an outer diameter, joined by intermediate sleeve portions of reduced outer diameter.

83A. The convertible plunger assembly of embodiment 82A, in which the plunger sleeve comprises exactly three axially spaced annular ribs, each having an inner diameter and an outer diameter, joined by intermediate sleeve portions of reduced outer diameter.

84A. The convertible plunger assembly of any of embodiments 74A-83A, further comprising a plunger rod operatively connected for advancing the plunger sleeve in a syringe barrel.

85A. The convertible plunger assembly of embodiment 84A, in which the plunger rod is operatively connected for moving the sliding shaft relative to the plunger sleeve to convert the plunger sleeve from its engaged position to its disengaged position.

86A. The convertible plunger assembly of embodiment 85A, in which the plunger rod is operatively connected for advancing the sliding shaft in the dispensing direction to convert the plunger sleeve from its engaged position to its disengaged position.

87A. The convertible plunger assembly of any of embodiments 74A-86A, further comprising a dispensing seal for engaging fluid in a syringe barrel to dispense the fluid.

88A. The convertible plunger assembly of embodiment 87A, in which the dispensing seal is axially displaced from the ribs in the dispensing direction.

89A. The convertible plunger assembly of embodiments 87A or 88A, in which the plunger assembly has a dispensing end and an opposed back end, and the dispensing seal is located at the dispensing end.

90A. The convertible plunger assembly of any of embodiments 87A-89A, in which the dispensing seal comprises an elastomeric piston having a leading end for engaging a fluid in a syringe.

91A. The convertible plunger assembly of embodiment 90A, in which the dispensing seal further comprises a film covering the leading end.

92A. The convertible plunger assembly of embodiment 91A, in which the film comprises a sheet wrapped about the leading end.

93A. The convertible plunger assembly of embodiment 92A, in which the sheet comprises an edge portion tucked radially inward behind the piston.

94A. The convertible plunger assembly of embodiment 91A, in which the film comprises a coating formed on the leading end.

95A. The convertible plunger of embodiment 1A, wherein the film or cap comprise a fluoropolymer.

While the invention has been described in detail and with reference to specific examples thereof, it will be apparent to one skilled in the art that various changes and modifications can be made therein without departing from the spirit and scope thereof.

What is claimed is:

1. A convertible plunger comprising:
    a. a first subassembly comprising a connector body having a distal end and a proximal end, the proximal end of the connector body comprising a recess or axial channel, the first subassembly further comprising a plunger head, which is a separate component that is assembled to the distal end of the connector body, the plunger head having a liquid sealing section configured to contact and provide a seal against an interior wall of a medical barrel when disposed therein;
    b. a second subassembly comprising an elongate ring carrier having a distal end and a proximal end, the distal end of the ring carrier being secured to the proximal end of first subassembly, the proximal end of the ring carrier being configured to be secured to a plunger rod, the ring carrier comprising an annular dispensing platform and an annular storage platform distal to the dispensing platform, the annular storage platform having a larger maximum diameter or cross-sectional width than the dispensing platform, the ring carrier further comprising an annular insertion platform distal to the annular storage platform, the annular insertion platform having a smaller maximum diameter or cross-sectional width than the storage platform, the insertion platform being disposed in the recess or axial channel so as to fixedly secure the first subassembly to the second subassembly, the second subassembly further comprising a compressible and resilient storage ring disposed about the ring carrier and configured to displace axially thereon;
    c. wherein the storage platform is more rigid than the storage ring.

2. The convertible plunger of claim 1, comprising a fluoropolymer film wrapped about the liquid sealing section.

3. The convertible plunger of claim 1, wherein the storage ring includes at least two annular ribs separated by an annular valley therebetween.

4. The convertible plunger of claim 1, wherein the storage ring in an uncompressed state comprises a rib on an inside surface of the storage ring and an opposing rib on the outer surface of the storage sealing section.

5. The convertible plunger of claim 1, the storage ring comprising an outer surface facing generally radially outward away from the ring carrier, wherein when the storage ring is in an uncompressed state, the outer surface comprises a proximal end, a distal end and a radial plane of symmetry between the proximal and distal ends that is equidistant from the proximal and distal ends, wherein the outer surface is symmetrical on either side of the radial plane of symmetry.

6. The convertible plunger of claim 1, the storage ring comprising an inner surface facing inward toward the ring carrier, the inner surface having a width that runs from a proximal end of the storage ring to a distal end of the storage ring, wherein, when the storage ring is uncompressed, the inner surface is symmetrical across the width of the inner surface of the storage ring.

7. The convertible plunger of claim 6, wherein the storage ring includes at least two annular ribs separated by an annular valley therebetween.

8. A pre-filled syringe comprising:
   a. a medical barrel having an inner wall and an injectable drug product disposed in a product containing area of the medical barrel, the medical barrel having a distal dispensing end for dispensing the injectable drug product and an open proximal end configured for receipt of a convertible plunger; and
   b. a convertible plunger disposed within the medical barrel, the convertible plunger comprising:
      (I) a first subassembly comprising a connector body having a distal end and a proximal end, the first subassembly further comprising a plunger head, which is a separate component that is assembled to the distal end of the connector body, the plunger head having a liquid sealing section configured to contact and provide a seal against an interior wall of a medical barrel when disposed therein;
      (II) a second subassembly comprising an elongate ring carrier having a distal end and a proximal end, the distal end of the ring carrier being secured to the proximal end of first subassembly, the proximal end of the ring carrier being configured to be secured to a plunger rod, the ring carrier comprising an annular dispensing platform and an annular storage platform distal to the dispensing platform, the annular storage platform having a larger maximum diameter or cross-sectional width than the dispensing platform, the second subassembly further comprising a compressible and resilient storage ring disposed about the ring carrier and configured to displace axially thereon;
      (III) wherein the storage platform is more rigid than the storage ring;
   wherein the storage sealing section, when the storage ring is disposed about the storage platform, is maintained in an expanded state by outward radial pressure provided by the storage platform to create compression between the storage sealing section and the inner wall of the barrel, thereby rendering the convertible plunger in storage mode, the expanded state being reducible to a constricted state upon transitioning the storage ring to being disposed about the dispensing platform whereupon the compression between the storage sealing section and the inner wall of the barrel is reduced or eliminated, thereby rendering the convertible plunger in dispensing mode.

9. The pre-filled syringe of claim 8, wherein the entire storage ring is disposed about the storage platform when the plunger is in storage mode.

10. The pre-filled syringe of claim 9, wherein the entire storage ring is disposed about the dispensing platform when the plunger is in dispensing mode.

11. The pre-filled syringe of claim 8, wherein the storage sealing section is configured to be set in the expanded state through application of a setting force onto the convertible plunger in a distal direction.

12. The pre-filled syringe of claim 11, wherein the convertible plunger in storage mode is configured to transition to dispensing mode upon providing an actuation force onto the convertible plunger in a distal direction.

13. The pre-filled syringe of claim 8, the proximal end of the connector body comprising a recess or axial channel, the ring carrier further comprising an annular insertion platform distal to the annular storage platform, the annular insertion platform having a smaller maximum diameter or cross-sectional width than the storage platform, wherein the insertion platform is configured to be disposed in the recess or axial channel so as to fixedly secure the first subassembly to the second subassembly.

14. A method for assembling the convertible plunger into the pre-filled syringe of claim 13, the method comprising the following steps:
   i. loading the first subassembly into the medical barrel through the open proximal end thereof;
   ii. positioning the storage ring about the insertion platform so as to place the storage ring in a load position and axially aligning the second subassembly with the first subassembly;
   iii. after step (ii) and while the storage ring is in the load position, disposing the second subassembly into the open proximal end of the medical barrel at least to a depth in which the storage ring is disposed within the medical barrel; and
   iv. securing the first subassembly to the second subassembly by disposing the insertion platform in the recess or axial channel, thereby assembling the convertible plunger;
   wherein step (iv) causes the storage ring to move from the load position to the expanded state, thereby placing the plunger in storage mode.

15. The method of claim 14, wherein the storage sealing section is configured to be set in the expanded state through application of a setting force onto the convertible plunger in a distal direction.

16. The method of claim 15, wherein the convertible plunger in storage mode is configured to transition to dispensing mode upon providing an actuation force onto the convertible plunger in a distal direction.

17. A convertible plunger comprising:
   a. a first subassembly comprising a connector body having a distal end and a proximal end, the first subassembly further comprising a plunger head, which is a separate component that is assembled to the distal end of the connector body, the plunger head having a liquid sealing section configured to contact and provide a seal against an interior wall of a medical barrel when disposed therein;
   b. a second subassembly comprising an elongate ring carrier having a distal end and a proximal end, the distal end of the ring carrier being secured to the proximal end of first subassembly, the proximal end of the ring carrier being configured to be secured to a plunger rod, the ring carrier comprising an annular dispensing platform and an annular storage platform distal to the dispensing platform, the annular storage platform having a larger maximum diameter or cross-sectional width than the dispensing platform, the second subassembly further comprising a compressible and resilient storage ring disposed about the ring carrier and configured to displace axially thereon, the storage ring comprising an outer surface facing generally radially outward away from the ring carrier, wherein when the storage ring is in an uncompressed state, the outer surface comprises a proximal end, a distal end and a radial plane of symmetry between the proximal and distal ends that is equidistant from the proximal and distal ends, wherein the outer surface is symmetrical on either side of the radial plane of symmetry;

c. wherein the storage platform is more rigid than the storage ring.

\* \* \* \* \*